US006730476B1

(12) United States Patent
Duff et al.

(10) Patent No.: US 6,730,476 B1
(45) Date of Patent: *May 4, 2004

(54) METHODS OF DIAGNOSING EARLY-ONSET MENOPAUSE

(75) Inventors: Gordon Duff, South York (GB); Kenneth Kornman, Newton, MA (US); Simon van Dijk, San Antonio, TX (US)

(73) Assignee: Interleukin Genetics, Inc., Waltham, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 09/632,657

(22) Filed: Aug. 4, 2000

Related U.S. Application Data

(63) Continuation-in-part of application No. 09/345,217, filed on Jun. 30, 1999, now Pat. No. 6,268,142.

(51) Int. Cl.[7] .............................. C12Q 1/68; C12P 19/34; C07H 21/02; C07H 21/04
(52) U.S. Cl. ......................... 435/6; 435/91.2; 536/23.5; 536/24.31; 536/24.33
(58) Field of Search ................... 435/6, 91.2; 536/23.5, 536/24.31, 24.33

(56) References Cited

U.S. PATENT DOCUMENTS

| | | | |
|---|---|---|---|
| 4,656,127 A | 4/1987 | Mundy | 435/6 |
| 4,683,195 A | 7/1987 | Mullis et al. | 435/6 |
| 4,683,202 A | 7/1987 | Mullis | 435/91 |
| 5,192,659 A | 3/1993 | Simons | 435/6 |
| 5,459,039 A | 10/1995 | Modrich et al. | 435/6 |
| 5,593,826 A | 1/1997 | Fung et al. | 435/6 |
| 6,268,142 B1 * | 7/2001 | Duff et al. | |

FOREIGN PATENT DOCUMENTS

| | | |
|---|---|---|
| WO | WO 91/02087 | 2/1991 |
| WO | WO 94/16101 | 7/1994 |
| WO | WO98/54359 | * 12/1998 |

OTHER PUBLICATIONS

Bailly et al.; "An Intronic Polymorphic Repeat Sequence Modulates Interleukin–1 Alpha Gene Regulation", Molecular Immunology, 33(11/12): 999–1006 (1996).
Bailly et al.; "Genetic Polymorphism of Human Interleukin–1α", Eur. J. Immunol. 23: 1240–1245 (1993).
Barany Francis; "Genetic Disease Detection and DNA Amplification Using Cloned Thermostable Ligase", Proc. Natl. Acad. Sci. USA, 88: 189–193 (Jan. 1991).
Bradley et al.; "Formation of Germ–line Chimaeras From Embryo–Derived Teratocarcinom Cell lines", Nature 309: 255–256 (May 17, 1984).
Cassou et al.; "Risk Factors of Early Menopause in Two Generations of Gainfully Employed French Women", Maturitas, 26: 165–174 (1997).
Clay et al.; "Novel Interleukin–1 Receptor Antagonist Exon Polymorphisms and Their Use in Allele–Specific mRNA Assessment", Hum. Genet 97: 723–726 (1996).
Clark et al.; "Genomic Sequence For Human Prointerleukin 1 beta: Possible Evolution from a Reverse Transcribed Prointerleukin 1 Alpha Gene", Nucleic Acid Research 14(20): 7897–7915 (1986).
Clark et al.; "Genomic Sequence For Human Prointerleukin 1 beta: Possible Evolution From a Reverse Transcribed Prointerleukin 1 Alpha Gene", Nucleic Acid Research 15(2):868 (Jan. 1987).
Cotton et al.; "Reactivity of Cytosine and Thymine in Single–base–pair Mismatches with Hydroxylamine and Osmium Tetroxide and its Application to the Study of Mutations", Proc. Natl. Acad. Sci. USA, 85: 4397–4401 (Jun. 1988).
An Analysis of Linkage Disequilibrum in the Interleukin–1 Gene Cluster, Using a Novel Grouping Methods for Multiallelic Markers, Am. J. Hum. Genet. 62: 1180–1188 (1998).
Cramer et al.; "Family History as a Predictor of Early Menopause", Fertility and Sterility 64(4): 740–745 (Oct. 1995).
Gibbs et al.; "Detection of Single DNA Base Differences by Competitive Oligonucleotide Priming", Nucleic Acids Research 17(7): 2437–2449 ((1989).
Hsu et al.; "Detection of DNA Point Mutations with DNA Mismatch Repair Enzymes", Carcinogenesis 15(8): 1657–1662 (1994).
Kaipia and Hsueh; "Regulation of Ovarian Follicle Atresia", Annu. Rev. Physiol. 59: 349–363 (1997).
Kornher and J. Livak; "Mutation Detection Using Nucleotide Analogs that Alter Electrophoretic Mobility", Nucleic Acids Research, 17(19): 7779–7785 (1989).
Kuppuswamy et al.; "Single Nucleotide Primer Extension to Detect Genetic Disease: Experimental Application to Hemophilia B (factor IX) and Cystic Fibrosis Genes", Proc. Natl. Acad. Sci. USA, 88: 1143–1147 (Feb. 1991).
Landegren et al.; "A Ligase–Madiated Gene Detection Technique", Science 241: 1077–1080 (Aug. 26, 1988).
Lennard C. Andrew; "Interleukin–1 Receptor Antagonist", Critical Review in Immunology, 15(1): 77–105 (1995).
Luijt et al.; "Rapid Detection of Translation–Terminating Mutations at the Adenomatous Polyposis Coli(APC) Gene by Direct Protein Truncation Test", Genomics 20: 1–4 (1994).
Machelon; "Marcophage and Granulosa Interleukin –1β m RNA in Human Ovulatory Follicles", Molecular Human Reproduction 10 (8):2198–2203 (1995).

(List continued on next page.)

Primary Examiner—Carla J. Myers
(74) Attorney, Agent, or Firm—Ivor R. Elrifi, Esq.; Cynthia A. Kowakiewicz, Esq.; Mintz, Levin, Cohn, Ferris, Glovsky and Popeo, P.C.

(57) ABSTRACT

A method of predicting whether a subject is predisposed to developing early-onset menopause is provided. The method involves genotyping a patient at the IL-1 gene loci.

7 Claims, 12 Drawing Sheets

OTHER PUBLICATIONS

McDowell et al.; "A Genetic Association Between Juvenile Rheumatoid Arthritis and a Novel Interleukin –1α polymorphism", Arthritis & Rheumatism , 38 (2): 221–228 (Feb. 1995).

McKinlay et al., "The Normal Menopause Transition", Maturitas , 14: 103–115.

Münster et al.; "Length and Variation in the Menstrual Cycle—a Cross–Sectional Study from a Danish County", British Journal of Obstetric and Gynaecology, 99: 422–429 (May 1992).

Myers et al.; "Detection of Single Base Substitutions by Ribonuclease Cleavage at Mismatches in RNA: DNA Duplexes", Science 230: 1242–1246 (Dec. 13, 1985).

Myers et al.; "Detection of Single Base Substitutions in Total Genomic DNA", Nature, 313: 495–498 (Feb. 7, 1985).

Nickerson et al.; "Automated DNA Diagnostics using ELISA–Based Oligonucleotide Ligation Assay", Proc. Ntl. Acad. Sci. USA, 87: 8923–8927 (Nov. 1990).

Nicklin et al.; "A Physical Map of the Region Encompassing the Human Interleukin–1α, Interleukin–1β, and Interleukin–1 Receptor Antagonist Genes", Genomics 19: 382–384, (1994).

Nothwang et al.; "Molecule cloning of the Interleukin–1 Gene Cluster: Construction of an Integrated YAC/PAC Contig and a Partial Transcriptional Map Region of Chromosome 2q13", Genomics 41: 370–378, (1997).

Orita et al.; "Detection of Polymorphisms of Human DNA by Gel electrophoresis as Single –Strand conformation Polymorphisms", Proc. Natl. Acad. Sci. USA, 86: 2766–2770, (Apr. 1989).

Pociot et al.; "A Taql Polymorphism in the Human interleukin–1β (1 L–1β) Gene Correlates with 1L–1β Secretion in Vivo", European Journal of Clinical Investigation 22: 396–402 (1992).

Saiki et al.; "Analysis of Enzymatically Amplified β–Globin HLA–DQα DNA with Allele– Specific Oligonucleotide Probes", Nature 234: 163–166, (Nov. 13, 1986).

Saiki et al.; "Genetic Analysis of Amplified DNA with Immobilized Sequence–Specific Oligonucleotide Probes", Proc. Natl. Acad. Sci. USA, 86: 6230–6234, (Aug. 1989).

Snieder et al.; "Genes control the Cessation of a Women's Reproductive Life: A Twin Study of Hysterectomy and Age at Menopause", Journal of Clinical Endocrinology and Metabolism. 83(6): 1875–1880 (1998).

Sokolov P. Boris; "Primer Extension Technique for the Detection of Single Nucleotide in Genomic DNA", Nucleic Acids Research 18(12): 3671, (1989).

Stanford et al; "Factors Influencing the Age at Natural Menopause", J. Chrom. Dis. 40 (11): 995–1002 (1987).

Syvänen et al.; "Identification of Individuals by analysis of Biallelic DNA Markers, Using PCR and Solid–Phase Minisequencing", Am. J. Hum. Genet. 52: 46–59 (1993).

Tarlow et al.; "Severity of Alopecia Areata Is Associated with a Polymorphism in the Interleukin–1 Receptor Antagonist Gene", The Journal of Investigative Dermatology, 103(3): 387–390 (Sep. 1994).

Terranova and Rice; "Review: Cytokine Involvement in Ovarian Processes", AJRI, 37: 50–63 (1997).

Tobe et al.; "Single–Well Genotyping of Diallelic Sequence Variations by a Two–color ELISA–based Oligonucleotide Ligation Assay", Nucleic Acids Research 24(19): 3728–3732 (1996).

Tsafriri Alex; "Ovulation as a Tissue Remodelling Process", Adv. Exp. Med. Biol. 377: 121–140 (1995).

Torgerson et al.; "Mothers and Daughters Menopausal Age: Is There a Link?", European Journal of Obsterstrics and Gynecology and Reproductive Biology 74: 63–66 (1997).

Tringali et al.; "The Release of Immunoreactivity Interleukin–1β From Rat Hypothalamic Explants Modulated by Neurotransmitters and Corticotropin–Releasing Hormone", Pharmacological Research 36(4): 269–273, (1997).

A Negative Regulatory Region Containing a Glucocorticosteriod Response Element (nGRE) in the Human Interleukin–1β Gene, DNA and Cell Biology 16(2): 145–152, (1997).

Zuliani and Hobbs; "A High Frequency of Length Polymorphisms in Repeated Sequences Adjacent to Alu Sequences", Am. J. Hum. Genet., 46: 963–969, (1990).

Keen et al.; "Early Menopausal Bone Loss at the Spine is Associated with Polymorphism at the Interleukin 1 Receptor Antagonist Locus", Journal of Bone and Mineral Research, 12 (Suppl 1): S256(T620 ), (Aug. 1997).

Keen et al.; "Allelic Variation at the Interleukin–1 Receptor Antagonist Gene Is Associated with Early Postmenopausal Bone Loss at the Spine", Bone 23(4): 367–371 (Oct. 1998).

* cited by examiner

IL-1A (GEN X03833; SEQ ID No. 1)

```
   1 aagcttctac cctagtctgg tgctacactt acattgctta catccaagtg tggttatttc
  61 tgtggctcct gttataacta ttatagcacc aggtctatga ccaggagaat tagactggca
 121 ttaaatcaga ataagagatt ttgcacctgc aatagacctt atgacaccta accaacccca
 181 ttatttacaa ttaaacagga acagagggaa tactttatcc aactcacaca agctgttttc
 241 ctcccagatc catgcttttt tgcgtttatt attttttaga gatggggct tcactatgtt
 301 gcccacactg gactaaaact ctgggcctca agtgattgtc ctgcctcagc ctcctgaata
 361 gctgggacta caggggcatg ccatcacacc tagttcattt cctctattta aatatacat
 421 ggcttaaact ccaactggga acccaaaaca ttcatttgct aagagtctgg tgttctacca
 481 cctgaactag gctggccaca ggaattataa agctgagaa attctttaat aatagtaacc
 541 aggcaacatc attgaaggct catatgtaaa atccatgcc ttcctttctc ccaatctcca
 601 ttcccaaact tagccactgg ttctggctga ggcttacgc atacctccg gggcttgcac
 661 acaccttctt ctacagaaga cacaccttgg gcatatccta cagaagacca ggcttctctc
 721 tggtccttgg tagagggcta ctttactgta acagggccag ggtggagagt tctctcctga
 781 agctccatcc cctctatagg aaatgtgttg acaatattca gaagagtaag aggatcaaga
 841 cttctttgtg ctcaaatacc actgttctct tctctaccct gccctaacca ggagcttgtc
 901 accccaaact ctgaggtgat ttatgcctta atcaagcaaa cttccctctt cagaaaagat
 961 ggctcatttt ccctcaaaag ttgccaggag ctgccaagta ttctgccaat tcaccctgga
1021 gcacaatcaa caaattcagc cagaacacaa ctacagctac tattagaact attattatta
1081 ataaattcct ctccaaatct agcccttga cttcggattt cacgatttct cccttcctcc
1141 tagaaacttg ataagtttcc cgcgcttccc ttttctaag actacatgtt tgtcatctta
1201 taaagcaaag gggtgaataa atgaaccaaa tcaataactt ctggaatatc tgcaaacaac
1261 aataatatca gctatgccat ctttcactat tttagccagt atcgagttga atgaacatag
1321 aaaatacaa aactgaattc ttccctgtaa attccccgtt tgacgacgc acttgtagcc
1381 acgtagccac gcctacttaa gacaattaca aaaggcgaag aagactgact caggcttaag
1441 ctgccagcca gagagggagt catttcattg gcgtttgagt cagcaaaggt attgtcctca
1501 catctctggc tattaaagta ttttctgttg ttgttttct ctttggctgt tttctctcac
1561 attgccttct ctaaagctac agtctctcct ttcttttctt gtccctccct ggtttggtat
1621 gtgacctaga attacagtca gatttcagaa aatgattctc tcattttgct gataaggact
1681 gattcgtttt actgagggac ggcagaacta gtttcctatg agggcatggg tgaatacaac
1741 tgaggcttct catgggaggg aatctctact atccaaaatt attaggagaa aattgaaaat
1801 ttccaactct gtctctctct tacctctgtg taaggcaaat accttattct tgtggtgttt
1861 ttgtaacctc ttcaaacttt cattgattga atgcctgttc tgcaataca ttaggttggg
1921 cacataagga ataccaacat aaataaaaca ttctaaaaga gtttacgat ctaataaagg
1981 agacaggtac atagcaaact aattcaaagg agctagaaga tggagaaaat gctgaatgtg
2041 gactaagtca ttcaacaaag ttttcaggaa gcacaaagag gaggggctcc cctcacagat
2101 atctggatta gaggctggct gagctgatgg tggctggtgt tctctgttgc agaagtcaag
2161 atggccaaag ttccagacat gtttgaagac ctgaagaact gttacaggta aggaataaga
2221 tttatctctt gtgatttaat gagggtttca aggctcacca gaatccagct aggcataaca
2281 gtggccagca tggggcagg ccggcagagg ttgtagagat gtgtactagt cctgaagtca
2341 gagcaggttc agagaagacc cagaaaaact aagcattcag catgttaaac tgagattaca
2401 ttggcaggga gaccgccatt ttagaaaaat tattttgag gtctgctgag ccctacatga
2461 atatcagcat caacttagac acagcctctg ttgagatcac atgccctgat ataagaatgg
2521 gttttactgg tccattctca ggaaaacttg atctcattca ggaacaggaa atggctccac
2581 agcaagctgg gcatgtgaac tcacatatgc aggcaaatct cactcagatg tagaagaaag
2641 gtaaatgaac acaaagataa aattacgaa catattaaac taacatgatg tttccattat
2701 ctgtagtaaa tactaacaca aactaggctg tcaaaatttt gcctggatat tttactaagt
2761 ataattatg aaatctgttt tagtgaatac atgaaagtaa tgtgtaacat ataatctatt
2821 tggttaaaat aaaaggaag tgcttcaaaa cctttctttt ctctaaagga gcttaacatt
2881 cttccctgaa cttcaattaa agctcttcaa tttgttagcc aagtccaatt tttacagata
2941 aagcacaggt aaagctcaaa gcctgtcttg atgactacta attccagatt agtaagatat
3001 gaattactct acctatgtgt atgtgtagaa gtccttaaat ttcaaagatg acagtaatgg
3061 ccatgtgtat gtgtgtgacc cacaactatc atggtcatta aagtacattg ccagagacc
3121 acatgaaata acaacaatta cattctcatc atcttatttt gacagtgaaa atgaagaaga
```

FIGURE 1

```
3181 cagttcctcc attgatcatc tgtctctgaa tcaggtaagc aaatgactgt aattctcatg
3241 ggactgctat tcttacacag tggtttcttc atccaaagag aacagcaatg acttgaatct
3301 taaatacttt tgttttaccc tcactagaga tccagagacc tgtctttcat tataagtgag
3361 accagctgcc tctctaaact aatagttgat gtgcattggc ttctcccaga acagagcaga
3421 actatcccaa atccctgaga actggagtct cctggggcag gcttcatcag gatgttagtt
3481 atgccatcct gagaaagccc cgcaggccgc ttcaccaggt gtctgtctcc taacgtgatg
3541 tgttgtggtt gtcttctctg acaccagcat cagaggttag agaaagtctc caaacatgaa
3601 gctgagagag aggaagcaag ccagctgaaa gtgagaagtc tacagccact catcaatctg
3661 tgttattgtg tttggagacc acaaatagac actataagta ctgcctagta tgtcttcagt
3721 actggcttta aaagctgtcc ccaaaggagt atttctaaaa tatttgagc attgttaagc
3781 agatttttaa cctcctgaga gggaactaat tggaaagcta ccactcacta caatcattgt
3841 taacctattt agttacaaca tctcattttt gagcatgcaa ataaatgaaa aagtcttcct
3901 aaaaaaatca tcttttatc ctggaaggag gaaggaaggt gagacaaaag ggagagaggg
3961 agggaagcct aatgaaacac cagttaccta agaccagaat ggagatcctc ctcactacct
4021 ctgttgaata cagcacctac tgaaagaact ttcattccct gaccatgaac agcctctcag
4081 cttctgtttt ccttcctcac agaaatcctt ctatcatgta agctatggcc cactccatga
4141 aggctgcatg gatcaatctg tgtctctgag tatctctgaa acctctaaaa catccaagct
4201 taccttcaag gagagcatgg tggtagtagc aaccaacggg aaggttctga agaagagacg
4261 gttgagttta agccaatcca tcactgatga tgacctggag gccatcgcca atgactcaga
4321 ggaaggtaag gggtcaagca caataatatc tttcttttac agttttaagc aagtagggac
4381 agtagaattt aggggaaaat taaacgtgga gtcagaataa caagaagaca accaagcatt
4441 agtctggtaa ctatacagag gaaaattaat ttttatcctt ctccaggagg gagaaatgag
4501 cagtggcctg aatcgagaat acttgctcac agccattatt cttagccat attgtaaagg
4561 tcgtgtgact tttagccttt caggagaaag cagtaataag accacttacg agctatgttc
4621 ctctcatact aactatgcct ccttggtcat gttacataat cttttcgtga ttcagtttcc
4681 tctactgtaa aatggagata atcagaatcc cccactcatt ggattgtgt aaagattaag
4741 agtctcaggc tttacagact gagctagctg ggcctcctg actgttataa agattaaatg
4801 agtcaacatc ccctaacttc tggactagaa taatgtctgg tacaaagtaa gcacccaata
4861 aatgttagct attactatca ttattattat tattttattt tttttttttg agatggagtc
4921 tggctctgtc acccaggctg gagtgcagtg gcacaatctc ggctcactgc aagctctgcc
4981 tcctgggttc atgccattct cctgcctcag cctcccgagt aagctgggaa tacaggcacc
5041 cgccactgtt cccggctaat ttttgtatt tttagtagag acggagtttc accgtggtct
5101 ccatctcctc gtgatccacc caccttggcc tcccaaagtg ccgggattac aggcgtgagc
5161 caccgcgccc ggcctattat tattattatt actactacta ctacctatat gaatactacc
5221 agcaatacta atttattaat gactggatta tgtctaaacc tcacaagaat cctaccttct
5281 cattttacat aaaaggaaac taagctcatt gagataggta aactgcccaa tggcatacat
5341 ctgtaagtgg gagagcctca aatctaattc agttctacct gagtaaaaaa atcatggttt
5401 ctcctccatc cctttactgt acaagcctcc acatgaacta taaacccaat attcctgttt
5461 ttaagataat acctaagcaa taacgcatgt tcacctagaa ggttttaaaa tgtaacaaaa
5521 tataagaaaa taaaatcac tcatatcgtc agtgagagtt tactactgcc agcactatgg
5581 tatgtttcct taaaatcttt gctatacaca tacctacatg tgaacaaata tgtctaacat
5641 caagaccaca ctatttacaa ctttatatcc agcttttctt acttagcaat gtattgagga
5701 catttagag tgcccgtttt tcaccattat aagcaatgca acaatgaaca tctgtataaa
5761 taaatattca tttctctcac cctttatttc cttagaatat attcctagaa gtagaatttc
5821 ccagagccat gaggatttgt gacgctattg atatgtgcca ctttgcactc tctgtgacat
5881 atataattat ttttaatgca ttcattttt tctcagagtg cattcgtttg aaaacataga
5941 cgggaaatac tggtagtctt ccttgtcagt tagaaacacc caaacaatga aaaatgaaaa
6001 agttgcacaa atagtctcta aaaacaatga actattgcc tgaggaattg aagtttaaaa
6061 agaagcacat aagcaacaac aaggataatc ctagaaaacc agttctgctg actgggtgat
6121 ttcacttctc tttgcttcct catctggatt ggaatattcc taatacccc tccagaacta
6181 ttttccctgt ttgtactaga ctgtgtatat catctgtgtt tgtacataga cattaatctg
6241 cacttgtgat catggtttta gaaatcatca agcctaggtc atcacctttt agcttcctga
6301 gcaatgtgaa atacaacttt atgaggatca tcaaatacga attcatcctg aatgacgccc
6361 tcaatcaaag tataattcga gccaatgatc agtacctcac ggctgctgca ttacataatc
6421 tggatgaagc aggtacatta aaatgcacc agacatttct gtcatcctcc cctcctttca
6481 tttacttatt tatttatttc aatctttctg cttgcaaaaa acatacctct tcagagttct
6541 gggttgcaca attcttccag aatagcttga agcacagcac ccccataaaa atcccaagcc
```

FIGURE 1

```
6601 agggcagaag gttcaactaa atctggaagt tccacaagag agaagtttcc tatctttgag
6661 agtaaagggt tgtgcacaaa gctagctgat gtactacctc tttggttctt tcagacattc
6721 ttaccctcaa ttttaaaact gaggaaactg tcagacatat taaatgattt actcagattt
6781 acccagaagc caatgaagaa caatcactct cctttaaaaa gtctgttgat caaactcaca
6841 agtaacacca aaccaggaag atctttatta tctctgataa catatttgtg aggcaaaacc
6901 tccaataagc tacaaatatg gcttaaagga tgaagtttag tgtccaaaaa cttttatcac
6961 acacatccaa ttttcatggc ggacatgttt tagtttcaac agtatacata ttttcaaagg
7021 tccagagagg caattttgca ataaacaagc aagactttt ctgattggat gcacttcagc
7081 taacatgctt tcaactctac atttacaaat tattttgtgt tctattttc tacttaatat
7141 tatttctgca attttcccaa tattgacatc gtgtatgtat ttgccatttt taatatcact
7201 agacaattca atcaggttgc tacgttggtc ccttgggttt actctaaata gcttgattgc
7261 aaatatcttt gtatatatta ttgttttttc tcctatcttg taatttcttt gagcacatcc
7321 caaagaggaa tgcctagatc aatgggcaca ataatttga cagctcttat taaacattat
7381 tctgtaagta aaaactgaac tacttttcag tatcactagc aacatatgag tgtatcagct
7441 tcctaaaccc ctccatgtta ggtcattatg aacttatgat ctaacaaatt acagggtctt
7501 atcccactaa tgaaattata agagattcaa cacttattca gccccgaagg attcattcaa
7561 cgtagaaaat tctaagaaca ttaaccaagt atttacctgc ctagtgagtg tggaagacat
7621 tgtgaaggac acaaagatgt atagaattcc attcctgact tccaggtatt tacaccatag
7681 gtggggacct aactacacac acacacacac acacacacac acacacacac accatgcaca
7741 cacaatctac atcaacactt gattttatac aaatacaatg aatttacttt cttttggtt
7801 cttctcttca ccagtgaaat ttgacatggg tgcttataag tcatcaaagg atgatgctaa
7861 aattaccgtg attctaagaa tctcaaaaac tcaattgtat gtgactgccc aagatgaaga
7921 ccaaccagtg ctgctgaagg tcagttgtcc tttgtctcca acttaccttc atttacatct
7981 catatgtttg taaataagcc caataggcag acacctctaa caaggtgaca ctgtcctctt
8041 tccttcctac cacagccccc acctacccac cccactccca ttgattccag aggcgtgcct
8101 aggcaggatc tatgagaaaa tataacagag agtaagagga aaattacctt ctttcttttt
8161 cctttccctg cctgacctta ttcacctccc atcccagagc atccatttat tccattgatc
8221 tttactgaca tctattatct gacctacaca atactagaca ttaggacaat gtggcctgcc
8281 tccaagaaac tcaaataagc caactgagat cagagaggat taatcacctg ccaatgggca
8341 caaagcaaca agctgggagc caagtcccaa aatggggcct gctgcttcca gttcccctct
8401 ctctgcattg atgtcagcat tatccttcgt cccagtcctg tctccactac cactttcccc
8461 ctcaaacaca cacacacaca acagccttag atgttttctc cactgataag taggtgactc
8521 aatttgtaag tatataatcc aagaccttct attcccaagt agaatttatg tgcctgcctg
8581 tgcttttcta cctggatcaa gtgatgtcta cagagtaggg cagtagcttc attcatgaac
8641 tcattcaaca agcattattc actgagagcc ttgtattttt caggcatagt gccaacagca
8701 gtgtggacag tggtgcatca aagcctctag tctcatagaa cttagtcttc tggaggatat
8761 ggaaaacaga caacccaaac aaccaacaaa agagcaagat gctgcaaaaa aaaaaaaaat
8821 gaatagggtg ctaagataga gaaaagtggg agagtgctat ttagacaaag tggtaaaaac
8881 aaagcccctt gtgagatgag agctgccgac agaggggcg ggtcatggtt gtgggttttt
8941 gggtaggaca ttcagaggag ggggcgggtc gtggttgtgg gttttgggt aggacattca
9001 gaggagggg cgggtcgtgg ttgtgggttt tgggtagga cattcagagg aggggcggg
9061 tcgtggttgt gggttttttgg gtaggacatt cagaggaggg ggcgggtcgt ggttgtgggt
9121 ttttgggaca ttcagaggag tctgaatgca cccaggccta caacttcaag atggtaaagg
9181 acagctccaa ggatcagaag aagcattctt ggaactgggg cattttgaga aggaggaaaa
9241 atatgcagag actagtgctt gcagagcttg catttggatt tcatttgagg tacaatgaaa
9301 acccattaat gggtttcaca cagtgcaatg gcctgacctc acttatattt cctaaaatag
9361 aaaacagatc agaaggaagg caatagagaa gcagaaagtc caatgaggag gtttcacagc
9421 agtcatgggg gtggggtaag gaaaagaagt ggaaagaaac agacagaatt gggttatatt
9481 ttggagatag aaccaacaga aggaagagga gaaacaacat ttactgagaa gggaaaaagt
9541 aggagaggaa taggtttggg aaataaatcc tgctgacatt ggaaacccca aggaagcctc
9601 aaaagtatat ttacttgctt tagatttaaa agaataggaa agaagcatct caacttggaa
9661 tttgaaatct attttccat aaaagtattg ttaaattcta ctcatactca caagaaaagt
9721 acattctaaa gagtatattg aaagagttta ctgatatact taggaatttt gtgtgtatgt
9781 gtgtgtgtgt atgtgtgtgt gtgtgtttaa ccttcaattg ttgacttaaa tactgagata
9841 aatgtcatct aaatgctaaa ttgatttccc aaaggtatga tttgttcact tggagatcaa
9901 aatgtttagg gggcttagaa tcactgtagt gctcagattt gatgcaaaat gtcttaggcc
9961 tatgttgaag gcaggacaga acaatgtttt ccctcctacc tgcctggata cagtaagata
```

FIGURE 1

```
10021 ctagtgtcac tgacaatctt cataactaat ttagatctct ctccaatcaa ctaaggaaat
10081 caactcttat taatagactg ggccacacat ctactaggca tgtaataaat gcttgctgaa
10141 tgaacaaatg aatgaagagc ctatagcatc atgttacagc catagtccta aagtggtgtt
10201 tctcatgaag gccaaatgct aagggattga gcttcagtcc tttttctaac atcttgttct
10261 ctaacagaat tctcttcttt tcttcatagg agatgcctga gatacccaaa accatcacag
10321 gtagtgagac caacctcctc ttcttctggg aaactcacgg cactaagaac tatttcacat
10381 cagttgccca tccaaacttg tttattgcca caaagcaaga ctactgggtg tgcttggcag
10441 gggggccacc ctctatcact gactttcaga tactggaaaa ccaggcgtag gtctggagtc
10501 tcacttgtct cacttgtgca gtgttgacag ttcatatgta ccatgtacat gaagaagcta
10561 aatcctttac tgttagtcat ttgctgagca tgtactgagc cttgtaattc taaatgaatg
10621 tttacactct ttgtaagagt ggaaccaaca ctaacatata atgttgttat ttaaagaaca
10681 ccctatattt tgcatagtac caatcatttt aattattatt cttcataaca attttaggag
10741 gaccagagct actgactatg gctaccaaaa agactctacc catattacag atgggcaaat
10801 taaggcataa gaaaactaag aaatatgcac aatagcagtt gaaacaagaa gccacagacc
10861 taggatttca tgatttcatt tcaactgttt gccttctgct tttaagttgc tgatgaactc
10921 ttaatcaaat agcataagtt tctgggacct cagttttatc attttcaaaa tggagggaat
10981 aatacctaag ccttcctgcc gcaacagttt tttatgctaa tcagggaggt cattttggta
11041 aaatacttct cgaagccgag cctcaagatg aaggcaaagc acgaaatgtt attttttaat
11101 tattatttat atatgtattt ataaatatat ttaagataat tataatatac tatatttatg
11161 ggaacccctt catcctctga gtgtgaccag gcatcctcca caatagcaga cagtgttttc
11221 tgggataagt aagtttgatt tcattaatac agggcatttt ggtccaagtt gtgcttatcc
11281 catagccagg aaactctgca ttctagtact tgggagacct gtaatcatat aataaatgta
11341 cattaattac cttgagccag taattggtcc gatctttgac tcttttgcca ttaaacttac
11401 ctgggcattc ttgtttcatt caattccacc tgcaatcaag tcctacaagc taaaattaga
11461 tgaactcaac tttgacaacc atgagaccac tgttatcaaa actttctttt ctggaatgta
11521 atcaatgttt cttctaggtt ctaaaaattg tgatcagacc ataatgttac attattatca
11581 acaatagtga ttgatagagt gttatcagtc ataactaaat aaagcttgca acaaaattct
11641 ctgacacata gttattcatt gccttaatca ttattttact gcatggtaat tagggacaaa
11701 tggtaaatgt ttacataaat aattgtattt agtgttactt tataaaatca accaagatt
11761 ttatattttt ttctcctctt tgttagctgc cagtatgcat aaatggcatt aagaatgata
11821 atatttccgg gttcacttaa agctcatatt acacatacac aaaacatgtg ttcccatctt
11881 tatacaaact cacacataca gagctacatt aaaaacaact aataggccag gcacggtggc
11941 tcagacctgt aatcccagca ctttgggagg
```

FIGURE 1

IL-1B (GEN X04500; SEQ. ID. No. 2)

```
   1 agaaagaaag agagagagaa agaaaagaaa gaggaaggaa ggaaggaagg aagaaagaca
  61 ggctctgagg aaggtggcag ttcctacaac gggagaacca gtggttaatt tgcaaagtgg
 121 atcctgtgga ggcanncaga ggagtcccct aggccaccca gacagggctt ttagctatct
 181 gcaggccaga caccaaattt caggagggct cagtgttagg aatggattat ggcttatcaa
 241 attcacagga aactaacatg ttgaacagct tttagatttc ctgtggaaaa tataacttac
 301 taaagatgga gttcttgtga ctgactcctg atatcaagat actgggagcc aaattaaaaa
 361 tcagaaggct gcttggagag caagtccatg aaatgctctt tttcccacag tagaacctat
 421 ttccctcgtg tctcaaatac ttgcacagag gctcactccc tggataatg cagagcgagc
 481 acgatacctg gcacatacta atttgaataa aatgctgtca aattcccatt cacccattca
 541 agcagcaaac tctatctcac ctgaatgtac atgccaggca ctgtgctaga cttggctcaa
 601 aaagatttca gtttcctgga ggaaccagga gggcaaggtt tcaactcagt gctataagaa
 661 gtgttacagg ctggacacgg tggctcacgc tgtaatccc aacatttggg aggccgaggc
 721 gggcagatca caaggtcagg agatcgagac catcctggct aacatggtga accctgtct
 781 ctactaaaaa tacaaaaaat tagccgggcg ttggcggcag gtgcctgtag tcccagctgc
 841 tggggaggct gaggcaggag aatggtgtga acccgggagg cggaacttgc aggggccga
 901 gatcgtgcca ctgcactcca gctgggcga cagagtgaga ctctgtctca aaaaaaaaa
 961 aaaagtgtta tgatgcagac ctgtcaaaga ggcaaggag ggtgttccta cactccaggc
1021 actgttcata acctggactc tcattcattc tacaaatgga gggctcccct gggcagatcc
1081 ctggagcagg cactttgctg gtgtctcggt taaagagaaa ctgataactc ttggtattac
1141 caagagatag agtctcagat ggatattctt acagaaacaa tattcccact tttcagagtt
1201 caccaaaaaa tcatttagg cagagctcat ctggcattga tctggttcat ccatgagatt
1261 ggctagggta acagcacctg gtcttgcagg gttgtgtgag cttatctcca gggttgcccc
1321 aactccgtca ggagcctgaa ccctgcatac cgtatgttct ctgccccagc caagaaaggt
1381 caatttctc ctcagaggct cctgcaattg acagagagct cccgaggcag agaacagcac
1441 ccaaggtaga gacccacacc ctcaatacag acagggaggg ctattggccc ttcattgtac
1501 ccatttatcc atctgtaagt gggaagattc ctaaacttaa gtacaaagaa gtgaatgaag
1561 aaaagtatgt gcatgtataa atctgtgtgt cttccacttt gtcccacata tactaaattt
1621 aaacattctt ctaacgtggg aaaatccagt attttaatgt ggacatcaac tgcacaacga
1681 ttgtcaggaa aacaatgcat atttgcatgg tgatacattt gcaaatgtg tcatagtttg
1741 ctactccttg cccttccatg aaccagagaa ttatctcagt ttattagtcc cctcccctaa
1801 gaagcttcca ccaatactct ttccccttt cctttaactt gattgtgaaa tcaggtattc
1861 aacagagaaa tttctcagcc tcctacttct gcttttgaaa gctataaaaa cagcgaggga
1921 gaaactggca gataccaaac ctcttcgagg cacaaggcac aacaggctgc tctgggattc
1981 tcttcagcca atcttcattg tcaagtatg actttaatct tccttacaac taggtgctaa
2041 gggagtctct ctgtctctct gcctctttgt gtgtatgcat attctctctc tctctctctt
2101 tctttctctg tctctcctct ccttcctctc tgcctcctct ctcagctttt tgcaaaaatg
2161 ccaggtgtaa tataatgctt atgactcggg aaatattctg ggaatggata ctgcttatct
2221 aacagctgac accctaaagg ttagtgtcaa agcctctgct ccagctctcc tagccaatac
2281 attgctagtt ggggtttggt ttagcaaatg ctttctcta gacccaaagg acttctcttt
2341 cacacattca ttcatttact cagagatcat ttctttgcat gactgccatg cactggatgc
2401 tgagagaaat cacacatgaa cgtagccgtc atgggaagt cactcatttt ctccttttta
2461 cacaggtgtc tgaagcagcc atggcagaag tacctgagct cgccagtgaa atgatggctt
2521 attacaggtc agtggagacg ctgagccag taacatgagc aggtctcctc tttcaagagt
2581 agagtgttat ctgtgcttgg accagatt tttcccctaa attgcctctt tcagtggcaa
2641 acagggtgcc aagtaaatct gatttaaaga ctactttccc attacaagtc cctccagcct
2701 tgggacctgg aggctatcca gatgtgttgt tgcaagggct tcctgcagag gcaaatgggg
2761 agaaaagatt ccaagcccac aatacaagga atccctttgc aaagtgtggc ttggagggag
2821 agggagagct cagattttag ctgactctgc tgggctagag gttaggcctc aagatccaac
2881 agggagcacc agggtgccca cctgccaggc ctagaatctg ccttctggac tgtctgcgc
2941 atatcactgt gaaacttgcc aggtgtttca ggcagctttg agaggcaggc tgtttgcagt
3001 ttcttatgaa cagtcaagtc ttgtacacag ggaaggaaaa ataaacctgt ttagaagaca
3061 taattgagac atgtccctgt ttttattaca gtggcaatga ggatgacttg ttcctttgaag
3121 ctgatggccc taaacagatg aaggtaagac tatgggttta actcccaacc caaggaaggg
```

FIGURE 2

```
3181 ctctaacaca gggaaagctc aaagaaggga gttctgggcc actttgatgc catggtattt
3241 tgttttagaa agactttaac ctcttccagt gagacacagg ctgcaccact tgctgacctg
3301 gccacttggt catcatatca ccacagtcac tcactaacgt tggtggtggt ggccacactt
3361 ggtggtgaca ggggaggagt agtgataatg ttcccatttc atagtaggaa gacaaccaag
3421 tcttcaacat aaatttgatt atccttttaa gagatggatt cagcctatgc caatcacttg
3481 agttaaactc tgaaaccaag agatgatctt gagaactaac atatgtctac ccctttgag
3541 tagaatagtt ttttgctacc tggggtgaag cttataacaa caagacatag atgatataaa
3601 caaaaagatg aattgagact tgaaagaaaa ccattcactt gctgtttgac cttgacaagt
3661 cattttaccc gctttggacc tcatctgaaa aataaagggc tgagctggat gatctctgag
3721 attccagcat cctgcaacct ccagttctga aatattttca gttgtagcta agggcatttg
3781 ggcagcaaat ggtcattttt cagactcatc cttacaaaga gccatgttat attcctgctg
3841 tcccttctgt tttatatgat gctcagtagc cttcctaggt gcccagccat cagcctagct
3901 aggtcagttg tgcaggttgg aggcagccac ttttctctgg ctttatttta ttccagtttg
3961 tgatagcctc cctagcctc ataatccagt cctcaatctt gttaaaaaca tatttcttta
4021 gaagttttaa gactggcata acttcttggc tgcagctgtg ggaggagccc attggcttgt
4081 ctgcctggcc tttgccccc attgcctctt ccagcagctt ggctctgctc caggcaggaa
4141 attctctcct gctcaacttt cttttgtgca cttacaggtc tctttaactg tctttcaagc
4201 ctttgaacca ttatcagcct taaggcaacc tcagtgaagc cttaatacgg agcttctctg
4261 aataagagga agtggtaac atttcacaaa aagtactctc acaggatttg cagaatgcct
4321 atgagacagt gttatgaaaa aggaaaaaaa agaacagtgt agaaaattg aatacttgct
4381 gagtgagcat aggtgaatgg aaaatgttat ggtcatctgc atgaaaagc aaatcatagt
4441 gtgacagcat tagggataca aaagatata gagaaggtat acatgtatgg tgtaggtggg
4501 gcatgtacaa aagatgaca agtagaatcg ggatttattc taaagaatag cctgtaaggt
4561 gtccagaagc cacattctag tcttgagtct gcctctacct gctgtgtgcc cttgagtaca
4621 cccttaacct ccttgagctt cagagaggga taatcttttt attttatttt attttatttt
4681 gttttgtttt gttttgtttt gtttatgag acagagtctc actctgttgc ccaggctgga
4741 gtgcagtggt acaatcttgg cttactgcat cctccacctc ctgagttcaa gcgattctcc
4801 ttcctcagtc tcctgaatag ctaggattac aggtgcaccc caccacaccc agctaatttt
4861 tgtatttta gtagagaagg ggtttcgcca tgttggccag gctggttttg aagtcctgac
4921 ctaaatgatt catccacctc ggcttccaa agtgctggga ttacaggcat gagccaccac
4981 gcctggccca gagagggatg atctttagaa gctcgggatt ctttcaagcc ctttcctcct
5041 ctctgagctt tctactctct gatgtcaaag catggttcct ggcaggacca cctcaccagg
5101 ctccctccct cgctctctcc gcagtgctcc ttccaggacc tggacctctg ccctctggat
5161 ggcggcatcc agctacgaat ctccgaccac cactacagca agggcttcag gcaggccgcg
5221 tcagttgttg tggccatgga caagctgagg aagatgctgg ttccctgccc acagaccttc
5281 caggagaatg acctgagcac cttctttccc ttcatctttg aagaaggtag ttagccaaga
5341 gcaggcagta gatccacct tgtgtcctct tggaagtcat caagcccag ccaactcaat
5401 tcccccagag ccaaagccct taaaggtag aaggcccagc ggggagacaa aacaaagaag
5461 gctggaaacc aaagcaatca tctctttagt ggaaactatt cttaaagaag atcttgatgg
5521 ctactgacat ttgcaactcc ctcactcttt ctcaggggcc tttcacttac attgtcacca
5581 gaggttcgta acctccctgt gggctagtgt tatgaccatc accatttttac ctaagtagct
5641 ctgttgctcg gccacagtga gcagtaatag acctgaagct ggaacccatg tctaatagtg
5701 tcaggtccag tgttcttagc caccccactc ccagcttcat ccctactggt gttgtcatca
5761 gactttgacc gtatatgctc aggtgtcctc caagaaatca aattttgcca cctcgcctca
5821 cgaggcctgc ccttctgatt ttatacctaa acaacatgtg ctccacattt cagaacctat
5881 cttcttcgac acatgggata acgaggctta tgtgcacgat gcacctgtac gatcactgaa
5941 ctgcacgctc cgggactcac agcaaaaaag cttggtgatg tctggtccat atgaactgaa
6001 agctctccac ctccagggac aggatatgga gcaacaaggt aaatggaaac atcctggttt
6061 ccctgcctgg cctcctggca gcttgctaat tctccatgtt ttaaacaaag tagaaagtta
6121 atttaaggca aatgatcaac acaagtgaaa aaaaatatta aaaaggaata tacaaacttt
6181 ggtcctagaa atggcacatt tgattgcact ggccagtgca tttgttaaca ggagtgtgac
6241 cctgagaaat tagacggctc aagcactccc aggaccatgt ccacccaagt ctcttgggca
6301 tagtgcagtg tcaattcttc cacaatatgg ggtcatttga tggacatggc ctaactgcct
6361 gtgggttctc tcttcctgtt gttgaggctg aaacaagagt gctggagcga taatgtgtcc
6421 atcccctcc ccagtcttcc ccccttgccc caacatccgt cccacccaat gccaggtggt
6481 tccttgtagg gaaattttac cgcccagcag gaacttatat ctctccgctg taacgggcaa
6541 aagtttcaag tgcggtgaac ccatcattag ctgtggtgat ctgcctggca tcgtgccaca
```

FIGURE 2

```
6601 gtagccaaag cctctgcaca ggagtgtggg caactaaggc tgctgacttt gaaggacagc
6661 ctcactcagg gggaagctat ttgctctcag ccaggccaag aaaatcctgt ttctttggaa
6721 tcgggtagta agagtgatcc cagggcctcc aattgacact gctgtgactg aggaagatca
6781 aaatgagtgt ctctctttgg agccactttc ccagctcagc ctctcctctc ccagtttctt
6841 cccatgggct actctctgtt cctgaaacag ttctggtgcc tgatttctgg cagaagtaca
6901 gcttcacctc tttcctttcc ttccacattg atcaagttgt tccgctcctg tggatgggca
6961 cattgccagc cagtgacaca atggcttcct tccttccttc cttcagcatt taaaatgtag
7021 accctctttc attctccgtt cctactgcta tgaggctctg agaaaccctc aggcctttga
7081 ggggaaaccc taaatcaaca aaatgaccct gctattgtct gtgagaagtc aagttatcct
7141 gtgtcttagg ccaaggaacc tcactgtggg ttcccacaga ggctaccaat tacatgtatc
7201 ctactctcgg ggctaggggt tggggtgacc ctgcatgctg tgtccctaac cacaagaccc
7261 ccttctttct tcagtggtgt tctccatgtc ctttgtacaa ggagaagaaa gtaatgacaa
7321 aatacctgtg gccttgggcc tcaaggaaaa gaatctgtac ctgtcctgcg tgttgaaaga
7381 tgataagccc actctacagc tggaggtaag tgaatgctat ggaatgaagc ccttctcagc
7441 ctcctgctac cacttattcc cagacaattc accttctccc cgcccccatc cctaggaaaa
7501 gctgggaaca ggtctatttg acaagttttg cattaatgta aataaattta acataatttt
7561 taactgcgtg caaccttcaa tcctgctgca gaaaattaaa tcatttgcc gatgttatta
7621 tgtcctacca tagttacaac cccaacagat tatatattgt tagggctgct ctcatttgat
7681 agacaccttg ggaaatagat gacttaaagg gtcccattat cacgtccact ccactcccaa
7741 aatcaccacc actatcacct ccagctttct cagcaaaagc ttcatttcca agttgatgtc
7801 attctaggac cataaggaaa aatacaataa aaagcccctg gaaactaggt acttcaagaa
7861 gctctagctt aattttcacc cccccaaaaa aaaaaaattc tcacctacat tatgctcctc
7921 agcatttggc actaagtttt agaaaagaag aagggctctt ttaataatca cacagaaagt
7981 tgggggccca gttacaactc aggagtctgg ctcctgatca tgtgacctgc tcgtcagttt
8041 cctttctggc caacccaaag aacatctttc ccataggcat ctttgtccct tgccccacaa
8101 aaattcttct ttctctttcg ctgcagagtg tagatcccaa aaattaccca agaagaaga
8161 tggaaaagcg atttgtcttc aacaagatag aaatcaataa caagctggaa tttgagtctg
8221 cccagttccc caactggtac atcagcacct ctcaagcaga aaacatgccc gtcttcctgg
8281 gagggaccaa aggcggccag gatataactg acttcaccat gcaatttgtg tcttcctaaa
8341 gagagctgta cccagagagt cctgtgctga atgtggactc aatccctagg gctggcagaa
8401 agggaacaga aaggttttg agtacggcta tagcctggac tttcctgttg tctacaccaa
8461 tgcccaactg cctgccttag ggtagtgcta agaggatctc ctgtccatca gccaggacag
8521 tcagctctct cctttcaggg ccaatcccca gcccttttgt tgagccaggc ctctctcacc
8581 tctcctactc acttaaagcc cgcctgacag aaaccacggc cacatttggt tctaagaaac
8641 cctctgtcat tgctcccac attctgatga gcaaccgctt ccctatttat ttatttattt
8701 gtttgtttgt tttgattcat tggtctaatt tattcaaagg gggcaagaag tagcagtgtc
8761 tgtaaaagag cctagttttt aatagctatg gaatcaattc aatttggact ggtgtgctct
8821 ctttaaatca agtcctttaa ttaagactga aatatataa gctcagatta tttaaatggg
8881 aatatttata aatgagcaaa tatcatactg ttcaatggtt ctgaaataaa cttcactgaa
8941 gaaaaaaaaa aagggtctc tcctgatcat tgactgtctg gattgacact gacagtaagc
9001 aaacaggctg tgagagttct tggactaag ccactcctc attgctgagt gctgcaagta
9061 cctagaaata tccttggcca ccgaagacta tcctcctcac ccatcccctt tatttcgttg
9121 ttcaacagaa ggatattcag tgcacatctg gaacaggatc agctgaagca ctgcagggag
9181 tcaggactgg tagtaacagc taccatgatt tatctatcaa tgcaccaaac atctgttgag
9241 caagcgctat gtactaggag ctgggagtac agagatgaga acagtcacaa gtccctcctc
9301 agataggaga ggcagctagt tataagcaga acaaggtaac atgacaagta gagtaagata
9361 gaagaacgaa gaggagtagc caggaaggag ggaggagaac gacataagaa tcaagcctaa
9421 agggataaac agaagatttc cacacatggg ctgggccaat tgggtgtcgg ttacgcctgt
9481 aatcccagca ctttgggtgg caggggcaga aagatcgctt gagcccagga gttcaagacc
9541 agcctgggca acatagtgag actccatct ctacaaaaaa taaataaata aataaaacaa
9601 tcagccaggc atgctggcat gcacctgtag tcctagctac ttgggaagct gacactggag
9661 gattgcttga gcccagaagt tcaagactgc agtgagctta tccgttgacc tgcaggtcga
9721 c
```

FIGURE 2

Secreted IL-1RN (GEN X64532; SEQ. ID. No. 3)

```
   1 gtcgacctgc aggtcaacgg atctgagagg agagtagctt cttgtagata acagttggat
  61 tatataccat gtcctgatcc ccttcatcat ccaggagagc agaggtggtc accctgatag
 121 cagcaagcct gggggctgca gcttggtggg tagaggtact cagggataca gatgtctcca
 181 aacctgtcct gctgccttag ggagcttcta ataagttgat ggatttggtt aaaattaact
 241 tggctacttg gcaggactgg gtcagtgagg accaacaaaa agaagacatc agattatacc
 301 ctgggggttt gtatttcttg tgtttctttc tcttctttgt actaaaatat ttacccatga
 361 ctgggaaaga gcaactggag tctttgtagc attatcttag caaaaattta caagtttgg
 421 aaaacaatat tgcccatatt gtgtggtgtg tcctgtgaca ctcaggattc aagtgttggc
 481 cgaagccact aaatgtgaga tgaagccatt acaaggcagt gtgcacatct gtccacccaa
 541 gctggatgcc aacatttcac aaatagtgct tgcgtgacac aaatgcagtt ccaggaggcc
 601 caaatgaaaa tgtttgtact gaaatttgtt aaagcttccc gacaaactag atttatcagt
 661 aaggattgtt ttctgcaagg gggatgaaac ttgtggggtg agccatttgg gctgaggagg
 721 agggaggttg gagctgagaa atgtggagac aatttcactt tagaaggact gaatctccct
 781 gcctctctgg ggtgcggcag ccagcaggat ccaatggtgt atatgtctcc ccagctcccc
 841 attcagtgat atcatgtcag tagcttgaaa ttatccgtgg tgggagtatt atgtcatgga
 901 aattggcaaa tggaaacttt tattggagat tcaattgtta aactttttacc agcacaacac
 961 tgccctgcct tcagagtcaa tgaccctatc caagtttaat ccatctgtcc actgtctcca
1021 acacgatctt tataaaacac acctgacaac attaccctttt tattcagttt tttaaaagat
1081 aagtttccag ctcatcgggg tggctttaaa ggccatttct cctctggacc tcacccaact
1141 tttcaaatca cttttcctac ccctacctct aaatgctact caaactccag ccatcctgaa
1201 taataagact tttgaaaagt agattatggg ctgggcacag tggctcacac ctgtaatccc
1261 agcactttgg gaggccaaga tgggtggatc acctgaggtc gggagttcga gaccagcctg
1321 actaacatag tgaaaccctg tctctactaa aaatacaaaa ttagttgggg gtggtggcac
1381 aagcctgtaa tcccagctac tcaggaggtt gaggcagggg aattgcttga acctgggagg
1441 cggaggttgc ggtgagccta gattgctcca ctgcactcca gcctgggcaa caagagcgaa
1501 actccatctc aaaaaaataa ataaataaat aaagtagatt acatcagata cctctggcct
1561 aggttgttta tgaccaactc tcctgctgag aataactaga aaagctagac aaaacatatt
1621 tccaaaagat ctctttggag gcatcagaga atggccaagg ctgtaaggaa ctgcctgagc
1681 ccagagaggt ggagcccagc actggtgccc tttactcctg ggacatgtg ctggtttcaa
1741 aaacttcagc tgagcttttg agcattcatg gaacttggtg gggagatga aatttgtacc
1801 ttaaatcctg cctacaggga gggtccctga taatccccac ccaatttgga aatctgggtc
1861 agccttcaca ggtactgaag ccctcctctg aatgatctca gtcctgcta gggtagaggt
1921 tacctgcttt tgaaaggctc ctggcctacc tgtgcagcag gagcaaaagt gaaccatctc
1981 agggtacaga taacaatcat ccagagcctt gaatgacctc tactgtgctt aatatatagt
2041 attcagcagt cagtaaaaag gatttaggca catgcaagat gacctgtgta tcagggagaa
2101 ataggcaata aattgagatc cagcagggat ttgaatcatg gatttgaatc aggggcagcc
2161 ttcgaaagaa ctatggagaa tatactcaga tttaaaacat aagattggaa ttttttggcag
2221 agaactaaca actgtacaaa aaaggaacca aatggaaatc ctagaactga aagatgcaat
2281 taaccgatgt tgagaaatag ccaacatcta ttgaacactt cccatgtgga cagctgtgct
2341 aaacacttta caggcatcaa cataagatgt gtccccttac agcagtgcag tgtccctcct
2401 aagacatgga cagcctggtt tccctatctc tctgcttcat caaaacccct ttacgtgggg
2461 cttagacact cctgttgtct ctagtgtcta gtagcacagg gctcagcaca tggaagccac
2521 tagatacaat ttgatgacca ggacctccga tgaaagccat gggtgctgat tgggaaggca
2581 ttgtctttta tgtgctatgg tcttaaagct tcatccagga agcagaactc gggggtgct
2641 gaggacccag aaccgagaat aagattagtc agagatttcc tgtgggcaga aatcataagg
2701 acgccaactg tttgggtgag ataagacgaa accaagagtg gacttgtggc cagaagcgtg
2761 aggaagaggg agagagcttc ccttgtcccc tttcttcctc tccctaagcc acagtgattg
2821 acagcccccc cgctttggag tcagagcagg cttgagactg gactgggaaa ggagggtggg
2881 tcaggataca gagcaggaag gctgggagtg cagggcagga gcaagggct ggggcattca
2941 ttgtgcctga tctctcccac tttacctggg gtaaagaagc atatgcaaaa gccacggtgt
3001 gagtatttcc caagtgccag ggtcagggca tgattcatca cgtgcagcat ttcattcaat
3061 cctttatagta accgatgatg tggcttctat tattagctct atcagataat gaaactgaga
3121 ccaagacagg ctctgcacat tgtgtggggt aatgacacag ggggattcag acctagactc
```

FIGURE 3

```
3181 cataactcct gccccaggga ccaccccac cctcaccctg tgcatgtcga caaaggacag
3241 actgggccac ttctcaggac acagcgggga aatgacacag agcagggagg ttccaggagc
3301 cccgagcgtc ttttctccag gagaatactc tctgaattca gactggggtc agagaaacat
3361 ttacccagga gccgcagtgt gggtggggct ttttacttga aacgctgtct gaaggcagtg
3421 gcaggatgaa ctctccaccc taccttggca agccacttct cttctgcaat ctgtaaggac
3481 attgttgaga gaattatggt cttccaattc cggagggttg aagaaagaca aataggagag
3541 aacctatcat agtcaggtgc tagctgcctt ctctttcaga gagtgtgaga ataaagtgat
3601 acacttgatt attagcaaat actttggaaa ttttaaacgc taatattcaa cacactctgg
3661 aagaggcaaa taagtagaca ggttcatata catcatctcc ttcagctagt cctcacaaaa
3721 acaaacaaat gaataaacaa aattcttctt tggccctcat aggaagacac tgtttcttga
3781 acgtgtttca aaaggatgg gtgactcact caaggtcaca ctgtttatga ggacagtaca
3841 ggaatacaga catgccattt tgcctgaaaa aatccatcac ccagggaggt gacacaattt
3901 tgcagaaatg ttctatttcc tctgaaggat acattcttta aacctttggg aaattcattc
3961 atagtcttcc tcctttgaag gattactctc tggacacaaa gtgtttgatt ctgatttgtt
4021 ggttggaaga tgtgttggtt gagagaaaga ttctgatttg ttggttgaaa atagactcat
4081 caagatcaac tgctgtagta gtaaatattt tgacattttg tctgtattcc tgtgctgccc
4141 tcacaagctg catcaccttg agtgagtcat tcatactttt ttgtttgttt ttgtttttgga
4201 gatggagtct tactctgttg cctaggctgg agtgcggtgg cgtgatcttg gctcactgcg
4261 acctccatct cctgggttca agtgatcctc ctgcctcagc ctcccgagta gctgggatta
4321 caggcacatg ccaccatccc tgctaatttt tgcattttca gtagagacgg agtttcacca
4381 tgttggtcag gttggtcttg aactcctgac ctcaggtgat ccgcccacct cagcctcccc
4441 aagtgctggg attacaggtg tgagccaccg tgcccagccc agccatcatt tttgaaacac
4501 gtttgagaaa tagtgtcttc ctttgagggc caaggagaca ttttttttgt ttatttgttt
4561 gttttgtga ggactagctg aaggggggtga tgtatattaa cctgcctact tatttgcctc
4621 ttcccagagt gtgatgaata ttagggttta aagtttctga agcatttgtt aataaagccc
4681 ggggctggag gtcagaagac ctggatttct ctgcatactt tgccatcag caagctgtgt
4741 gaccttggac agatcccttt tttgtctaaa tcttctgag tcttcttgaa aacaatgcca
4801 ggttgggaca ggatgattgc caagctcccg tccagctcta aaacactgca acgtatgctt
4861 ctgcaccagc actgtccatc ctgtagatca tgcagaaatt ctcttcaact ttttcctacc
4921 cataaaatag gagcatgctt acctttttcc taatgttcca ggccccgggt ctagatattg
4981 taagtaagga agttaatgtg tatcagagcc cattatgggc cagaagttct cctcttcctt
5041 cctacacctg cttcctccct ccctccctcc ctctttccct tccttccttc catccatttg
5101 tgaagaagac atgatcaccc tcattctgag agtgaagaga cagaggctca actaatgaaa
5161 tgatttgttc aaggtcacac gggtggcaca aggcaagtgg cagaggttga atttagaccc
5221 attcctgtcc aaatgctgag tttatgtcat cgtcccgaga ccataacttt aaagatgtaa
5281 gatagtggga aaagagttga tttcaaagca cctctcagaa ggactcactt tacatcaggg
5341 gtcagcagac tcaggccaaa tccggtccat tccccgcttt tgcaaagaaa gttgtagtgg
5401 aacacagcta ggcttattga tttatggatt gccaacgtcc ttttgtgaaa cagacagctg
5461 agctgagtaa tcgtggcgca caaaacctaa aatatttact atctcgtcct ttacagaatg
5521 tttgccaatc tatggtccgg agtccaaggc tgtccatttt tcaaagaaca caaagtgaca
5581 tgagactgtc ccatgtgcag ggagccctat cattttatta tgaaaaaacg gcctttctgc
5641 tcaaatctgt ttttaaaaa gtcaacaaac agactctggg tacctgtcag aacagtagg
5701 gagtttggtt tccattgtgc tcttcttccc aggaactcaa tgaagggaa atagaaatct
5761 taattttggg gaaattgcac aggggaaaaa ggggagggaa tcagttacaa cactccattg
5821 cgacacttag tggggttgaa agtgacaaca gcaagggttt ctcttttgg aaatgcgagg
5881 agggtatttc cgcttctcgc agtggggcag ggtggcagac gcctagcttg ggtgagtgac
5941 tatttcttta taaaccacaa ctctgggccc gcaatggcag tccactgctt gctgcagtca
6001 cagaatggaa atctgcagag gcctccgcag tcacctaatc actctcctcc tcttcctgtt
6061 ccattcagag acgatctgcc gaccctctgg gagaaaatcc agcaagatgc aagccttcag
6121 gtaaggctac cccaaggagg agaagtgag ggtggatcag ctggagactg gaaacatatc
6181 acagctgcca gggctgccag gccagggggc ctgagaactg ggtttgggct ggagaggatg
6241 tccattattc aagaaagagg ctgttacatg catggcttc aggacttgtg tttcaaaata
6301 tcccagatgt ggatagtgcg accggagggc tgtcttactt tcccagagac tcaggaaccc
6361 agtgagtaat agatgcatgc caaggagtgg gactgcgatt caggcctagt tgaatgtgct
6421 gacagagaag cagagagggg caccaggggc acagcccgaa gcccagact gatatgggca
6481 aggcctgtct gtgctgacat gtcggagggt cccactctcc agggaccttg gtttccccgt
6541 ctgtgacatc tgtgacatga gagtcacgat aactccttgt gtgccttaca gggttgttgt
```

FIGURE 3

```
6601 gaaaattaaa tgcacagata atagcgtaac agtattccgt gcattgtaaa gagcctgaaa
6661 accattatga tttgaaaatg gaatcggctt tgtgagacca tcactattgt aaagatgtga
6721 tgctgataga aatgacagga ctgcttgtgc atgccctctg cagtgtgaca ttccagcagt
6781 gaaatcatgt tgggtgact tctccccac tctgaccttt atgtttgtct gggccgaggc
6841 tgcaagtcgg gctctgtggg tgtatgagtg acaagtctct cccttccaga tatggggact
6901 gtctgcttcc ctaggttgcc tctccctgct ctgatcagct agaagctcca ggagatcctc
6961 ctggaggccc cagcaggtga tgtttatccc tccagactga ggctaaatct agaaactagg
7021 ataatcacaa acaggccaat gctgccatat gcaaagcact ttggtttgcc tggccacccc
7081 tcgtcgagca tgtgggctct tcagagcacc tgatgaggtg ggtacagtta gccacacttc
7141 acaggtgaag aggtgaggca caggtcccag gtcaggctgg ccggagctct gtttattacg
7201 tctcacagct ttgagtcctg ctctcaacca gagaggccct ttaccaagaa gaaaggattg
7261 ggacccagaa tcaggtcact ggctgaggta gagaggaagc cgggttgttc ccaagggtag
7321 ctgctcctgc aggactctga gcaggtcacc agctaatgga ggaaaggctc tagggaaaga
7381 cccttctggt ctcagactca gagcgagtta gctgcaaggt gttccgtctc ttgaaacttc
7441 tacctaggtg ctatggtagc cactagtctc aggtggctat ttaaatttat acttaaatga
7501 atgaaaatag aagaaaattt aaaatccaga cccttggtca cactatccac atttaaagag
7561 gtcaatagcc acatgtggtt agtggccacc ctattgggca gtgcagctac agaacatttt
7621 tgcatcccag aaagttcttt tggatgttgc tgctctacag catgctttgc tgaaacagaa
7681 gtgccttccc tgggaatctc agatgggaag caagtaagga ggggagtcaa atgtgggctc
7741 actgctcacc agctgtgagg gttgggcctg cctcttaacc attgtcagcc tcagtcttct
7801 catccatgca tgccgtgggt atactaaaat actataccc tggaagagct ggatgcaaat
7861 ttgacaagtt ctgggggaca caggaaggtg ccaagcacaa ggctgggcac atggtggctg
7921 tgcactacag ctgagtcctt ttcctttca gaatctggga tgttaaccag aagaccttct
7981 atctgaggaa caaccaacta gttgctggat acttgcaagg accaaatgtc aatttagaag
8041 gtgagtggtt gccaggaaag ccaatgtatc tgggcatcac gtcactttgc ccgtctgtct
8101 gcagcagcat ggcctgcctg cacaaaccct aggtgcaatg tctaatcct tgtgggtct
8161 ttgtattcaa gtttgaagct gggagggcct ggctactgaa gggcacatat gagggtagcc
8221 tgaagagggt gtggagaggt agagtctagg tcagaggtca gtgcctatag gcaagtggtc
8281 ccagggccac agctgggaag ggcaaatacc agaaggcaag gttgaccatt cccttcctca
8341 agtgcctatt aaggctccat gttcctatgt tgttcaaacc ctaactcaat cccaaattaa
8401 tccaccatgt ataaggttga gctatgtctc ttattcctgg acaccatact cagccatatc
8461 tggtccacac attaacagct ggatgacctt gaagaagctt cacccactct gttcctcagc
8521 tttcccttca gtgggatgat atcaactgga caacaggatg tgcgattctt ttagttccag
8581 ccttccagga tgttttcact cccctgtttg ttgttgtagg atggtattac ctccaccttc
8641 ccaccttccc tatgccctgg ttctgtctcc tgtgcctcgc tctgaaagtg gatgagacct
8701 acaattcctg tcctggtagt tctcctaatg aacacactga agcacgagga agctgagatt
8761 tttgttgcta catgagagca tggaggcctc ttagggagag aggaggttca gagactccta
8821 ggctcctggt ggagcccac tcatggcctt gttcattttc cctgccctc agcaacactc
8881 ctattgacct ggagcacagg tatcctgggg aaagtgaggg aaatatggac atcacatgga
8941 acaacatcca ggagactcag gcctctagga gtaactgggt agtgtgcatc ctggggaaag
9001 tgagggaaat atggacatca catgaacaa catccaggag actcaggcct ctaggagtaa
9061 ctgggtagtg tgcatcctgg ggaaagtgag ggaaatatgg acatcacatg gaacaacatc
9121 caggagactc aggcctctag gagtaactgg gtagtgtgca tcctggggaa agtgagggaa
9181 atatggacat cacatggaac aacatccagg gactcaggc ctctaggagt aactgggtag
9241 tgtgcttggt ttaatcttct atttacctgc agaccaggaa gatgagacct ctctgcccctt
9301 ctgacctcgg gattttagtt ttgtggggac caggggagat agaaaaatac ccggggtctc
9361 ttcattattg ctgcttcctc ttctattaac ctgaccctcc cctctgttct tccccagaaa
9421 agatagatgt ggtacccatt gagcctcatg ctctgttctt gggaatccat ggagggaaga
9481 tgtgcctgtc ctgtgtcaag tctggtgatg agaccagact ccagctggag gtaaaaacat
9541 gctttggatc tcaaatcacc ccaaaaccca gtggcttgaa acaaccaaaa ttttttctta
9601 tgattctgtg ggttgaccag gattagctgg gtagttctgt tccatgtggt ggaacatgct
9661 ggggtcactt tggaagctgc attcagcaga gtgccaggct tgcgctgggc atccaaggtg
9721 gtccctcatc ctccaggctc tctttccatg tgatctctca gtgtttaaga gttagttgga
9781 gcttccttac agcatggcgg ctgacttcca aaagggatta ttccaaaaag agcctcaaca
9841 tgcaggcgct tattatgact tctgcttgca tcatcctatt ggccaaagcc agtcacgtgg
9901 ctaagtctag cccctgtga gaggagactg cataagagtg tgaacaccag gagacacggt
9961 cactgggggc caccactgta accatctacc acaggacctg aatctctgtg tgctactccc
```

FIGURE 3

```
10021 ttgctcaagg gccccctac ccacgcagac ctgctgtctt ctagcaaagc ccatcctcag
10081 gacctttctc ttccaatcct tattgactca aattgattag ttggtgctcc acccagagcc
10141 ctgtgctcct ttatctcatg taatgttaat gggtttccca gccctgggaa aacatggctt
10201 tgtctcaggg gcttgctgga tgcaaccta acctcaatgt gagtggccat actgtggcac
10261 tgtcccatcc ctcaccaggg acactgttct ggagggtgac tgcctgttct gtgaggagtg
10321 gggatggcta ggacattgca tggaacacac caccaccca tcttctcaga gctcaaaccc
10381 tgacagaaca ccagctccac aggccttggc ttctgctgat ggtgccgtgt atttaccaga
10441 cttagtggtc caaggccaga gtggcagatt tcccaaagtc aaggtgtgac agtgggacag
10501 cctctttgtg tctttgctgt cctaagaaac ctgggccagg ccaggcgcag tggctcacgc
10561 cttgtaatcc cagcactttg agaggccaag gtgggcagat cacgaggtca ggagtttgag
10621 accagcctgg ccaacattgg tgaaaccctg tctctattaa aaatagaaaa cattagacag
10681 gtgtggtggt gcatgcctgt aatcccagct actcaggagg ctgaggcagg agaatcgctt
10741 gaacccagga ggtggaggtt gcagtgagcc gagattgtgc cactgcactc cagcctaggc
10801 gacagagcaa gactccgtct cgggaaaatt aattaataaa taaataaacc taggtcccag
10861 agtcccacag aatggcagac aggagcacct ggggctttt agggtatggc atttcccctg
10921 tactaactct gggctgtcca gaggcgattt catggcgtgg agtggagagg gaggcagcac
10981 aggacttcct aggcctcagc tctcacctgc ccatcttttg atttccaggc agttaacatc
11041 actgacctga gcgagaacag aaagcaggac aagcgcttcg ccttcatccg ctcagacagt
11101 ggccccacca ccagttttga gtctgccgcc tgccccggtt ggttcctctg cacagcgatg
11161 gaagctgacc agcccgtcag cctcaccaat atgcctgacg aaggcgtcat ggtcaccaaa
11221 ttctacttcc aggaggacga gtagtactgc ccaggcctgc ctgttccat tcttgcatgg
11281 caaggactgc agggactgcc agtcccctg ccccagggct cccggctatg ggggcactga
11341 ggaccagcca ttgaggggtg gaccctcaga aggcgtcaca acaacctggt cacaggactc
11401 tgcctcctct tcaactgacc agcctccatg ctgcctccag aatggtcttt ctaatgtgtg
11461 aatcagagca cagcagcccc tgcacaaagc ccttccatgt cgcctctgca ttcaggatca
11521 aaccccgacc acctgcccaa cctgctctcc tcttgccact gcctcttcct ccctcattcc
11581 accttcccat gccctggatc catcaggcca cttgatgacc cccaaccaag tggctcccac
11641 accctgtttt acaaaaaaga aaagaccagt ccatgaggga ggttttaag ggtttgtgga
11701 aaatgaaaat taggatttca tgatttttt ttttcagtcc ccgtgaagga gagcccttca
11761 tttggagatt atgttcttc ggggagaggc tgaggactta aaatattcct gcatttgtga
11821 aatgatggtg aaagtaagtg gtagcttttc ccttctttt cttctttttt tgtgatgtcc
11881 caacttgtaa aaattaaaag ttatggtact atgttagccc cataatttt ttttcctttt
11941 taaaacactt ccataatctg gactcctctg tccaggcact gctgcccagc ctccaagctc
12001 catctccact ccagatttt tacagctgcc tgcagtactt tacctcctat cagaagtttc
12061 tcagctccca aggctctgag caaatgtggc tcctgggggt tctttcttcc tctgctgaag
12121 gaataaattg ctccttgaca ttgtagagct tctggcactt ggagacttgt atgaaagatg
12181 gctgtgcctc tgcctgtctc cccaccaggc tgggagctct gcagagcagg aaacatgact
12241 cgtatatgtc tcaggtccct gcagggccaa gcacctagcc tcgctcttgg caggtactca
12301 gcgaatgaat gctgtatatg ttgggtgcaa agttccctac ttcctgtgac ttcagctctg
12361 ttttacaata aaatcttgaa aatgcctata ttgttgacta tgtccttggc cttgacaggc
12421 tttgggtata gagtgctgag gaaactgaaa gaccaatgtg tyttycttac cccagaggct
12481 ggcgcctggc ctcttctctg agagttcttt tcttccttca gcctcactct ccctggataa
12541 catgagagca aatctctctg cgggg
```

FIGURE 3

Intracellular IL-1RN (GEN X77090; SEQ. ID. No. 4)

```
   1 gatcccacag ctatagttca tggtgctggg atttgaacct ctggccacca gagcccacct
  61 taatgtgtcc tcctcctgtt gtcataacag aaaagtacaa caccatgatg acacatcagg
 121 ctatcctggc aggttcccag gctgccccaa tgcccaactt tctaggttta caaagttgac
 181 atttacgaag tttccaggtt tacaaatcta gtttctgatt ctttagtcag caggaatttc
 241 tctacaaaag ctgcttcgaa aatttccagc caaaccttac acaccttggc accacatctt
 301 ggtgagccaa ggcgaagaga acaggaagtg aaggcccat gggaagtccc tgcggtcggg
 361 agcacccagg cggggcgggg ggtgggggc tttcctgtgg ccggctccct gcccctccca
 421 ccccccattca ggccctgtga gttgaatgaa gagaccctgg aatgagtcc aggtctgcag
 481 ggttagagga aattgaaggc ccttaccaga tccctgttga aagtttatg aattatgagc
 541 ccttctgcaa atgagagggt tcttccctgt caggagggac agattgtagg tggcaagatt
 601 ggtggcagcc agtaggctgg tctgctcctt cctctctatt tcatatgtgt atgaaggcat
 661 tacctgcagc aagggcctgt gtaaatgcat gtgatttaca gagcatttta tgtactgcgt
 721 gtcattcatg cttccggtga gccctaagtc taagatagg cagatagcat caggtccatt
 781 ttgcagctgt caaaatgagg tctgaagggc agaagtggtg tgcccacaca cacacaactg
 841 gttggctgca gacctgggga ctagacccgg gacttcgtcc tgcccagggg tctcttgcca
 901 ctgctcccca tcaacttgga tggctttaag catttgtgag ttgtctgctc cctgatggca
 961 gaatgcagag acatgaagct acaagcaggt tcgctcccaa cggcaaaaag gaggagggt
1021 gttcagaaca tcaggtgctt ctagagaaag cagggagaga gtatctggcc ttgtggacaa
1081 tgtcacggca gaggccaggt atagggcatg ggggtaactg gaagcgggat ggaccctctt
1141 attccctaag acatggcttc cacgtagtgc tcaaacaagg cctttgccct tgctgttccc
1201 tccacctgga atattcttcc ccttccttga cattgctcag gtctccactc ttatgtcacc
1261 ctctcagaga gggcttccct ggccactttc cctaaaatag ccacccactc ctaggtccct
1321 caaaagcata tcctgctttg gattttccct atagcaatat gccctatgaa gttattttat
1381 ttgctaactt gtttcttgtc tgttttcctt tgttagagcg ttggggacct tgtctggctt
1441 gttcccaatg cctggaagag tgcctggcac acaggattaa gccaacacat atgttttgaa
1501 tgaatgtgtg cacacatgca tgagctggcg gcagtcgggg ttggggtaag cacgaaggcc
1561 cagctcagtt ctctgcatgt gacctcccat cttacgcaga taagaaccag tttggtttct
1621 gctagcctga gtcaccctcc tggaaactgg gcctgcttgg catcaagtca gccatcagcc
1681 ggcccatctc ctcatgctgg ccaaccctct gtgagtgtgt gggaggggag gctgggctcc
1741 tccttgtact ctctgaggtg ctctggaagg aggggcagct ccaccctggg agggactgtg
1801 gcccaggtac tgcccgggtg ctactttatg ggcagcagct cagttgagtt agagtctgga
1861 agacctcaga agacctcctg tcctatgagg ccctccccat ggctttaggt aagctccttc
1921 cactctcatt ttttcacctg agaaatgaga gaggaaaatg tctacaattg gtgtttatca
1981 aatgctttca ggctctggtg agcaagcgtc caggaaaatg tcaagcgcat ggagctccag
2041 gcctgtctgg gggatctggg cacggggagg catccatggg agaccatgca ggcactctga
2101 ggcaggggct gcaagctagt gcctgctggg gcagcaggtg aacagagagg tgtaactgct
2161 gtgacagaag tc
```

FIGURE 4

METHODS OF DIAGNOSING EARLY-ONSET MENOPAUSE

CROSS REFERENCE TO RELATED APPLICATIONS

This application is a continuation-in-part of U.S. application Ser. No. 09/345,217, now U.S. Pat. No. 6,268,142, filed Jun. 30, 1999, the contents of which are specifically incorporated herein.

1. BACKGROUND OF THE INVENTION

Menopause is defined as the permanent cessation of menstruation caused by failure of ovarian follicular development in the presence of elevated gonadotrophin levels. *Comprehensive Gynecology* (eds. Mishell et al 1997). A hallmark of menopause is the decrease in ovarian follicular estrogen synthesis, although this is only one aspect of the array of physiological events that accompanies the climacteric. Symptoms accompanying menopause vary from woman to woman, but usually include some component of vasomotor instability or hot flashes, often accompanied by psychological symptoms like mood swings and irritability. The loss of estrogen predisposes to coronary artery disease. Loss of estrogen further results in loss of overall bone mineral content caused by an increased resorption of bone without a correlative increase in bone formation. Unabated net loss of bone structural integrity following menopause can culminate in clinically significant osteoporosis. The severity of these climacteric symptoms can be substantially reduced with estrogen replacement therapy. These symptoms represent formidable challenges to the health care system. Recognizing that the current average life expectancy for a woman in the U.S. is 78 years, one can readily calculate that a substantial portion of a woman's lifespan will be post-menopausal. In 1990, for example, there were more than 50 million women in the U.S. over 50 years of age.

The mean age of physiological menopause in the U.S. is between 51 and 52 years of age, with a range between 45 and 55 years old distributed along a normal curve. Stanford et al., *J. Chron. Dis* 40:995, 1987. About 10% of women in the U.S. undergo menopause before age 46; 1% of U.S. women enter menopause before age 40. If a woman becomes menopausal before age 40, the condition is termed premature ovarian failure. A variety of factors have been identified that correlate weakly with age of menopause, including number of pregnancies, use of oral contraceptives, duration of lactation, age at menarche, age at last pregnancy, race, height, weight, education or occupational history. Cassou et al., *Maturitas* 26:165–74, 1997. Cigarette smoking, however, has been observed to decrease the age of onset of menopause by about two years. Menopause may also be therapeutically induced, either chemically, surgically or via radiation (e.g. to reduce the risk of developing breast cancer associated with exposure to estrogens).

Diagnosis of menopause may be made clinically by observing the absence of menses for a year. Most women experience progressive menstrual irregularity that presages menopause. The time between the onset of menstrual irregularity and menopause is called the perimenopause. The median age at onset of perimenopause is 47.5 years; its median length is 4 years. McKinlay et al., *Maturitas* 14:103, 1992. Prior to the onset of the perimenopause, the length of the menstrual cycle tends to decrease in length, due to the decreased duration of follicular functioning. Munster et al., *Br. J. Obstet./Gynaecol.* 99:422, 1992. About 10% of women do not enter a perimenopausal phase, rather continuing to have regular cycles until menses suddenly stop.

Hormonal changes often precede changes in menstrual patterns, and early diagnosis for menopause and perimenopause has traditionally involved the measurement of follicle stimulating hormone (FSH) and luteinizing hormone (LH) levels. A significant increase in both FSH and LH levels occurs about 5 years before menopause, with the FSH increase more prominent than the LH increase. Levels of these gonadotrophins peak about one year postmenopausally for LH and two to three years after menopause for FSH. The incidence of ovulatory cycles, measured by elevated luteal phase progesterone levels, decreases from 60% during the 5–6 years before menopause to 5% in the 6 months before menopause. Estrogen levels fall as the number of ovulatory cycles decreases, particularly during the 6–12 months before menopause. FSH release, mainly controlled by inhibin, remains elevated even in the presence of post-menopausal hormone replacement. An initial fall in inhibin level is an early indication of diminishing ovarian function. FSH level rises accordingly, suggesting the woman's entry into the perimenopausal stage of reproductive function. Initial changes in FSH and inhibin are often transitory. It is therefore important to demonstrate a sustained increase in FSH. This value, combined with low estradiol levels, is used to diagnose the onset of permanent ovarian failure.

Diagnosis of menopause and perimenopause thus tends to be possible only after major changes in the endocrine system have already occurred. A younger woman without premonitory perimenopausal symptoms may have no reason to have her hormone levels measured; she may thus enter early onset menopause (EOM) without any warning. In such a patient, hormonal analysis may not yield a diagnosis until after EOM has taken place. Hormone assays in a younger patient may only be transiently abnormal prior to the onset of permanent ovarian failure. The younger patient destined for EOM is a particularly appropriate subject for early medical intervention (e.g. estrogen replacement therapy). Family planning needs to be considered if early loss of reproductive function is anticipated. Decisions about childbearing and preservation of fertilized ova should be undertaken at an early age in such a patient. Further medical advice is important about the value of hormone replacement therapy for a young woman who faces prolonged post-menopausal levels of estrogen. The relative contribution of estrogen replacement to bone strength and cardiovascular health must be balanced against the possibility of breast cancer development, in response to hormone replacement therapy (HRT).

A complex set of endocrine mechanisms regulates the female reproductive system. Understanding the interrelationship of these mechanisms provides the basis for discerning the factors involved in physiological menopause and EOM. No single organ secretes all the hormones responsible for these processes. The hypothalamus, the pituitary gland, and the ovaries, are primary organs, although adrenal and thyroid hormones also play roles. Feedback mechanisms enable the various hormones to affect the production of other hormones within the reproductive system.

The central nervous system controls reproductive hormone production through its release of gonadotropin-releasing hormone (GnRH). This hormone, produced by the hypothalamus, in turn affects gonadotropin secretion by the pituitary. GnRH secretion is responsive to levels of brain neurotransmitters, in particular the two catecholamines dopamine and norepinephrine. Opioids and prostaglandins in the hypothalamus have also been identified as regulators of GnRH release. The neurotransmitter serotonin has not been associated with GnRH release, but it does stimulate the release of prolactin by the hypothalamus. Other peptides have been identified in the brain that act as neurotransmitters. For example, the peptides activin and inhibin, members of TGF-beta superfamily, have been identified within the brain. These substances have opposite effects on pituitary gonadotropin secretion: inhibin diminishes FSH production but does not affect the release of LH; activin stimulates FSH but not LH.

GnRH, when it reaches the anterior lobe of the pituitary, stimulates the production of LH and FSH from the gonadotrophs in the pituitary gland. GnRH only acts to stimulate the production of the gonadotropic hormones. The periodic release of LH and FSH by the pituitary is responsive not only to GnRH but also to feedback systems involving the target organ of these hormones, the ovary. LH acts primarily on the thecal cells of the ovary to induce the synthesis of steroids, while FSH acts primarily on the granulosa cells of the ovary to stimulate the growth of the ovarian follicles. Both types of ovarian cells are thought to be involved in estrogen production. LH acts on the thecal cells to produce the androgens androstenedione and testosterone, which in turn are transported to the granulosa cells where they are aromatized to form the estrogens estrone and estradiol. Before puberty, FSH release is greater than LH. With the onset of the menstrual cycle, LH secretion is greater than FSH secretion. Increased levels of estradiol and inhibin during the years of menstruation act to inhibit FSH release. After menopause, FSH release again exceeds LH release.

Growth factors produced in the ovary provide means for regulating the hormonal behavior of this gland. Inhibin and activin in particular are related to FSH release. Inhibin is regulated positively by FSH levels. Inhibin preferentially affects FSH release over LH release. Levels of inhibin are observed to decrease dramatically during perimenopause, suggesting that this substance has a permissive role in the elevation of FSH before menopause. Activin is observed to stimulate FSH release. Other growth factors have been identified as having hormonal, autocrine, and paracrine effects within the ovary. *Comprehensive Gynecology* (eds. Mishell et al. 1997).

Cytokines are involved in the production of reproductive hormones via their activities within the brain and in the ovary. Interleukin-1 (IL-1) is a multifunctional cytokine implicated in a number of aspects of ovarian biology. IL-1 has been implicated in follicular development and atresia, ovulation, steroidogenesis and corpus luteum function. Terranova et al., *Am. J. Reprod. Immunol.* 37:50–63, 1997. IL-1, when found within the ovary, may be produced by immune and non-immune cells. Machelon et al., *Hum. Reprod.* 10:2198–03, 1995. IL-1 is involved in rescuing ovarian follicles from apoptosis. Kaipia et al., *Annu. Rev. Physiol.* 59:349–63, 1997. Conversely, the IL-1 receptor antagonist (IL-1RA) has been shown to block ovulation in vivo and in vitro. Tsafriri, *Adv. Exp. Med. Biol.* 377:121–40, 1995. Furthermore, IL-1 has been identified as a neurotransmitter, active in releasing norepinephrine, dopamine and serotonin, and affected by their intrahypothalamic levels. Tringali et al., *Pharmacol. Res.* 36:269–73, 1997. IL-1RA exerts a blocking effect by competitively inhibiting the binding of IL-1 to its receptors. Shintani et al., *Mol. Neurobiol.* 10:47–71, 1995. Through both central and end-organ mechanisms, cytokines and growth factors have been shown to be implicated in the regulation of reproductive endocrinology.

The age of physiological menopause is understood to have a genetic component. Cramer et al., *Fertil. Steril.* 64:740–45, 1995; Snieder et al., *J. Clin. Endocrinol. and Metab.* 83:1875–80, 1998. Because management of menopausal symptoms, prevention of post-menopausal health problems, and diagnosis of early post-menopausal illness form an important part of primary medical care, the ability to determine a genetic predisposition to EOM and to identify causative mutations would be valuable.

2. SUMMARY OF THE INVENTION

In one aspect, the present invention provides a novel method for identifying whether a woman is predisposed to developing early-onset menopause (EOM). In one embodiment, the method comprises determining whether an EOM associated allele is present in a nucleic acid sample obtained from a woman. In a preferred embodiment, the EOM associated allele is IL-1RN (+2018) allele 2 or an allele of the IL-1 (44112332) haplotype.

In certain embodiments, detection of an EOM associated allele may be accomplished directly, e.g. by analyzing the DNA, or indirectly, e.g. by analyzing the RNA or protein products of the DNA. Where the marker in question results in the translation of a mutant protein, the protein can be detected by any of a variety of protein detection methods. Such methods include immunodetection and biochemical tests, such as an activity assay, or size fractionation, where the protein has a change in apparent molecular weight either through truncation, elongation, altered folding or altered post-translational modifications.

In a preferred embodiment, the EOM associated allele can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected from anywhere in the IL-1 gene loci, either flanking the marker of interest (as required for PCR amplification) or directly overlapping the marker (as in allele-specific oligonuceotide hybridization). The DNA in the human IL-1 region has been mapped, and oligonucleotides for primers can easily be selected with a commercially available primer selection program. In a particularly preferred embodiment, the sample is hybridized with a set of primers, which hybridize 5' and 3' in a sense or antisense sequence to the EOM associated allele, and is subjected to a PCR amplification.

In another aspect, the invention features kits for performing the above-described assays. The kit can include nucleic acid sample collection means and a means for determining whether a subject carries an EOM associated allele. The kit may also comprise control samples, either negative or positive, or standards and/or an algorithmic device for assessing the results, and addition reagents and components, including DNA amplification reagents, DNA polymerases, nucleic acid purification reagents, restriction enzymes, buffers, a nucleic acid sampling device, deoxynucleotides, etc. Information obtained using the assays and kits described herein is useful for example for family planning and for treating or preventing the development of symptoms, which are associated with menopause (e.g. osteoporosis and coronary artery disease). In addition, the information can allow a more customized approach to delaying the onset of or treating the symptoms associated with EOM. For example, this information can enable a doctor to: 1) more effectively prescribe a drug that will address the molecular basis of EOM in the subject; and/or 2) better determine the appropriate dosage of a particular drug for the particular patient.

In another aspect, the invention provides in vitro and in vivo methods for identifying is biomarkers that are useful in monitoring a subject's progress towards and through menopause. In preferred embodiments, such biomarkers vary depending on a subject's IL-1 genotype. In certain embodiments, such biomarkers maybe identified by comparing said biomarkers in subjects with an EOM-associated genotype to those in subjects with a genotype not associated with EOM. In certain embodiments, biomarkers may be used to monitor a subject's progress towards and through menopause.

In another embodiment, the invention features transgenic non-human animals and their uses in identifying biomarkers that are useful in monitoring a subject's progress towards and through menopause. In yet another embodiment, the transgenic animals may be used to screen for EOM therapeutics. In a preferred variation, such animals may be used to identify agonists and antagonists of IL-1 α and/or β activity or agonists and antagonists of IL-1RA activity.

In still another aspect, the invention provides in vitro and in vivo assays for screening test substances to identify EOM therapeutics. In one embodiment, the screening assay comprises contacting a cell or subject comprising an EOM associated IL-1 allele with a test substance. One or more biomarker is observed and changes in one or more biomarker from an EOM-associated phenotype to a non-EOM-associated phenotype indicates that the test substance is likely to be effective as an EOM therapeutic. In preferred embodiments, the one or more biomarker is an IL-1 bioactivity. In yet a further aspect, the invention features methods for treating or preventing the development of early onset menopause in a woman, by administering to the woman, a pharmaceutically effective amount of an EOM therapeutic of the invention.

Other features and advantages of the invention will be apparent from the following detailed description and claims.

3. BRIEF DESCRIPTION OF THE FIGURES

FIG. 1 shows the nucleic acid sequence for IL-1A (GEN X03833; SEQ ID No. 1).

FIG. 2 shows the nucleic acid sequence for IL-1B (GEN X04500; SEQ ID No. 2).

FIG. 3 shows the nucleic acid sequence for the secreted IL-1RN (GEN X64532; SEQ ID No. 3).

FIG. 4 shows the nucleic acid sequence for the intracellular IL-1RN (GEN X77090; SEQ ID No. 4).

4. DETAILED DESCRIPTION OF THE INVENTION 4.1 Definitions

For convenience, the meaning of certain terms and phrases employed in the specification, examples, and appended claims are provided below. In addition, these terms and phrases should be understood in relation to the specification as a whole.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (+2018) allele 1, which is an allelic pattern having at least one copy of IL-1RN allele 1 at position +2018 of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN and that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1B polypeptide. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means a function that is directly or indirectly performed by an IL-1 polypeptide (whether in its native or denatured conformation), or by any subsequence thereof. These terms are also intended to encompass properties of IL-1 proteins and genes, such as expression levels and post-translational modifications. Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

The term "biomarker" refers to a phenotype of a subject or cells. Biomarkers encompass a broad range of intra- and extra-cellular events as well as whole organism physiological changes. Biomarkers may be any of these and are not necessarily involved in inflammatory responses. With respect to cells, biomarkers may be essentially any aspect of cell function, for example: levels or rate of production of signaling molecules, transcription factors, intermediate metabolites, cytokines, prostanoids, steroid hormones (e.g. estrogen, progesterone, androstenedione or testosterone), gonadotropins (e.g. LH and FSH), gene transcripts, post-translational modifications of proteins, gonadotropin releasing hormone (GnRH), catecholamines (e.g. dopamine or norepinephrine), opioids, activin, inhibin, as well as IL-1 bioactivities. Biomarkers may include whole genome analysis of transcript levels or whole proteome analysis of protein levels and/or modifications. Additionally, biomarkers may be reporter genes. For example, an IL-1 promoter or an IL-1 promoter comprising an EOM-associated allele can be operationally linked to a reporter gene. In an alternative method, the promoter can be an IL-1-regulated promoter, such as IL-8. In this manner, the activity of the reporter gene is reflective of the activity of the promoter. Suitable reporter genes include GUS, LacZ, green fluorescent protein (GFP) (and variants thereof, such as Red Fluorescent Protein, Cyan Fluorescent Protein, Yellow Fluorescent Protein and Blue Fluorescent Protein), or essentially any other gene whose product is easily detected. Other preferred biomarkers include factors involved in immune and inflammatory responses, as well as factors involved in IL-1 production and signaling, as described below. In subjects, biomarkers can be, for example, any of the above as well as electrocardiogram parameters, pulmonary function, IL-6 activities, urine parameters or tissue parameters. "EOM associated biomarkers" are any of the above which are found to correlate with EOM, or which are preferentially found in subjects or cells comprising an EOM-associated allele.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but are still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The abbreviation "EOM" as used herein refers to "early-onset menopause." The term "early-onset menopause" as used herein refers to a premature menopause, that is, onset of menopause before that time at which menopause normally occurs. The term "early-onset menopause" includes, but is not limited to, exemplary disorders such as premature ovarian failure. Premature ovarian failure refers to several disorders in which women under 40 years of age present with symptoms and signs of estrogen deficiency, and have elevated levels of the gonadotropins FSH and LH, along with low levels of estradiol. Ovarian failure may occur in association with autoimmune disorders. These disorders include but are not limited to thyroiditis, hypoparathyroidism, hypoadrenalism, diabetes mellitus, rheumatoid arthritis, myasthenia gravis, and pernicious anemia.

An "EOM associated allele" refers to an allele whose presence in a female indicates that the female is susceptible to developing early onset menopause. Examples of EOM associated alleles include allele 2 of the +2018 marker of IL-1RN (contains an Msp 1 site); allele 2 of the VNTR marker of IL-1RN (240 bp PCR product); allele 4 of the 222/223 marker of IL-1A (132 mobility units (mu) PCR product); allele 4 of the gz5/gz6 marker of IL-1A (91 mu PCR product); allele 1 of the −889 marker of IL-1A (contains an NcoI site); allele 1 of the +3954 marker of IL-1B (contains two TaqI sites); allele 2 of the −511 marker of IL-1B (contains a Bsu36I site); allele 3 of the gaat.p33330 marker (197 mu PCR product); and allele 3 of the Y31 marker (160 mu PCR product); allele 2 of the 1731 marker of the IL-1RN gene (A at position 1731); allele 2 of the 1812 marker of the IL-1RN gene (A at position 1812); allele 2 of the 1868 marker of the IL-1RN gene (G at position 1868); allele 2 of the 1887 marker of the IL-1RN gene (C at position 1887); allele 2 of the 8006 marker of the IL-1RN gene (contains an HpaII or MspI site), allele 2 of the 8061 marker of the IL-1RN gene (lacks an MwoI site) and allele 2 of the 9589 marker of the IL-1RN gene (contains an SspI site).

An "EOM causative functional mutation" refers to a mutation which causes or contributes to the development of early onset menopause in a woman. Preferred mutations occur within the IL-1 complex. Examples of EOM causative mutations include IL-1RN (+2018), which results in altered levels of IL-1 receptor antagonist An "EOM-associated phenotype" is a phenotype of subjects or cells that is associated with EOM or associated with an increased likelihood of developing EOM. An EOM-associated phenotype is also any phenotype found in a subject or cell having an EOM-associated allele, where such phenotype differs from that found in subjects or cells lacking an EOM-associated allele. Such phenotypes encompass essentially any characteristic of a biomarker. An EOM-associated phenotype may not be directly involved in EOM but may nonetheless serve as an indicator for EOM. A "non-EOM-associated phenotype" is a phenotype that is not associated with EOM or with an increased likelihood of developing EOM.

An "EOM therapeutic" refers to any agent that prevents or postpones the development or alleviates the symptoms of early onset menopause. An EOM therapeutic can be a polypeptide, peptidomimetic, nucleic acid, other inorganic or organic molecule, or a nutraceutical, preferably a "small molecule". Preferably an EOM therapeutic can modulate at least one EOM-associated phenotype. For example, an EOM therapeutic may modulate an activity of an IL-1 polypeptide, e.g., interaction with an IL-1 receptor, by mimicking or potentiating (agonizing) or inhibiting (antagonizing) the effects of a naturally-occurring IL-1 polypeptide. An IL-1 agonist can be a wild-type IL-1 protein or derivative thereof having at least one bioactivity of the wild-type IL-1, e.g. receptor binding activity. An IL-1 agonist can also be a compound that upregulates expression of an IL-1 gene or which increases at least one bioactivity of an IL-1 protein. An agonist can also be a compound which increases the interaction of an IL-1 polypeptide with another molecule, e.g, an interleukin receptor. An IL-1 antagonist can be a compound which inhibits or decreases the interaction between an IL-1 protein and another molecule, e.g., a receptor, such as an IL-1 receptor. Accordingly, a preferred antagonist is a compound which inhibits or decreases binding to an IL-1 receptor and thereby blocks subsequent activation of the IL-1 receptor. An antagonist can also be a compound that downregulates expression of an IL-1 locus gene or which reduces the amount of an IL-1 protein present. The IL-1 antagonist can be a dominant negative form of an IL-1 polypeptide, e.g., a form of an IL-1 polypeptide which is capable of interacting with a target peptide, e.g., an IL-1 receptor, but which does not promote the activation of the IL-1 receptor. The IL-1 antagonist can also be a nucleic acid encoding a dominant negative form of an IL-1 polypeptide, an IL-1 antisense nucleic acid, or a ribozyme capable of interacting specifically with an IL-1 RNA. Yet other IL-1 antagonists are molecules which bind to an IL-1 polypeptide and inhibit its action. Such molecules include peptides, e.g., forms of IL-1 target peptides which do not have biological activity, and which inhibit binding by IL-1 to IL-1 receptors. Thus, such peptides will bind the active site of IL-1 and prevent it from interacting with target peptides. e.g. an IL-1 receptor. Yet other IL-1 antagonists include antibodies interacting specifically with an epitope of an IL-1 molecule, such that binding interferes with the biological function of the IL-1 locus polypeptide. In yet another preferred embodiment, the IL-1 antagonist is a small molecule, such as a molecule capable of inhibiting the interaction between an IL-1 polypeptide and a target IL-1 receptor. Alternatively, the small molecule can function as an antagonist by interacting with sites other than the IL-1 receptor binding site. An antagonist can be any class of molecule, including a nucleic acid, protein, carbohydrate, lipid or combination thereof, but for therapeutic purposes is preferably a small molecule.

"Genotyping" refers to the analysis of an individual's genomic DNA (or a nucleic acid corresponding thereto) to identify a particular disease causing or contributing mutation or polymorphism, directly or based on detection of a mutation or polymorphism (a marker) that is in linkage disequilibrium with the disease causing or contributing gene.

A "haplotype" refers to a set of alleles that are inherited together as a group (are in linkage disequilibrium). As used herein, haplotype is defined to include those haplotypes that occur at statistically significant levels ($p_{corr} \leq 0.05$). As used herein, the phrase "an IL-1 haplotype" refers to a haplotype in the IL-1 loci. At least two IL-1 proinflammatory haplotypes are known. The IL-1 (44112332) haplotype is associated with decreased IL-receptor antagonist activity, whereas the IL-1 (33441461) haplotype is associated with increased IL-1 α and β agonist activity. The IL-1 (44112332) haplotype includes the following alleles: IL-1RN (+2018) allele 2; IL-1RN (VNTR) allele 2; IL-1A (222/223) allele 4; IL-1A (gz5/gz6) allele 4; IL-1A (−889) allele 1; IL-1B (+3954) allele 1; IL-1B (−511) allele 2; gaat.p33330 allele 3; Y31 allele 3; IL-1RN exon lic (1812) allele 2; IL-1RN exon lic (1868) allele 2; IL-1RN exon lic (1887) allele 2; Pic (1731) allele 2; IL-1A (+4845) allele 1; IL-1B (+6912) allele 1; and IL-1B (−31) allele 2.

"IL-1 gene cluster" and "IL-1 loci" as used herein include all the nucleic acid at or near the 2q13 region of chromosome 2, including at least the IL-1A, IL-1B and IL-1RN genes and any other linked sequences. The terms "IL-1", "IL-1B", and "IL-1RN" as used herein refer to the genes coding for IL-1α, IL-1β, and IL-1 receptor antagonist or IL-1ra, respectively. The DNA in this region has been mapped. Nicklin et al., *Genomics* 19:382–84, 1994; Nothwang H. G., et al., *Genomics* 41:370, 1997; Clark, et al., *Nucl. Acids. Res.* 14:7897–914, 1986, (erratum at *Nucleic Acids Res.* 15:868, 1987. The gene accession numbers (GEN) for IL-1A and IL-1B, are X03833 and X04500, respectively. In general, references to nucleotide positions for IL-1RN refer to the nucleotide sequence in GFN X64532, which is the secreted form of the protein, unless there is some indication, either expressly indicated or implied from the context, that the intracellular form, which has GEN X77090, is being referenced. The two forms of IL-1RA are encoded by a single gene by alternative use of two first exons. See generally Lennard et al., *Crit. Rev. Immuno.* 15:77–105, 1995.

"IL-1 functional mutation" refers to a mutation within the IL-1 gene cluster that results in an altered phenotype (i.e. affects the function of an IL-1 gene or protein). Examples include: IL-1A (+4845) allele 1, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X, wherein X is IL-1A, B, or RN or some other gene in the IL-1 gene loci, and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a thymine (T) at position +2018 of the sense strand. Clay et al., *Hum. Genet.* 97:723–26, 1996. "IL-1RN (+2018) allele 2" refers to a form of the IL-1RN gene which contains a cytosine (C) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand.

Where the term "IL-1" is used in reference to a gene product or polypeptide, it is meant to refer to all gene products encoded by the interleukin-1 locus on human chromosome 2 (2q 12–14) and their corresponding homologs from other species or functional variants thereof. The term IL-1 thus includes secreted polypeptides which promote an inflammatory response, such as IL-1α and IL-1β, as well as a secreted polypeptide which antagonizes inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin. A "knock-out" transgenic animal refers to an animal in which there is partial or complete suppression of the expression of an endogenous gene (e.g., based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. As used herein, the term "linkage disequilibrium" also refers to linked sequences. Alleles that co-occur at expected frequencies are said to be in "linkage equilibrium" or "not linked." When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are >97% in linkage disequilibrium with the two most frequent alleles of IL-1RN (VNTR), which are allele and allele 2.

The term "marker" refers to a sequence in the genome that is known to vary among individuals. For example, the IL-1RN gene has a marker that consists of a variable number of tandem repeats (VNTR). The different sequence variants at a given marker are called alleles, mutations or polymorphisms. For example, the VNTR marker has at least five different alleles, three of which are rare. Different alleles could have a single base change, including substitution, insertion or deletion, or could have a change that affects multiple bases, including substitutions, insertions, deletions, repeats, inversions and combinations thereof.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any members of the class Mammalian, except for humans.

The term "nucleic acid" refers to polynucleotides or oligonucleotides such as deoxyribonucleic acid (DNA), and, where appropriate, ribonucleic acid (RNA). Nucleic acids may be full length genes or portions thereof that are useful, for example, as primers or as probes. The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

"Nutraceuticals" are defined as substances comprising vitamins, minerals, proteins, amino acids, sugars, phytoestrogens, flavonoids, phenolics, anthocyanins, carotenoids, polymers of the above, and mixtures of the above.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region." As used herein, the term "polymorphic region" includes, without limitation, a polymorphic site consisting of a single nucleotide, e.g., a single nucleotide polymorphism (SNP). A specific genetic sequence at a polymorphic region is an allele. A polymorphic region can be a single nucleotide, the identity of which differs in different alleles. A polymorphic region can also be more than one nucleotide long, and possibly significantly longer in length.

The term "propensity" as used herein in reference to a condition or disease state, as in "propensity" for a condition or disease, is used interchangeably with the expressions "susceptibility" or "predisposition" to a condition or disease. For example, the term "propensity" is used in reference to certain polymorphic alleles which are hereby discovered to be associated with a given condition or disease state. They are thus over-represented in individuals with a condition or disease as compared with healthy individuals. Therefore, the presence of such alleles indicates that an individual is at increased risk for the future development of a condition or disease, and the absence of such alleles indicates that the individual is not at increased risk for the condition or disease.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

A "test substance" can comprise essentially any element, chemical compound (including a nucleic acid, protein, peptide, carbohydrate or lipid) or mixture thereof, including a nutraceutical or small molecule drug.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain lieterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the IL-1 polypeptides, e.g. either agonistic or antagonistic forms. However, transgenic animals in which the recombinant IL-1 gene is silent are also contemplated, as for example, the FLP or CRE recombinase dependent constructs described below. Moreover, "transgenic animal" also includes those recombinant animals in which gene disruption of one or more IL-1 genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 Predictive Medicine 4.2.1. IL-1 Linked Polymorphisms Associated with EOM

The invention is based, at least in part, on the identification of an allele (IL-1RN (+2018) allele 2), that is associated with early onset menopause (EOM) in women. Because this allele is in linkage disequilibrium with other alleles in the IL-1 region, the detection of such other alleles can also indicate a predisposition to developing EOM in a woman. For example, IL-1RN (+2018) allele 2, also referred to as exon 2 (8006) (GenBank:X64532 at 8006) polymorphism, Clay et al., *Hum. Genet.* 97:723–26, 1996, is in linkage disequilibrium with IL-1RN (VNTR) allele 2, which is a member of the IL-1 (44112332) human haplotype. Cox et al., *Am. J. Human Genet.* 62:1180–88, 1998; International Patent Application No. PCT/GB98/01481. Further, the following alleles of the IL-1 (44112332) proinflammatory haplotype are known to be in linkage disequilibrium with IL-1RN (+2018): allele 4 of the 222/223 marker of IL-1A (a dinucleotide repeat polymorphism (HUGO GDB: 190869); allele 4 of the gz5/gz6 marker of IL-1A (a trinucleotide repeat polymorphism (HUGO GDB: 177384; Zuliani et al., *Am. J. Hum. Genet.* 46:963–69, 1990); allele 1 of the −889 marker of IL-1A (a single base variation marker-HUGO GDB: 210902; McDowell et al., *Arthritis and Rheumatism* 38:221–28, 1995); allele 1 of the +3954 marker of IL-1B (a single base C/T variation; di Giovine et al., *Cytokine* 7:606 (1995); Pociot et al. *Eur J. Clin. Invest.* 22:396–402, 1992); allele 2 of the −511 marker of IL-1B; allele 3 of the gaat.p33330 marker; allele 3 of the Y31 marker, IL-1A (+4825) allele 2, IL-1B (+6912) allele 1, and IL-1B (−31) allele 2.

Three other polymorphisms in an IL-1RN alternative exon (Exon lic, which produces an intracellular form of the gene product, GEN X77090) are in linkage disequilibrium with IL-1RN (+2018) allele 2. These include: the IL-1RN exon lic (1812) polymorphism (GenBank:X77090 at 1812); the IL-1RN exon lic (1868) polymorphism (GenBank:X77090 at 1868); and the IL-1RN exon lic (1887) polymorphism (GenBank:X77090 at 1887). Yet another polymorphism in the promoter for the alternatively spliced intracellular form of the gene, the Pic (1731) polymorphism (GenBank:X77090 at 1731), is also in linkage disequilibrium with IL-1RN (+2018) allele 2. The corresponding sequence alterations for each of these IL-1RN polymorphic loci is shown below.

| Allele No. | Exon 2 (+2018 of IL-1RN) | Exon 1ic-1 (1812 of GB: X77090) | Exon 1ic-2 (1868 of GB: X77090) | Exon 1ic-3 (1887 of GB:X77090) | Pic (1731 of GB: X77090) |
|---|---|---|---|---|---|
| 1 | T | G | A | G | G |
| 2 | C | A | G | C | A |

Clay et al., *Hum. Genet.* 97:723–26, 1996. For each of these polymorphic loci, the allele 2 sequence variant has been determined to be in linkage disequilibrium with IL-1RN (+2018) allele 2.

In addition to the allelic patterns described above, one of skill in the art can readily identify other alleles (including polymorphisms and mutations) that are in linkage disequilibrium with IL-1RN (+2018) allele 2, and are thereby associated with EOM. For example, a nucleic acid sample from a first group of women without EOM can be collected, as well as DNA from a second group of women with EOM. The nucleic acid sample can then be compared to identify those alleles that are over-represented in the second group as compared with the first group, wherein such alleles are presumably associated with EOM. Alternatively, alleles that are in linkage disequilibrium with an EOM associated allele can be identified, for example, by genotyping a large population and performing statistical analyses to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic crossover events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci can be relied upon as an indicator of inheritance of a linked disease-causing mutation. For example, menopause occurring before age 46 is 6 times more likely to occur in women with family histories of early menopause, especially in families where a first-degree relative entered menopause before age 40. Torgerson et al., Eur. J. Obstet. Gynec. Reprod. Biol. 74:63–66, 1997.

Appropriate probes may be designed to hybridize to a specific region of the IL-1 locus, such as IL-1A, IL-1B or IL-1RN. These genomic DNA sequences are shown in FIGS. 1–4, respectively, and further correspond to formal SEQ ID Nos. 1–4, respectively. Alternatively, these probes may incorporate other regions of the IL-1 genomic locus, including intergenic sequences. Indeed this region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/human/index.html)). From such sources SNPs as well as other human polymorphisms occurring in the region of the IL-1 locus on human chromosome 2, region q12–13 may be found.

For example, examination of this region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFM087xa1 at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGC-CCACCCTTTAGAGC (SEQ ID No. 5) and a 3' primer of the sequence TGGCCTCCAGAAACCTCCAA (SEQ ID No. 6). Furthermore, one allele of AFM087xa1 generates a 177 bp PCR amplification product with a 5' primer of the sequence GCTGATATTCTGGTGGGAAA (SEQ ID No. 7) and a 3' primer of the sequence GGCAAGAG-CAAAACTCTGTC (SEQ ID No. 8). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\# \text{ of A or T})+4\times(\# \text{ of G or C})]$.

A number of other human polymorphic loci occur between these two CA dinucleotide repeat polymorphisms and provide additional targets for determination of an EOM prognostic allele in a family or other group of genetically related individuals. For example, the National Center for Biotechnology Information web site (www.ncbi.nlm.nih.gov/genemap/) lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch between the probe and the template or target strand.

4.2.2 EOM Causative Functional Mutations

An EOM causative functional mutation occurring within an IL-1 gene (e.g. IL-1A, IL-1B or IL-1RN) or a gene locus, which is linked thereto may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) Eur. J. Immunol. 23: 124045). These repeat sequences contain three potential binding sites for transcriptional factors: an SP1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased repeat number at this polymorphic IL-1A locus leads to decreased IL-1α synthesis (Bailly et al. (1996) Mol Immunol 33: 999–1006).

Alternatively, a mutation can result in a hyperactive gene product. For example, allele 2 of the IL-1B (C at +6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene (G at +6912). Further, an IL-1B (−511) mutation occurs near a promoter binding site for a negative glucocorticoid response element (Zhang et al. (1997) DNA Cell Biol 16: 145–52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

4.2.3. Detection of Alleles

Many methods are available for detecting specific alleles at human polymorphic loci. The preferred method for detecting a specific polymorphic allele may depend, in part, upon the molecular nature of the polymorphism. For example, the preferred method of detection used for a single nucleotide polymorphism may differ from that employed for a VNTR polymorphism.

By way of general introduction, detection of specific alleles may be nucleic acid techniques based on hybridization, size, or sequence, such as restriction fragment length polymorphism (RFLP), nucleic acid sequencing, and allele specific oligonucleotide (ASO) hybridization. In one embodiment, the methods comprise detecting in a sample DNA obtained from a woman the existence of an allele associated with EOM. For example, a nucleic acid composition comprising a nucleic acid probe including a region of nucleotide sequence which is capable of hybridizing to a sense or antisense sequence to an allele associated with EOM can be used as follows: the nucleic acid in a sample is rendered accessible for hybridization, the probe is contacted with the nucleic acid of the sample, and the hybridization of the probe to the sample nucleic acid is detected. Such technique can be used to detect alterations or allelic variants at either the genomic or mRNA level as well as to determine tnRNA transcript levels, when appropriate.

In another exemplary embodiment, an allele associated with EOM at a VNTR polymorphism, such as IL-1RN (VNTR) allele 2, may be determined. For example, the number of tandem repeats of the IL-1RN (VNTR) polymorphic site maybe determined by amplifying the nucleic acid to be analyzed, and determining the identity of the allele of that site by analyzing the size of said amplification product.

A preferred detection method is ASO hybridization using probes overlapping an allele associated with EOM and has about 5, 10, 20, 25, or 30 nucleotides around the mutation or polymorphic region. In a preferred embodiment of the invention, several probes capable of hybridizing specifically to other allelic variants involved in EOM are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al., *Human Mutation* 7:244, 1996. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., *Proc. Natl. Acad. Sci. USA* 87:1874–78, 1990), transcriptional amplification system (Kwoh, D. Y. et al., *Proc. Natl. Acad. Sci. USA* 86:1173–77, 1989), and Q-Beta Replicase (Lizardi, P. M. et al., *Bio/Technology* 6:1197, 1988).

Amplification products may be assayed in a variety of ways, including size analysis, restriction digestion followed by size analysis, detecting specific tagged oligonucleotide primers in the reaction products, ASO hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that have detectable labels that are different and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an allele associated with EOM, such as IL-1RN (+2018) allele 2, under conditions such that hybridization and amplification of the desired marker occurs, and (iv) detecting the amplification product. These detection schemes are especially useful for the detection of nucleic acid molecules if such molecules are present in very low numbers.

An allele associated with EOM can also be identified by alterations in restriction enzyme cleavage patterns through RFLP analysis. For example, sample and control DNA is isolated, amplified (optionally), digested with one or more restriction endonucleases, and fragment length sizes are determined by gel electrophoresis through size fractionization.

In yet another embodiment, any of a variety of sequencing reactions known in the art can be used to directly sequence a polymorphic site having at least one allele associated with EOM. Exemplary sequencing reactions include those based on techniques developed by Maxim and Gilbert (*Proc. Natl. Acad. Sci. USA* 74:560, 1977) or Sanger (Sanger et al., *Proc. Nat. Acad. Sci. USA* 74:5463, 1977). It is also contemplated that any of a variety of automated sequencing procedures may be utilized when performing the subject assays (*Biotechniques* 19:448, 1995), including sequencing by mass spectrometry (see, for example PCT publication WO 94/16101; Cohen et al., *Adv. Chromatogr.* 36:127–62, 1996; and Griffin et al., *Appl. Biochem. Biotechnol.* 38:147–59, 1993). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers et al., *Science* 230:1242, 1985). In general, the art technique of "mismatch cleavage" starts by providing heteroduplexes formed by hybridizing (labelled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (See, for example, Cotton et al., *Proc. Natl. Acad. Sci. USA* 85:4397, 1988; Saleeba et al., *Methods Enzymol.* 217:286–95, 1992) In a preferred embodiment, the control DNA or RNA can have a detectable label.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al., *Carcinogenesis* 15:1657–62, 1994). According to an exemplary embodiment, a probe based on IL-1RN (+2018) allele 2 is hybridized to a cDNA or other DNA product from a test cell(s). The duplex is treated with a DNA mismatch repair enzyme, and the cleavage products, if any, can be detected from electrophoresis protocols or the like. (See, for example, U.S. Pat. No. 5,459,039.)

In other embodiments, alterations in electrophoretic mobility will be used to identify an allele associated with EOM. For example, single strand conformation polymorphism (SSCP) may be used to detect differences in electrophoretic mobility between mutant and wild type nucleic acids (Orita et al., *Proc. Natl. Acad. Sci. USA* 86:2766, 1989, see also Cotton, *Mutat. Res.* 285:125–44, 1993; and Hayashi, *Genet. Anal. Tech. Appl.* 9:73–79, 1992. Single-stranded DNA fragments of sample and control are denatured and allowed to renature. The secondary structure of single-stranded nucleic acids varies according to sequence, the resulting alteration in electrophoretic mobility enables the detection of even a single base change. The DNA fragments may be labeled or detected with labeled probes, such as primers with a detectable label. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., *Trends Genet.* 7:5, 1991).

In yet another embodiment, the movement of an allele associated with EOM in polyacrylamide gels containing a gradient of denaturant is assayed using denaturing gradient gel electrophoresis (DGGE) (Myers et al., *Nature* 313:495, 1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner, *Biophys. Chem.* 265:12753, 1987).

Examples of other techniques for detecting alleles associated with EOM include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al., *Nature* 324:163, 1986); Saiki et al., *Proc. Natl. Acad. Sci. USA* 86:6230, 1989). Such ASO hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al., *Nucleic Acids Res.* 17:2437–2448, 1989) or at the extreme 3' end of one primer where, under appropriate conditions, mismatch can prevent, or reduce polymerase extension (Prossner, *Tibtech* 11:238, 1993. In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci USA* 88:189, 1991). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren et al., *Science* 241:1077–80, 1988. The OLA protocol uses two oligonucleotides which are designed to be capable of hybridizing to abutting sequences of a single strand of a target. One of the oligonucleotides is linked to a separation marker, e.g., biotinylated, and the other has a detectable label. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al., *Proc. Natl. Acad. Sci. USA* 87:8923–27, 1990. In this method, PCR is used to achieve the exponential amplification of target DNA, which is then detected using OLA.

Several techniques based on this OLA method have been developed and can be used to detect alleles associated with EOM. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al., *Nucleic Acids Res.* 24:3728, 1996, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Several methods have been developed to facilitate analysis of single nucleotide polymorphisms. In one embodiment, the single base polymorphism can be detected by using a specialized exonuclease-resistant nucleotide, as disclosed, e.g., in U.S. Pat. No. 4,656,127 (Mundy et al.). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. French Patent 2,650,840; PCT Appln. No. WO91/02087. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet et al. in PCT Appln. No. 92/15712. The method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al., French Patent 2,650,840 and PCT Appln. No. WO91/02087, the method of Goelet et al. is preferably a heterogeneous phase assay, in which the primer or the target molecule is immobilized to a solid phase.

Recently, several primer-guided nucleotide incorporation procedures for assaying polymorphic sites in DNA have been described (Komher et al., *Nucleic Acids Res.* 17:7779–84, 1989; Sokolov, *Nucleic Acids Res.* 18:3671, 1990; Syvanen et al., *Genomics* 8:684–92, 1990; Kuppuswamy et al., *Proc. Natl. Acad. Sci. USA* 88:1143–47, 1991; Prezant et al., *Hum. Mutat.* 1:159–64, 1992; Ugozzoli et al., *GATA* 9:107–12, 1992; Nyren et al., *Anal. Biochem.* 208:171–75, 1993). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, et al., *Amer. J. Hum. Genet.* 52:4659, 1993).

For mutations that produce premature termination of protein translation, the protein truncation test (PTT) offers an efficient diagnostic approach (Roest et. al., *Hum. Mol. Genet.* 2:1719–21, 1993; van der Luijt et. al., *Genomics* 20:1–4, 1994). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon. In still another method known as Dynamic Allele Specific Hybridization (DASH), a target sequence is amplified by PCR in which one primer is biotinylated. The biotinylated product strand is bound to a streptavidin or avidin coated microtiter plate well, and the non-biotinylated strand is rinsed away with alkali. An oligonucleotide probe, specific for one allele, is hybridized to the target at low temperature. This forms a duplex DNA region that interacts with a double strand-specific intercalating dye. Upon excitation, the dye emits fluorescence proportional to the amount of double stranded DNA (probe-target duplex) present. The sample is then steadily heated while fluorescence is continually monitored. A rapid fall in fluorescence indicates the denaturing (or "melting") temperature of the probe-target duplex. When performed under appropriate buffer and dye conditions, a single-base mismatch between the probe and the target results in a dramatic lowering of melting termperature (Tm) that can be easilty detected (Howell, W. M. et al., (1999) *Nature Biotechnology* 17:)87–88.

Any cell type or tissue may be utilized in the diagnostics described herein. In a preferred embodiment the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express at least one gene of the IL-1 loci.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR in situ Hybridization: Protocols and Applications (Raven Press, NY, 1992)).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Another embodiment of the invention is directed to kits for detecting a propensity to EOM in a woman. This kit may contain one or more oligonucleotides, including 5' and 3' oligonucleotides that hybridize 5' and 3' to a polymorphic site having as allele associated with EOM, such as the +2018 marker, or detection oligonucleotides that hybridize directly to an allele associate with EOM. The kit may also contain one or more oligonucleotides capable of hybridizing near or at other alleles of the IL-1 gene cluster. PCR amplification oligonucleotides should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ oligonucleotides having detectable labels to allow ease of identification in the assays. Examples of labels which may be employed include radio-labels, enzymes, fluorescent compounds, streptavidin, avidin, biotin, magnetic moieties, metal binding moieties, antigen or antibody moieties, and the like. Oligonucleotides useful in kits as well as other aspects of the present invention are selected from the group consisting of any oligonucleotides that overlap or are contained in any of the following sequences:

| | |
|---|---|
| 5' CTC AGC AAC ACT CCT AT 3' | (SEQ ID No. 9) |
| 5' TCC TGG TCT GCA GGT AA 3' | (SEQ D No. 10) |
| 5' CTA TCT GAG GAA CAA CCA ACT AGT AGC 3' | (SEQ ID No. 11) |
| 5' TAG GAC ATT GCA CCT AGG GTT TGT 3' | (SEQ ID No. 12) |
| 5' CTC AGG TGT CCT CGA AGA AAT CAA A 3' | (SEQ ID No. 13) |
| 5' GCT TTT TTG CTG TGA GTC CCG 3' | (SEQ ID No. 14) |
| 5' AAG CTT GTT CTA CCA CCT GAA CTA GGC 3' | (SEQ ID No. 15) |
| 5' TTA CAT ATG AGC CTT CCA TG 3' | (SEQ ID No. 16) |
| 5' TGG CAT TGA TCT GGT TCA TC 3' | (SEQ ID No. 17) |
| 5' GTT TAG GAA TCT TCC CAC TT 3' | (SEQ ID No. 18) |
| 5' ATG GTT TTA GAA ATC ATC AAG CCT AGG GCA 3' | (SEQ ID No. 19) |
| 5' AAT GAA AGG AGG GGA GGA TGA CAG AAA TGT 3' | (SEQ ID No. 20) |
| 5' TTACGCAGATAAGAACCAGTTTGG 3' | (SEQ ID No. 21) |
| 5' TTTCCTGGACGCTTGCTCACCAG 3' | (SEQ ID No. 22) |
| 5' ATGTATAGAATTCCATTCCTG 3' | (SEQ ID No. 23) |
| 5' TAAAATCAAGTGTTGATGTAG 3' | (SEQ ID No. 24) |
| 5' GGGATTACAGGCGTGAGCCACCGCG 3' | (SEQ ID No. 25) |
| 5' TTAGTATTGCTGGTAGTATTCATAT 3' | (SEQ ID No. 26) |
| 5' GAGGCGTGAGAATCTCAAGA 3' | (SEQ ID No. 27) |
| 5' GTGTCCTCAAGTGGATCTGG 3' | (SEQ ID No. 28) |
| 5' GGGCAACAGAGCAATGTTTCT 3' | (SEQ ID No. 29) |
| 5' CAGTGTGTCAGTGTACTGTT 3' | (SEQ ID No. 30) |

One of skill in the art can readily determine additional useful oligonucleotide sequences based on the IL-1 gene sequences provided herein.

The kit may, optionally, also include DNA sampling means such as the AmpliCard™ (University of Sheffield, Sheffield, England S10 2JF; Tarlow, et al., *J. of Invest. Dermatol.* 103:387–389, 1994) and the like; DNA purification reagents such as Nucleon™ kits, lysis buffers, proteinase solutions and the like; PCR reagents, such as 10× reaction buffers, thermostable polymerase, dNTPs, and the like; and DNA detection means such as appropriate restriction enzymes, allele specific oligonucleotides, degenerate oligonucleotide primers for nested PCR, and the like.

4.3 EOM Therapeutics and Pharmacogenomics 4.3.1 Pharmacogenomics

The ability to rapidly genotype patients promises to fundamentally change the testing and development of therapeutic or disease-preventative substances. Currently, the effectiveness of a substance for treating or preventing a disease is assessed by testing it on a pool of patients. While many variables in the patient pool are controlled for, the effects of genetic variability are not typically tested. Consequently, a drug may be found to be statistically ineffective when examined in a genetically diverse pool of patients and yet be highly effective for a select group of patients with particular genetic characteristics. Unless patients are separated by genotype, many drugs with great promise for selected populations are likely to be rejected as useless for the population as a whole.

Knowledge of particular alleles associated with EOM, alone or in conjunction with information on other genetic defects contributing to EOM (the genetic profile of EOM) allows a customization of the therapy to the individual's genetic profile, the goal of "pharmacogenomics". For example, as shown herein, women having an allele associated with EOM, such as IL-1RN (+2018) allele 2 are predisposed to EOM. Thus, comparison of a woman's IL-1 profile to the population profile for the disease, permits the selection or design of drugs that are expected to be safe and efficacious for a particular patient or patient population (i.e., a group of patients having the same genetic alteration).

The ability to target populations expected to show the highest clinical benefit, based on the IL-1 gene profile or the genetic profile of EOM, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since measuring the effect of various doses of an agent on an EOM causative mutation is useful for optimizing effective dose).

4.3.2 IL-1 Production and Molecular Signaling Pathways

To better understand likely targets for therapeutic intervention and likely EOM biomarkers, it is necessary to understand general mechanisms for IL-1 signaling and production. IL-1 is part of a complex web of inter- and intra-cellular signaling events. Many proteins are involved in the inflammatory response and also in immune responses more generally. A partial list includes the interleukins, TNF, NF-κB, the immunoglobulins, clotting factors, lipoxygenases, as well as attendant receptors, antagonists and processing enzymes for the above.

The IL-1 polypeptides, IL-1α and IL-1β, are abundantly produced by activated macrophages that have been stimulated with bacterial lipopolysaccharide (LPS), TNF, IL-1 itself, other macrophage-derived cytokines, or contact with CD4$^+$ T cells. The IL-1 promoter contains several regulatory elements including a cAMP responsive element, an AP-1 binding site and an NP-κB binding site. Both and AP-1 (Jun and Fos) must be activated and translocated to the nucleus in order to regulate transcription. NF-κB is normally retained in the cytoplasm through binding with IκB. The NF-κB-IκB complex is disrupted by phosphorylation of IκB. IκB phosphorylation can be regulated by signaling from cell-surface receptors via activation of mitogen-activated protein kinase (MAP linse) pathways and other kinase pathways. Jun and Fos are also substrates for regulatory kinases, such as JNK, in the case of Jun.

The IL-1A and B transcripts are translated into pro-proteins by a process that may also be regulated by MAP kinase pathways. Inhibitors of MAP kinase phosphorylation such as trebufelone decrease translation of IL-1 transcripts. The IL-1 α and β precursor proteins require myristoylation for localization to the membrane and conversion to mature IL-1 by the Interleukin Converting Enzyme (ICE). Other extracellular proteases may also play a minor role in IL-1 maturation, including trypsin, elastase, chymotrypsin and mast cell chymase. ICE can be inhibited by several agents including the eICE isoform, antibodies to the ICE α, β and γ isoforms, the cow pox-produced Crm-A protein and an endogenous tetrapeptide competitive inhibitor.

Mature IL-1α and IL-1β have similar activities and interact with the same receptors. The primary receptor for these factors is the type I IL-1 receptor. The active signaling complex consists of the IL-1 ligand, the type I receptor and the IL-1 receptor accessory protein. A type II receptor, as well as soluble forms of the type I and type II receptors appear to act as decoy receptors to compete for bioavailable IL-1. In addition, a natural inhibitor of IL-1 signaling, IL-1 receptor antagonist, is produced by monocytes. IL-1ra is also produced by hepatocytes and is a major component of the acute phase proteins produced in the liver and secreted into the circulation to regulate immune and inflammatory responses.

The IL-1 signaling complex activates several intracellular signal transduction pathways, including the activities of NF- and AP-1 described above. In signaling, IL-1 influences the activity of a host of factors including: PI-3 kinase, phospholipase A2, protein kinase C, the JNK pathway, 5-lipoxygenase, cyclooxygenase 2, p38 MAP kinase, p42/44 MAP kinase, p54 MAP kinase, Rac, Ras, TRAF-6, TRAF-2 and many others. IL-1 also affects expression of a large number of genes including: members of the IL-1 gene cluster, TNF, other interleukin genes (2, 3, 6, 8, 12, 2R, 3R and 5R), TGF-β, fibrinogen, matrix metalloprotease 1, collagen, elastase, leukemia inhibiting factor, IFN α, β, γ, COX-2, inducible nitric oxide synthase, metallothioneins, and many more.

4.3.3 EOM Associated Biomarkers

In addition to having genetic tests for EOM, it would be desirable to have tests for monitoring a subject's progression towards EOM. In other words, certain biomarkers may be indicative of the timing of early onset of menopause. It would be desirable to be able to identify these biomarkers and monitor them to provide information about the onset of menopause. It is particularly desirable to find biomarkers that are tailored to the subject's genotype.

In a preferred embodiment, biomarkers likely to be associated with EOM can be identified by using subjects or cells comprising differing IL-1 genotypes. A set of biomarkers can be examined in a subject or cell having an EOM-associated allele, such as IL-1RN (+2018) allele 2 or another allele of the IL-1 (44112332) haplotype. The same set of biomarkers can be examined in another subject or cell not having an EOM-associated allele. Biomarkers that show a difference dependent upon the IL-1 genotype are likely to be useful for predicting the early onset of menopause. These differences constitute EOM-associated phenotypes.

The association between certain biomarkers and EOM can be further established by performing trials wherein certain biomarkers are measured in a population of subjects of various ages, some of which may have entered menopause. Optionally, multiple measurements may be done over time as subjects age. Preferably, the presence or absence of EOM-associated alleles is determined in the subjects. Standard statistical methods may be used to determine the correlation between certain biomarkers and the early onset of menopause.

Measurements of EOM-associated biomarkers may be used as an indicator of a subject's current risk of developing EOM or as an indicator of progression towards or through menopause.

With respect to cells, biomarkers may be essentially any aspect of cell function, for example: levels or rate of production of signaling molecules, transcription factors, intermediate metabolites, cytokines, prostanoids, steroid hormones (e.g. estrogen, progesterone, androstenedione or testosterone), gonadotropins (e.g. LH and FSH), gene transcripts, post-translational modifications of proteins, gonadotropin releasing hormone (GnRH), catecholamines (e.g. dopamine or norepinephrine), opioids, activin, inhibin, as well as IL-1 bioactivities. Biomarkers may include whole genome analysis of transcript levels or whole proteome analysis of protein levels and/or modifications. Additionally, biomarkers may be reporter genes. For example, an IL-1 promoter or an IL-1 promoter comprising an EOM-associated allele can be operationally linked to a reporter gene. In an alternative method, the promoter can be an IL-1-regulated promoter, such as IL-8. In this manner, the activity of the reporter gene is reflective of the activity of the promoter. Suitable reporter genes include GUS, LacZ, green fluorescent protein (GFP) (and variants thereof, such as RFP, CFP, YFP and BFP), or essentially any other gene that is easily detected. In subjects, biomarkers can be, for example, any of the above as well as electrocardiogram parameters, pulmonary function, IL-6 activities, urine parameters or tissue parameters. Other preferred biomarkers include factors involved in immune and inflammatory responses, as well as factors involved in IL-1 production and signaling, as described above.

4.3.4 EOM Therapeutics

An EOM therapeutic can comprise any type of compound, including a protein, peptide, peptidomimetic, small molecule, nucleic acid, or nutraceutical. In preferred embodiments, an EOM therapeutic is a modulator of a factor involved in IL-1 production or signaling. In a particularly preferred embodiment, an EOM therapeutic is a modulator of IL-1 bioactivity (e.g. IL-1α, IL-1β or an IL-1 receptor agonist or antagonist). Preferred agonists include nucleic acids (e.g. encoding an IL-1 protein or a gene that is up- or down-regulated by an IL-1 protein), protein (e.g. IL-1 proteins or a protein that is up-or down-regulated by an IL-1 protein) or a small molecule (e.g. that regulates expression of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules or nutraceuticals that act to suppress or inhibit IL-1 to transcription and/or IL-1 activity.

4.3.5. In Vivo and Cell-based Screening Assays

Based on the identification of IL-1 mutations that cause or contribute to EOM, the invention further features in vivo and cell-based assays, e.g., for identifying EOM therapeutics. In one embodiment, a cell having an EOM-associated allele is contacted with a test compound and at least one biomarker is measured. If at least one biomarker changes such that the phenotype of the cell now more closely resembles that of a cell that does not have an EOM-associated allele, then the test substance is likely to be effective as an EOM therapeutic.

As an illustrative example, suppose that an IL-1 allele associated with EOM causes cells having that allele to overproduce an IL-1 polypeptide. Levels of the IL-1 polypeptide are used as a biomarker in this case. Treatment with a test substance causes the cells to produce the IL-1 polypeptide at a lower level, more closely resembling IL-1 polypeptide production in a cell that does not have an EOM-associated allele. Accordingly, the test substance is likely to be effective as an EOM therapeutic. In this manner, test substances with allele-specific effects may be identified. The specificity of the compound vis a vis the IL-1 signaling pathway can, if desired, be confirmed by various control analysis, e.g., measuring the expression of one or more control genes. In particular, this assay can be used to determine the efficacy of IL-1 antisense, ribozyme and triplex compounds.

In another variation a cell is contacted with a test compound and an IL-1 protein and the interaction between the test compound and the IL-1 receptor or between the IL-1 protein (preferably a tagged IL-1 protein) and the IL-1 receptor is detected, e.g., by using a microphysiometer (McConnell et al. (1992) Science 257:1906). An interaction between the IL-1 receptor and either the test compound or the IL-1 protein is detected by the microphysiometer as a change in the acidification of the medium. This assay system thus provides a means of identifying molecular antagonists which for example, function by interfering with IL-1 protein-IL-1 receptor interactions, as well as molecular agonist which, for example, function by activating an IL-1 receptor.

Essentially any culturable cell type can be used for the cell-based assays. In particular, cells may be immune cells such as monocytes, macrophages or thymocytes, or other cell types such as fibroblasts or cells derived from female reproductive organs. Preferably cells will express an IL-1 receptor.

In another variation, a subject having an EOM-associated allele is contacted with a test compound and at least one biomarker is measured. If at least one biomarker changes such that the phenotype of the cell now more closely resembles that of a cell that does not have an EOM-associated allele, then the test substance is likely to be effective as an EOM therapeutic. The subject may be a human or a transgenic non-human animal.

In preferred embodiments, cellular or in vivo assays are used to identify compounds which modulate expression of an IL-1 gene, modulate translation of an IL-1 mRNA, or which modulate the stability or activity of an IL-1 mRNA or protein. Accordingly, in one embodiment, a cell which is capable of producing IL-1 protein is incubated with a test compound and the amount of IL-1 protein produced in the cell medium is measured and compared to that produced from a cell which has not been contacted with the test compound. In another variation, an IL-1 bioactivity is measured and compared to the bioactivity measured in a cell which has not been contacted with a test compound. Additionally, the effects of test substances on different cells containing various IL-1 alleles maybe compared.

4.3.6 Cell-free Assays

Cell-free assays can also be used to identify compounds which are capable of interacting with an IL-1 protein, to thereby modify the activity of the IL-1 protein. Such a compound can, e.g., modify the structure of an IL-1 protein thereby affecting its ability to bind to an IL-1 receptor. In a preferred embodiment, cell-free assays for identifying such compounds consist essentially in a reaction mixture containing an IL-1 protein and a test compound or a library of test compounds in the presence or absence of a binding partner. A test compound can be, e.g., a derivative of an IL-1 binding partner, e.g., a biologically inactive target peptide, or a small molecule.

Accordingly, one exemplary screening assay of the present invention includes the steps of contacting an IL-1 protein or functional fragment thereof with a test compound or library of test compounds and detecting the formation of complexes. For detection purposes, the molecule can be labeled with a specific marker and the test compound or library of test compounds labeled with a different marker. Interaction of a test compound with an IL-1 protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the IL-1β protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 protein, (ii) an IL-1 receptor, and (iii) a test compound; and (b) detecting interaction of the IL-1 protein and IL-1 receptor. A statistically significant change (potentiation or inhibition) in the interaction of the IL-1 protein and IL-1 receptor in the presence of the test compound, relative to the interaction in the absence of the test compound, indicates a potential antagonist (inhibitor) of IL-1 bioactivity for the test compound. The compounds of this assay can be contacted simultaneously. Alternatively, an IL-1 protein can first be contacted with a test compound for an appropriate amount of time, following which the IL-1β receptor is added to the reaction mixture. The efficacy of the compound can be assessed by generating dose response curves from data obtained using various concentrations of the test compound. Moreover, a control assay can also be performed to provide a baseline for comparison.

Complex formation between an IL-1 protein and IL-1 receptor may be detected by a variety of techniques. Modulation of the formation of complexes can be quantitated using, for example, detectably labeled proteins such as radiolabeled, fluorescently labeled, or enzymatically labeled IL-1 protein or IL-1 receptors, by immunoassay, or by chromatographic detection.

Typically, it will be desirable to immobilize either IL-1 protein or the IL-1 receptor to facilitate separation of complexes from uncomplexed forms of one or both of the proteins, as well as to accommodate automation of the assay. Binding of IL-1 protein and IL-1 receptor can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/ IL-1β (GST/IL-1β) fusion proteins can be adsorbed onto glutathione sepharose beads (Sigma Chemical, St. Louis, Mo.) or glutathione derivatized microtitre plates, which are then combined with the IL-1 receptor, e.g. an $^{35}$S-labeled IL-1 receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of IL-1 protein or IL-1 receptor found in the bead fraction quantitated from the gel using standard electrophoretic techniques such as described in the appended examples. Other techniques for immobilizing proteins on matrices are also available for use in the subject assay. For instance, either IL-1 protein or IL-1 receptor can be immobilized utilizing conjugation of biotin and streptavidin.

4.3.7 Transgenic animals

As described above, transgenic animals can be made for example, to assist in screening for EOM therapeutics. Transgenic animals of the invention can include non-human animals containing an IL-1 mutation, which is causative of EOM in humans, under the control of an appropriate IL-1 promoter or under the control of a heterologous promoter. Transgenic animals of the invention can also include an IL-1 gene expressed at such a level as to create an EOM phenotype. To compare the effects of different IL-1 alleles, transgenic animals may be generated with a variety of IL-1 alleles and differences in EOM phenotype can be identified. By testing different alleles and different expression levels, an animal with an EOM phenotype optimal for testing candidate drugs can be generated and identified.

The transgenic animals can also be animals containing a transgene, such as reporter gene, under the control of an IL-1 promoter or fragment thereof. These animals are useful, e.g., for identifying drugs that modulate production of an IL-1, such as by modulating gene expression. In certain variations, the IL-1 allele may be a promoter mutation. In this case it is particularly desirable to operationally fuse the altered promoter to a suitable reporter gene.

Methods for obtaining transgenic non-human animals are well known in the art. In preferred embodiments, the expression of the EOM causative mutation is restricted to specific subsets of cells, tissues or developmental stages utilizing, for example, cis-acting sequences that control expression in the desired pattern. In the present invention, such mosaic expression of an IL-1 protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the IL-1 mutation in certain spatial patterns. Moreover, temporal patterns of expression can be provided by, for example, conditional recombination systems or prokaryotic transcriptional regulatory sequences. Genetic techniques, which allow for the expression of IL-1 mutation can be regulated via site-specific genetic manipulation in vivo, are known to those skilled in the art.

The transgenic animals of the present invention all include within a plurality of their cells an EOM causative mutation transgene of the present invention, which transgene alters the phenotype of the "host cell". In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abrermski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the EOM causative mutation transgene can be regulated via control of recombinase expression.

Use of the cre/loxP recombinase system to regulate expression of an EOM causative mutationa transgene requires the construction of a transgenic animal containing transgenes encoding both the Cre recombinase and the subject protein. Animals containing both the Cre recombinase and the EOM causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-2$^b$, H-2$^d$ or H-2$^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–4152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.4 Methods of Treatment 4.4.1. Effective Dose

The treatment of an individual with a particular therapeutic can be monitored by monitoring a biomarker known to be affected by the therapeutic. In particular, such biomarkers may include IL-1 protein (e.g. IL-1α, IL-1β, IL-1RA), mRNA and/or IL-1 bioactivity. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level of expression of an IL-1 protein, mRNA or bioactivity in the preadministration sample; (iii) obtaining one or more post-administration samples from the subject; (iv) detecting the level of expression or activity of the IL-1 protein, mRNA or bioactivity in the post-administration sample; (v) comparing the level of expression or activity of the IL-1 protein, mRNA or bioactivity in the preadministration sample with the corresponding IL-1 protein, mRNA or bioactivity in the postadministration sample, respectively; and (vi) altering the administration of the agent to the subject accordingly.

Cells of a subject may also be obtained before and after administration of a therapeutic to detect the level of expression of genes other than IL-1, to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.4.2. Formulation and Use

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa.

For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodilluoromethane, trichlorofluoromethane, dichlorotetrafluoroetlane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possiblity of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For traismucosal or transdermal administration, penetrants appropriate to the barrier to be permeated are used in the formulation. Such penetrants are generally known in the art and include, for example, for transmucosal administration bile salts and fuisidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. Nos. 4,683,195; 4,683,202; Nucleic Acid Hybridization (B. D. Hames & S. J. Higgins eds., 1984); U.S. Pat. Nos. 4,666,828; 5,192,659; 5,272,057; and 4,801,531.

EXAMPLES

Determining an Individual's Allelic Pattern (Genotyping)

1. IL-1RN (+2018); IL-1RN (VNTR); IL-1A (−889); IL-1B (+3954); IL-1B (−511); and IL-1A (+4845)

Sections 1.1 to 1.4 set forth general procedures that apply to Sections 1.5 to 1.10 unless otherwise indicated.

1.1 Preparation of DNA.

Blood is taken by venepuncture and stored uncoagulated at −20° C. prior to DNA extraction. Ten milliliters of blood are added to 40 ml of hypotonic red blood cell (RBC) lysis solution (10 mM Tris, 0.32 Sucrose, 4 mM $MgCl_2$, 1% Triton X-100) and mixed by inversion for 4 minutes at room temperature (RT). Samples are then centrifuged at 1300 g for 15 minutes, the supernatant aspirated and discarded, and another 30 ml of RBC lysis solution added to the cell pellet. Following centrifugation, the pellet is resuspended in 2 ml white blood cell (WBC) lysis solution (0.4 M Tris, 60 mM EDTA, 0.15 M NaCl, 10% SDS) and transferred into a fresh 15 ml polypropylene tube. Sodium perchlorate is added at a final concentration of 1 M and the tubes are first inverted on a rotary mixer for 15 minutes at RT, then incubated at 65° C. for 25 minutes, being inverted periodically. After addition of 2 ml of chloroform (stored at −20° C.), samples are mixed for 10 minutes at room temperature and then centrifuged at 800 g for 3 minutes. At this stage a very clear distinction of phases can be obtained using 300 µl Nucleon Silica suspension (Scotlab, UK) and centrifugation at 1400 G for 5 minutes. The resulting aqueous upper layer is transferred to a fresh 15 ml polypropylene tube and cold ethanol (stored at −20° C.) is added to precipitate the DNA. This is spooled out on a glass hook and transferred to a 1.5 ml eppendorf tube containing 500 µl TE or sterile water. Following overnight resuspension in TE, genomic DNA yield is calculated by spectrophotometry at 260 nm. Aliquots of samples are diluted at 100 ug/ml, transferred to microtiter containers and stored at 4° C. Stocks are stored at −20° C. for future reference.

1.2 Polymerase Chain Reaction.

Oligonucleotide primers designed to amplify the relevant region of the gene spanning the polymorphic site (as detailed below) are synthesised, resuspended in Tris-EDTA buffer (TE), and stored at −20° C. as stock solutions of 200 uM. Aliquots of working solutions (1:1 mixture of forward and reverse, 20 uM of each in water) are prepared in advance.

Typically PCR reaction mixtures are prepared as detailed below.

|  | Stock Concentration | Volume | Final Concentration |
|---|---|---|---|
| Sterile H2O |  | 29.5 µl |  |
| 10 × PCR buffer | 200 mM Tris-HCl (pH 8.4) | 5.00 µl | 20 mM Tris-HCl, |
| MgCl2 | 50 mM | 1.75 µl | 1.75 mM |
| dNTP | mix 10 mM of each | 4.00 µl | 0.2 mM of each |
| primer forward | 20 µM | 2.5 µl | 1 µM |
| prime reverse | 20 µM | 2.5 µl | 1 µM |
| Taq polymerase | 5 U/µl | 0.25 µl | 1.25 units/50 µl |
| Detergent (eg W-1, Gibco) | 1% | 2.5 µl | 0.05% |
| Template | 200 ng/µl | 2.00 µl | 2 ng/µl |
| Final Volume |  | 50.00 µl |  |

DNA template is dotted at the bottom of 0.2 ml tubes or microwells. The same volume of water or negative control DNA is also randomly tested. A master-mix (including all reagents except templates) is prepared and added to the wells or tubes, and samples are transferred to the thermocycler for PCR.

PCR can be performed in 0.5 ml tubes, 0.2 ml tubes or microwells, according to the thermocycler available. The reaction mixture is overlaid with mineral oil if a heated lid (to prevent evaporation) is not available.

1.3 Restriction Enzyme Digestion.

A master mix of restriction enzyme buffer and enzyme is prepared and aliquotted in suitable volumes in fresh microwells. Digestion is carried out with an oil overlay or capped microtubes at the appropriate temperature for the enzyme on a dry block.

Restriction buffer dilutions are calculated on the whole reaction volume (i.e. ignoring salt concentrations of PCR buffer). Restriction enzymes are used 3–5 times in excess of the recommended concentration, to compensate for the unfavourable buffer conditions and to ensure complete digestion.

1.4 Electrophoresis.

Polyacrylamide-gel electrophoresis (PAGE) of 20–40 µl PCR sample is carried out in Tris-Borate-EDTA buffer and at constant voltage. Depending on the size discrimination need, different PAGE conditions are used (9 to 12% acrylamide, 1.5 mm×200) and different DNA size marker (øX174-Hae III or øX 174-Hinf 1). A 2% agarose horizontal gel can be used for genotyping the IL-1RN (VNTR) marker.

1.5 IL-1RN (+2018).

The genotypes for the women in this Example were determined for the +2018 marker. PCR primers were designed (mismatched to the genomic sequence) to engineer two enzyme cutting sites on the two alleles to allow for RFLP analysis. The gene accesion number is X64532. Oligonucleotide primers used were:

5' CTATCTGAGGAACAACCAACTAGTAGC 3'  (SEQ ID No. 7)

5' TAGGACATTGCACCTAGGGTTTGT 3'  (SEQ ID No. 8)

Cycling was performed at [96°, 1 min]; [94°, 1 min; 57°, 1 min; 70°, 2 min;]×35; [70°, 5 min]×1; 4° C. Each PCR reaction was divided in two 25 ul aliquots: to one was added 5 Units of Alu 1, to the other 5 Units of Msp 1, in addition to 3 ul of the specific 10×restriction buffer. Incubation is at 37° C. overnight. Electrophoresis was by PAGE 9%.

The two enzymes cut respectively the two different alleles. Alu 1 will produce 126 and 28 bp fragments for allele 1, while it does not digest allele 2 (154 bp). Msp 1 will produce 125 and 29 bp with allele 2, while allele 1 is uncut (154 bp). Hence the two reactions (separated side by side in PAGE) will give inverted patterns of digestion for homozygote women, and identical patterns in heterozygotes. Allelic frequencies are 0.74 and 0.26.

1.6 IL-1RN (VNTR).

The IL-1N (VNTR) marker may be genotyped in accordance with the following procedure. As indicated above, the two alleles of the IL-1RN (+2018) marker are >97% in linkage disequilibrium with the two most frequent alleles of IL-1RN (VNTR), which are allele 1 and allele 2. The gene accession number is X64532. The oligonucleotide primers used for PCR amplification are:

5' CTCAGCAACACTCCTAT 3'  (SEQ ID No. 5)

5' TCCTGGTCTGCAGGTAA 3'  (SEQ ID No. 6)

Cycling is performed at [96°, 1 min]×1; [94°, 1 min; 60°, 1 min; 70°, 2 min]×35; [70°, 5 min]×1; 4° C. Electrophoresis is conducted in 2% agarose at 90V for 30 min.

The PCR product sizes are direct indication of number of repeats: the most frequent allele (allele 1) yields a 412 bp product. As the flanking regions extend for 66 bp, the remaining 344 bp imply four 86 bp repeats. Similarly, a 240 bp product indicates 2 repeats (allele 2), 326 is for 3 repeats (allele 3), 498 is 5 (allele 4), 584 is 6 (allele 6). Frequencies for the four most frequent alleles are 0.734, 0.241, 0.021 and 0.004.

1.7 IL-1A (−889).

The ILIA (−889) marker may be genotyped in accordance with the following procedure. McDowell et al., *Arthritis Rheum.* 38:221–28, 1995. One of the PCR primers has a base change to create an Nco I site when amplifying allele 1 (C at −889) to allow for RFLP analysis. The gene accession number is X03833. The oligonucleotide primers used for PCR amplification are:

| | |
|---|---|
| 5' AAG CTT GTT CTA CCA CCT GAA CTA GGC 3' | (SEQ ID No. 11) |
| 5' TTA CAT ATG AGC CTT CCA TG 3' | (SEQ ID No. 12) |

MgCl$_2$ is used at 1 mM final concentration, and PCR primers are used at 0.8 µM. Cycling is performed at [96°, 1 min]×1; [94°, 1 min; 50°, 1 min; 72°, 2 min]×45; [72°, 5 min]×1; 4° C. To each PCR reaction is added 6 Units of Nco I in addition to 3 µl of the specific 10×restriction buffer. Incubation is at 37° overnight. Electrophoresis is conducted by 6% PAGE.

Nco I digest will produce fragments 83 and 16 bp in length, whereas the restriction enzyme does not cut allele 2. Correspondingly, heterozygotes will have three bands. Frequencies for the two alleles are 0.71 and 0.29.

1.8 IL-1A (+4845).

The IL-1A (+4845) marker may be genotyped in accordance with the following procedure. The PCR primers create an Fnu 4H1 restriction site in allele 1 to allow for RFLP analysis. The gene accession number is X03833. The oligonucleotide primers used for PCR amplification are:

| | |
|---|---|
| 5' ATG GTT TTA GAA ATC ATC AAG CCT AGG GCA 3' | (SEQ ID No. 15) |
| 5' AAT GAA AGG AGG GGA GGA TGA CAG AAA TGT 3' | (SEQ ID No. 16) |

MgCl$_2$ is used at 1 mM final concentration, and PCR primers are used at 0.8 µM. DMSO is added at 5% and DNA template is at 150 ng/50 µl PCR. Cycling is performed at [95°, 1 min]×1; [94°, 1 min; 56°, 1 min; 72°, 2 min]×35; [72°, 5 min]×1, 4° C. To each PCR reaction is added 2.5 Units of Fnu 4H1 in addition to 2 µl of the specific 10×restriction buffer. Incubation is at 37° overnight. Electrophoresis is conducted by 9% PAGE.

Fnu 4H1 digest will produce a constant band of 76 bp(present regardless of the allele), and two further bands of 29 and 124 bp for allele 1, and a single further band of 153 bp for allele 2. Frequencies for the two alleles are 0.71 and 0.29.

1.9 IL-1B (−511).

The IL-1B (−511) marker nay be genotyped in accordance with the following procedure. The gene accession number is X04500. The oligonucleotide primers used for PCR amplification are:

| | |
|---|---|
| 5' TGG CAT TGA TCT GGT TCA TC 3' | (SEQ ID No. 13) |
| 5' GTT TAG GAA TCT TCC CAC TT 3' | (SEQ ID No. 14) |

MgCl$_2$ is used at 2.5 mM final concentration, and PCR primers are used at 1 µM. PCR Cycling is performed at [95°, 1 min]×1; [95°, 1 min; 53°, 1 min; 72°, 1 min]×35; [72°, 5 min]×1; 4° C. Each PCR reaction is divided into two aliquots: to one aliquot is added 3 Units of Ava I, to the other aliquot is added 3.7 Units of BSU 36I. To both aliquots is added 3 µl of the specific 10×restriction buffer. Incubation is at 37° overnight. Electrophoresis is conducted by 9% PAGE.

Each of the two restriction enzymes cuts one of the two alleles, which allows for RFLP analysis. Ava I will produce two fragments of 190 and 114 bp with allele 1, and it does not cut allele 2 (304 bp). BSU 36I will produce two fragments of 190 and 11 base pairs with allele 2, and it does not cut allele 1 (304 bp). Frequencies for the two alleles are 0.61 and 0.39.

1.10 IL-1B (+3954).

The IL-1B (+3954) marker may be genotyped in accordance with the following procedure. The gene accession number is X04500. The oligonucleotide primers used for PCR amplification are:

| | |
|---|---|
| 5' CTC AGG TGT CCT CGA AGA AAT CAA A 3' | (SEQ ID No. 9) |
| 5' GCT TTT TTG CTG TGA GTC CCG 3' | (SEQ ID No. 10) |

MgCl$_2$ is used at 2.5 mM final concentration, and DNA template at 150 ng/50 µl PCR. Cycling is performed at [95°, 2 min]×1; [95°, 1 min; 67.5°, 1 min; 72°, 1 min]×35; [72°, 5 min]×1; 4° C. To each PCR reaction is added 10 Units of Taq I (Promega) in addition to 3 µl of the specific 10×restriction buffer. Incubation is at 65° overnight. Electrophoresis is conducted by 9% PAGE.

The restriction enzyme digest produces a constant band of 12 bp and either two further bands of 85 and 97 bp corresponding to allele 1, or a single band of 182 bp corresponding to allele 2. Frequencies for the two alleles are 0.82 and 0.18.

2. IL-1A (2221223); IL-1A (gz5/gz6); gaat.p33330; and Y31

Genotyping of these markers could proceed as described in Cox et al., *Am. J. Human Genet.* 62:1180–88, 1998. PCRs for these markers may be carried out by using fluorescently labeled forward primers (Cruachem) in a 10 µl reaction volume containing 50 mM KCL, 10 mM Tris-HCl, pH 9.0, 1.5 mM MgCl$_2$, 200 µM dNTPs, 25 ng of each primer, 50 ng DNA, 0.004% W-1 (Gibco-BRI), and 0.2 units Taq polymerase. The PCR conditions could be 94° for 1 min., 55° for 1 min., and 72° for 1 min. for 30 cycles. One unit PERFECT MATCH (Stratagene) would be added to gz5/gz6 PCRs. The primer sequences could be as follows: for IL-1A (222/223):

| | |
|---|---|
| 5' ATGTATAGAATTCCATTCCTG 3' | (SEQ ID No. 19) |
| 5' TAAAATCAAGTGTTGATGTAG 3' | (SEQ ID No. 20) |

For IL-1A (gz5/gz6):

| | |
|---|---|
| 5' GGGATTACAGGCGTGAGCCACCGCG 3' | (SEQ ID No. 21) |
| 5' TTAGTATTGCTGGTAGTATTCATAT 3' | (SEQ ID No. 22) |

For gaat.p33330:

| | |
|---|---|
| 5' GAGGCGTGAGAATCTCAAGA 3' | (SEQ ID No. 23) |
| 5' GTGTCCTCAAGTGGATCTGG 3' | (SEQ ID No. 24) |

For Y31:

| | |
|---|---|
| 5' GGGCAACAGAGCAATGTTCT 3' | (SEQ ID No. 25) |
| 5' CAGTGTGTCAGTGTACTGTT 3' | (SEQ ID No. 26) |

A sample of PCR product could be examined by agarose-gel electrophoresis, and the remainder of the PCR products could be pooled according to the intensity of the ethidium-bromide staining. Two microliters of the pool could be analyzed on an automated sequencer, and allele sizes could be determined against the appropriate size standard.

3 IL-1RN exon lic (1812); IL-1RN exon lic (1868); IL-1RN exon lic (1887); Pic (1731)

Genotyping of these markers could proceed as described in Clay et al., *Hum. Genet.* 97:723–26, 1996. PCRs could be performed using 5 μg genomic DNA in a final reaction volume of 250 μl containing 250 pmol forward and reverse primers and 1.5 mM MgCl$_2$. The annealing temperature could be 57°. Primers for exon 1ic PCR and sequencing could be:

| | |
|---|---|
| 5' TTACGCAGATAAGAACCAGTTMGG 3' | (SEQ ID No. 17) |
| 5' TTTCCTGGACGCTTGCTCACCAG 3' | (SEQ ID No. 18) |

The resulting product would be 426 bp, and the forward primer could be biotinylated to allow for ready sequencing.

2. IL-1N (+2018) allele 2 is associated with EOM

Applicants investigated the relationship between age of onset of menopause and specific polymorphism in the IL-1RN gene in two study populations, one in the UK and one in the USA.

The polymorphism at position (+2018) in the IL-1RN gene was amplified by PCR techniques and analyzed by the TaqMan® technique, using primers and probes described above (SEQ ID NOs.7 and 8).

The UK study population consisted of 140 postmenopausal Caucasian women (mean age 64.8 years, range 51.1 to 84.2). The mean age of onset of menopause was 49.3 years. Age of menopause was stratified by carriage of allele 2 of IL-1RN (+2018). Statistical analysis indicated that carriage of allele 2 of IL-1RN (+2018) resulted in an earlier onset of menopause by 1.03+/−0.47 (p=0.03) years per copy of allele 2.

The US study population was broken into two groups, those of Northern European descent and those of non-Northern European descent. To determine ancestry, subjects were asked the following question: "Which of the following best describes your ethnic origin or familys original nationality? Please mark no more than two." A subject was considered of Northern European descent if the subject selected any one or two of the following ethnic origins: Canadian (except French Canadian), English, Irish, Scandinavian, Scottish or Welsh.

313 women of Northern European descent were examined. Age of menopause was again stratified by carriage of allele 2 of IL-1RN (+2018). Statistical analysis indicated that carriage of allele 2 of IL-1RN (+2018) resulted in an earlier onset of menopause by 0.96+/−0.42 (p=0.02) years per copy of allele 2.

226 women of non-Northern European descent were also analyzed. Age of menopause was stratified by carriage of allele 2 of IL-1RN (+2018). Statistical analysis indicated that carriage of allele 2 of IL-1RN (+2018) resulted in a later onset of menopause by 1.16+/−0.54 (p=0.03) years per copy of allele 2.

The ancestry of subjects was ascertained by asking subjects to indicate the most appropriate category of ancestry. Subjects were instructed to indicate their ancestry as Northern European if they felt that their ancestry could best be traced to England, Scotland, Wales, Ireland and/or Scandinavia.

Polymorphisms in the IL-1RN gene at position (+2018) and at other sites in disequilibrium with IL-1RN (+2018) are associated with timing and onset of menopause. The relationship may differ among different ethnic groups.

Summary Table: Onset of Menopause and IL-1RN (+2018) allele 2

| Study Group: | UK: Caucasian | US: Northern European Ancestry | US: Non-Northern European Ancestry |
|---|---|---|---|
| Number of Subjects | 140 | 313 | 266 |
| Change in onset of menopause per IL-1RN (+2018) allele 2 | −1.03 +/− 0.47 P = 0.03 | −0.96 +/− 0.42 P = 0.02 | +1.16 +/− 0.54 P = 0.03 |

The specification and examples should be considered exemplary only with the true scope and spirit of the invention suggested by the following claims.

---

What is claimed is:

1. A method for determining the predisposition of a subject of Northern European ancestry to early-onset menopause, comprising detecting in said subject IL-1RN (+2018) allele 2, wherein detection of an IL-1RN (+2018) allele 2 in a said subject is predictive of a predispositon to early-onset menopause.

2. The method of claim 1, wherein detecting said allele comprises allele specific oligonucleotide hybridization.

3. The method of claim 1, wherein detecting said allele comprises RFLP analysis.

4. The method of claim 1, wherein detecting said allele comprises amplification of a nucleic acid.

5. The method of claim 4, wherein said amplification comprises PCR.

6. The method of claim 4, wherein said amplification comprises using a first oligonucleotide that overlaps a sec ond oligonucleotide, or a complement thereof, selected from the group consisting of:

5' CTA TCT GAG GAA CAA CCA ACT AGT AC 3' (SEQ ID NO:7); and

5' TAG GAC ATT GCA CCT AGG GTT TGT 3' (SEQ ID NO:8).

7. The method of claim 6, wherein said first oligonucleotide comprises at least ten nucleotides of said second oligonucleotide.

* * * * *

SEQUENCE LISTING

<160> NUMBER OF SEQ ID NOS: 30

<210> SEQ ID NO 1
<211> LENGTH: 11970
<212> TYPE: DNA
<213> ORGANISM: Homo sapiens

<400> SEQUENCE: 1

```
aagcttctac cctagtctgg tgctacactt acattgctta catccaagtg tggttatttc      60
tgtggctcct gttataacta ttatagcacc aggtctatga ccaggagaat tagactggca     120
ttaaatcaga ataagagatt ttgcacctgc aatagacctt atgacaccta accaacccca     180
ttatttacaa ttaaacagga acagagggaa tactttatcc aactcacaca agctgttttc     240
ctcccagatc catgcttttt tgcgtttatt atttttttaga gatgggggct tcactatgtt     300
gcccacactg gactaaaact ctgggcctca agtgattgtc ctgcctcagc ctcctgaata     360
gctgggacta cagggcatg ccatcacacc tagttcattt cctctattta aaatatacat      420
ggcttaaact ccaactggga acccaaaaca ttcatttgct aagagtctgg tgttctacca     480
```

-continued

```
cctgaactag gctggccaca ggaattataa aagctgagaa attctttaat aatagtaacc    540
aggcaacatc attgaaggct catatgtaaa atccatgcc ttcctttctc ccaatctcca     600
ttcccaaact tagccactgg ttctggctga ggccttacgc atacctcccg ggcttgcac     660 acaccttctt ctacagaaga cacaccttgg gcatatccta cagaagacca ggcttctctc    720
tggtccttgg tagagggcta ctttactgta acagggccag ggtggagagt tctctcctga    780
agctccatcc cctctatagg aaatgtgttg acaatattca gaagagtaag aggatcaaga    840
cttctttgtg ctcaaatacc actgttctct tctctaccct gccctaacca ggagcttgtc    900
accccaaact ctgaggtgat ttatgcctta atcaagcaaa cttccctctt cagaaaagat    960
ggctcatttt ccctcaaaag ttgccaggag ctgccaagta ttctgccaat tcaccctgga   1020
gcacaatcaa caattcagc cagaacacaa ctacagctac tattagaact attattatta    1080
ataaattcct ctccaaatct agcccccttga cttcggattt cacgatttct cccttcctcc   1140
tagaaacttg ataagtttcc cgcgcttccc tttttctaag actacatgtt tgtcatctta    1200
taaagcaaag gggtgaataa atgaaccaaa tcaataactt ctggaatatc tgcaaacaac    1260
aataatatca gctatgccat ctttcactat tttagccagt atcgagttga atgaacatag    1320
aaaaatacaa aactgaattc ttccctgtaa attccccgtt ttgacgacgc acttgtagcc    1380
acgtagccac gcctacttaa gacaattaca aaaggcgaag aagactgact caggcttaag    1440
ctgccagcca gagagggagt catttcattg gcgtttgagt cagcaaaggt attgtcctca    1500
catctctggc tattaaagta ttttctgttg ttgtttttct ctttggctgt tttctctcac    1560
attgccttct ctaaagctac agtctctcct ttcttttctt gtccctccct ggtttggtat    1620
gtgacctaga attacagtca gatttcagaa aatgattctc tcattttgct gataaggact    1680
gattcgtttt actgagggac ggcagaacta gtttcctatg agggcatggg tgaatacaac    1740
tgaggcttct catgggaggg aatctctact atccaaaatt attaggagaa aattgaaaat    1800
ttccaactct gtctctctct tacctctgtg taaggcaaat accttattct tgtggtgttt    1860
ttgtaacctc ttcaaacttt cattgattga atgcctgttc tggcaataca ttaggttggg    1920 cataagga ataccaacat aaataaaaca ttctaaaaga agtttacgat ctaataaagg      1980
agacaggtac atagcaaact aattcaaagg agctagaaga tggagaaaat gctgaatgtg    2040
gactaagtca ttcaacaaag ttttcaggaa gcacaaagag gagggctcc cctcacagat     2100 atctggatta gaggctggct gagctgatgg tggctggtgt tctctgttgc agaagtcaag    2160
atggccaaag ttccagacat gtttgaagac ctgaagaact gttacaggta aggaataaga    2220
tttatctctt gtgatttaat gagggtttca aggctcacca gaatccagct aggcataaca    2280
gtggccagca tgggggcagg ccggcagagg ttgtagagat gtgtactagt cctgaagtca    2340
gagcaggttc agagaagacc cagaaaaact aagcattcag catgttaaac tgagattaca    2400
ttggcaggga gaccgccatt ttagaaaaat tattttgag gtctgctgag ccctacatga     2460
atatcagcat caacttagac acagcctctg ttgagatcac atgccctgat ataagaatgg    2520 gtttactgg tccattctca ggaaaacttg atctcattca ggaacaggaa atggctccac     2580
agcaagctgg gcatgtgaac tcacatatgc aggcaaatct cactcagatg tagaagaaag    2640
gtaaatgaac acaaagataa aattacggaa catattaaac taacatgatg tttccattat    2700
ctgtagtaaa tactaacaca aactaggctg tcaaaatttt gcctggatat tttactaagt    2760
ataaattatg aaatctgttt tagtgaatac atgaaagtaa tgtgtaacat ataatctatt    2820
```

-continued

| | | | | |
|---|---|---|---|---|
| tggttaaaat | aaaaaggaag | tgcttcaaaa | cctttctttt | ctctaaagga gcttaacatt | 2880 |
| cttccctgaa | cttcaattaa | agctcttcaa | tttgttagcc | aagtccaatt tttacagata | 2940 |
| aagcacaggt | aaagctcaaa | gcctgtcttg | atgactacta | attccagatt agtaagatat | 3000 |
| gaattactct | acctatgtgt | atgtgtagaa | gtccttaaat | ttcaaagatg acagtaatgg | 3060 |
| ccatgtgtat | gtgtgtgacc | cacaactatc | atggtcatta | aagtacattg gccagagacc | 3120 |
| acatgaaata | acaacaatta | cattctcatc | atcttatttt | gacagtgaaa atgaagaaga | 3180 |
| cagttcctcc | attgatcatc | tgtctctgaa | tcaggtaagc | aaatgactgt aattctcatg | 3240 |
| ggactgctat | tcttacacag | tggtttcttc | atccaaagag | aacagcaatg acttgaatct | 3300 |
| taaatacttt | tgttttaccc | tcactagaga | tccagagacc | tgtctttcat tataagtgag | 3360 |
| accagctgcc | tctctaaact | aatagttgat | gtgcattggc | ttctcccaga acagagcaga | 3420 |
| actatcccaa | atccctgaga | actggagtct | cctggggcag | gcttcatcag gatgttagtt | 3480 |
| atgccatcct | gagaaagccc | cgcaggccgc | ttcaccaggt | gtctgtctcc taacgtgatg | 3540 |
| tgttgtggtt | gtcttctctg | acaccagcat | cagaggttag | agaaagtctc caaacatgaa | 3600 |
| gctgagagag | aggaagcaag | ccagctgaaa | gtgagaagtc | tacagccact catcaatctg | 3660 |
| tgttattgtg | tttggagacc | acaaatagac | actataagta | ctgcctagta tgtcttcagt | 3720 |
| actggcttta | aaagctgtcc | ccaaaggagt | atttctaaaa | tattttgagc attgttaagc | 3780 |
| agatttttaa | cctcctgaga | gggaactaat | tggaaagcta | ccactcacta caatcattgt | 3840 |
| taacctattt | agttacaaca | tctcattttt | gagcatgcaa | ataaatgaaa aagtcttcct | 3900 |
| aaaaaaatca | tcttttatc | ctggaaggag | gaaggaaggt | gagacaaaag ggagagaggg | 3960 |
| agggaagcct | aatgaaacac | cagttaccta | agaccagaat | ggagatcctc ctcactacct | 4020 |
| ctgttgaata | cagcacctac | tgaaagaact | ttcattccct | gaccatgaac agcctctcag | 4080 |
| cttctgtttt | ccttcctcac | agaaatcctt | ctatcatgta | agctatggcc cactccatga | 4140 |
| aggctgcatg | gatcaatctg | tgtctctgag | tatctctgaa | acctctaaaa catccaagct | 4200 |
| taccttcaag | gagagcatgg | tggtagtagc | aaccaacggg | aaggttctga agaagagacg | 4260 |
| gttgagttta | agccaatcca | tcactgatga | tgacctggag | gccatcgcca atgactcaga | 4320 |
| ggaaggtaag | gggtcaagca | caataatatc | tttcttttac | agttttaagc aagtagggac | 4380 |
| agtagaattt | agggggaaaat | taaacgtgga | gtcagaataa | caagaagaca accaagcatt | 4440 |
| agtctggtaa | ctatacagag | gaaaattaat | tttatccttt | ctccaggagg gagaaatgag | 4500 |
| cagtggcctg | aatcgagaat | acttgctcac | agccattatt | tcttagccat attgtaaagg | 4560 |
| tcgtgtgact | tttagccttt | caggagaaag | cagtaataag | accacttacg agctatgttc | 4620 |
| ctctcatact | aactatgcct | ccttggtcat | gttacataat | cttttcgtga ttcagtttcc | 4680 |
| tctactgtaa | aatggagata | atcagaatcc | cccactcatt | ggattgttgt aaagattaag | 4740 |
| agtctcaggc | tttacagact | gagctagctg | ggccctcctg | actgttataa agattaaatg | 4800 |
| agtcaacatc | ccctaacttc | tggactagaa | taatgtctgg | tacaaagtaa gcacccaata | 4860 |
| aatgttagct | attactatca | ttattattat | tattttattt | ttttttttg agatggagtc | 4920 |
| tgctctgtc | acccaggctg | gagtgcagtg | gcacaatctc | ggctcactgc aagctctgcc | 4980 |
| tcctgggttc | atgccattct | cctgcctcag | cctcccgagt | aagctgggaa tacaggcacc | 5040 |
| cgccactgtt | cccggctaat | ttttgtatt | tttagtagag | acggagtttc accgtggtct | 5100 |
| ccatctcctc | gtgatccacc | caccttggcc | tcccaaagtg | ccgggattac aggcgtgagc | 5160 |
| caccgcgccc | ggcctattat | tattattatt | actactacta | ctacctatat gaatactacc | 5220 |

```
agcaatacta atttattaat gactggatta tgtctaaacc tcacaagaat cctaccttct   5280
cattttacat aaaaggaaac taagctcatt gagataggta aactgcccaa tggcatacat   5340
ctgtaagtgg gagagcctca aatctaattc agttctacct gagtaaaaaa atcatggttt   5400
ctcctccatc cctttactgt acaagcctcc acatgaacta taaacccaat attcctgttt   5460
ttaagataat acctaagcaa taacgcatgt tcacctagaa ggttttaaaa tgtaacaaaa   5520
tataagaaaa taaaaatcac tcatatcgtc agtgagagtt tactactgcc agcactatgg   5580
tatgtttcct taaaatcttt gctatacaca tacctacatg tgaacaaata tgtctaacat   5640
caagaccaca ctatttacaa ctttatatcc agcttttctt acttagcaat gtattgagga   5700
cattttagag tgcccgtttt tcaccattat aagcaatgca acaatgaaca tctgtataaa   5760
taaatattca tttctctcac cctttatttc cttagaatat attcctagaa gtagaatttc   5820
ccagagccat gaggatttgt gacgctattg atatgtgcca ctttgcactc tctgtgacat   5880
atataattat ttttaatgca ttcatttttt tctcagagtg cattcgtttg aaaacataga   5940
cgggaaatac tggtagtctt ccttgtcagt tagaaacacc caaacaatga aaatgaaaa    6000 agttgcacaa atagtctcta aaaacaatga aactattgcc tgaggaattg aagtttaaaa   6060
agaagcacat aagcaacaac aaggataatc ctagaaaacc agttctgctg actgggtgat   6120
ttcacttctc tttgcttcct catctggatt ggaatattcc taataccccc tccagaacta   6180
ttttccctgt ttgtactaga ctgtgtatat catctgtgtt tgtacataga cattaatctg   6240
cacttgtgat catggtttta gaaatcatca agcctaggtc atcaccttt agcttcctga    6300 gcaatgtgaa atacaacttt atgaggatca tcaaatacga attcatcctg aatgacgccc   6360
tcaatcaaag tataattcga gccaatgatc agtacctcac ggctgctgca ttacataatc   6420
tggatgaagc aggtacatta aaatggcacc agacatttct gtcatcctcc cctcctttca   6480
tttacttatt tatttatttc aatctttctg cttgcaaaaa acatacctct tcagagttct   6540
gggttgcaca attcttccag aatagcttga agcacagcac ccccataaaa atcccaagcc   6600
agggcagaag gttcaactaa atctggaagt tccacaagag agaagtttcc tatctttgag   6660
agtaaagggt tgtgcacaaa gctagctgat gtactacctc tttggttctt tcagacattc   6720
ttaccctcaa ttttaaaact gaggaaactg tcagacatat taaatgattt actcagattt   6780
acccagaagc caatgaagaa caatcactct ccttttaaaaa gtctgttgat caaactcaca   6840
agtaacacca aaccaggaag atctttatta tctctgataa catatttgtg aggcaaaacc   6900
tccaataagc tacaaatatg gcttaaagga tgaagtttag tgtccaaaaa cttttatcac   6960
acacatccaa ttttcatggc ggacatgttt tagtttcaac agtatacata ttttcaaagg   7020
tccagagagg caattttgca ataaacaagc aagacttttt ctgattggat gcacttcagc   7080
taacatgctt tcaactctac atttacaaat tattttgtgt tctatttttc tacttaatat   7140
tatttctgca atttttccaa tattgacatc gtgtatgtat ttgccatttt taatatcact   7200
agacaattca atcaggttgc tacgttggtc ccttgggttt actctaaata gcttgattgc   7260
aaatatcttt gtatatatta ttgttttttc tcctatcttg taatttcttt gagcacatcc   7320
caaagaggaa tgcctagatc aatgggcaca ataatttga cagctcttat taaacattat    7380
tctgtaagta aaaactgaac tacttttcag tatcactagc aacatatgag tgtatcagct   7440
tcctaaaccc ctccatgtta ggtcattatg aacttatgat ctaacaaatt acagggtctt   7500
atcccactaa tgaaattata agagattcaa cacttattca gccccgaagg attcattcaa   7560
```

-continued

```
cgtagaaaat tctaagaaca ttaaccaagt atttacctgc ctagtgagtg tggaagacat      7620
tgtgaaggac acaaagatgt atagaattcc attcctgact tccaggtatt tacaccatag      7680
gtggggacct aactacacac acacacacac acacacacac acacacacac accatgcaca      7740
cacaatctac atcaacactt gattttatac aaatacaatg aatttacttt cttttttggtt     7800 cttctcttca ccagtgaaat ttgacatggg tgcttataag tcatcaaagg atgatgctaa      7860
aattaccgtg attctaagaa tctcaaaaac tcaattgtat gtgactgccc aagatgaaga      7920
ccaaccagtg ctgctgaagg tcagttgtcc tttgtctcca acttaccttc atttacatct      7980
catatgtttg taaataagcc caataggcag acacctctaa caaggtgaca ctgtcctctt      8040
tccttcctac cacagccccc acctaccac cccactccca ttgattccag aggcgtgcct       8100
aggcaggatc tatgagaaaa tataacagag agtaagagga aaattacctt ctttcttttt      8160
cctttccctg cctgacctta ttcacctccc atcccagagc atccatttat tccattgatc      8220
tttactgaca tctattatct gacctacaca atactagaca ttaggacaat gtggcctgcc      8280
tccaagaaac tcaaataagc caactgagat cagagaggat taatcacctg ccaatgggca      8340
caaagcaaca agctgggagc caagtcccaa aatgggcct gctgcttcca gttcccctct       8400
ctctgcattg atgtcagcat tatccttcgt cccagtcctg tctccactac cactttcccc      8460
ctcaaacaca cacacacaca acagccttag atgttttctc cactgataag taggtgactc      8520
aatttgtaag tatataatcc aagaccttct attcccaagt agaatttatg tgcctgcctg      8580
tgcttttcta cctggatcaa gtgatgtcta cagagtaggc cagtagcttc attcatgaac      8640
tcattcaaca agcattattc actgagagcc ttgtattttt caggcatagt gccaacagca      8700
gtgtggacag tggtgcatca aagcctctag tctcatagaa cttagtcttc tggaggatat      8760
ggaaaacaga caacccaaac aaccaacaaa agagcaagat gctgcaaaaa aaaaaaaaat      8820
gaatagggtg ctaagataga gaaaagtggg agagtgctat ttagacaaag tggtaaaaac      8880
aaagcccctt gtgagatgag agctgccgac agaggggcg ggtcatggtt gtgggttttt       8940
gggtaggaca ttcagaggag gggcgggtc gtggttgtgg gtttttgggt aggacattca       9000
gaggaggggg cgggtcgtgg ttgtgggttt ttgggtagga cattcagagg aggggcggg       9060 tcgtggttgt gggtttttgg gtaggacatt cagaggaggg ggcgggtcgt ggttgtgggt      9120
ttttgggaca ttcagaggag tctgaatgca cccaggccta caacttcaag atggtaaagg      9180
acagctccaa ggatcagaag aagcattctt ggaactgggg cattttgaga aggaggaaaa      9240
atatgcagag actagtgctt gcagagcttg catttggatt tcatttgagg tacaatgaaa      9300
acccattaat gggtttcaca cagtgcaatg gcctgacctc acttatattt cctaaaatag      9360
aaaacagatc agaaggaagg caatagagaa gcagaaagtc caatgaggag gtttcacagc      9420
agtcatgggg gtggggtaag gaaaagaagt ggaaagaaac agacagaatt gggttatatt      9480
ttggagatag aaccaacaga aggaagagga gaaacaacat ttactgagaa gggaaaaagt      9540
aggagaggaa taggtttggg aaataaatcc tgctgacatt ggaaacccca aggaagcctc      9600
aaaagtatat ttacttgctt tagatttaaa agaataggaa agaagcatct caacttggaa      9660
tttgaaatct atttttccat aaaagtattg ttaaattcta ctcatactca caagaaaagt      9720
acattctaaa gagtatattg aaaagagttta ctgatatact taggaatttt gtgtgtatgt     9780
gtgtgtgtgt atgtgtgtgt gtgtgtttaa ccttcaattg ttgacttaaa tactgagata     9840
aatgtcatct aaatgctaaa ttgatttccc aaaggtatga tttgttcact tggagatcaa      9900
aatgtttagg gggcttagaa tcactgtagt gctcagattt gatgcaaaat gtcttaggcc      9960
```

-continued

```
tatgttgaag gcaggacaga aacaatgttt ccctcctacc tgcctggata cagtaagata    10020
ctagtgtcac tgacaatctt cataactaat ttagatctct ctccaatcaa ctaaggaaat    10080
caactcttat taatagactg ggccacacat ctactaggca tgtaataaat gcttgctgaa    10140
tgaacaaatg aatgaagagc ctatagcatc atgttacagc catagtccta aagtggtgtt    10200
tctcatgaag gccaaatgct aagggattga gcttcagtcc ttttctaac atcttgttct     10260 ctaacagaat tctcttcttt tcttcatagg agatgcctga gatacccaaa accatcacag    10320
gtagtgagac caacctcctc ttcttctggg aaactcacgg cactaagaac tatttcacat    10380
cagttgccca tccaaacttg tttattgcca caaagcaaga ctactgggtg tgcttggcag    10440
gggggccacc ctctatcact gactttcaga tactggaaaa ccaggcgtag gtctggagtc    10500
tcacttgtct cacttgtgca gtgttgacag ttcatatgta ccatgtacat gaagaagcta    10560
aatcctttac tgttagtcat ttgctgagca tgtactgagc cttgtaattc taaatgaatg    10620
tttacactct ttgtaagagt ggaaccaaca ctaacatata atgttgttat ttaaagaaca    10680
ccctatattt tgcatagtac caatcatttt aattattatt cttcataaca attttaggag    10740
gaccagagct actgactatg gctaccaaaa agactctacc catattacag atgggcaaat    10800
taaggcataa gaaaactaag aaatatgcac aatagcagtt gaaacaagaa gccacagacc    10860
taggatttca tgatttcatt tcaactgttt gccttctgct tttaagttgc tgatgaactc    10920
ttaatcaaat agcataagtt tctgggacct cagttttatc attttcaaaa tggagggaat    10980 aataacctaag ccttcctgcc gcaacagttt tttatgctaa tcagggaggt cattttggta    11040
aaatacttct cgaagccgag cctcaagatg aaggcaaagc acgaaatgtt atttttttaat    11100 tattatttat atatgtattt ataaatatat ttaagataat tataatatac tatatttatg    11160
ggaacccctt catcctctga gtgtgaccag gcatcctcca caatagcaga cagtgttttc    11220
tgggataagt aagtttgatt tcattaatac agggcatttt ggtccaagtt gtgcttatcc    11280
catagccagg aaactctgca ttctagtact tgggagacct gtaatcatat aataaatgta    11340
cattaattac cttgagccag taattggtcc gatctttgac tcttttgcca ttaaacttac    11400
ctgggcattc ttgttttcatt caattccacc tgcaatcaag tcctacaagc taaaattaga    11460
tgaactcaac tttgacaacc atgagaccac tgttatcaaa actttctttt ctggaatgta    11520
atcaatgttt cttctaggtt ctaaaaattg tgatcagacc ataatgttac attattatca    11580
acaatagtga ttgatagagt gttatcagtc ataactaaat aaagcttgca acaaaattct    11640 ctgcacacata gttattcatt gccttaatca ttattttact gcatggtaat tagggacaaa    11700
tggtaaatgt ttacataaat aattgtattt agtgttactt tataaaatca aaccaagatt    11760 ttatatttt ttctcctctt tgttagctgc cagtatgcat aaatggcatt aagaatgata    11820
atatttccgg gttcacttaa agctcatatt acacatacac aaaacatgtg ttcccatctt    11880
tatacaaact cacacataca gagctacatt aaaaacaact aataggccag gcacggtggc    11940
tcagacctgt aatcccagca ctttgggagg                                     11970
```

<210> SEQ ID NO 2
<211> LENGTH: 9721
<212> TYPE: DNA
<213> ORGANISM: Homo sapiens
<220> FEATURE:
<221> NAME/KEY: modified_base
<223> OTHER INFORMATION: a, c, t, g, other or unknown

<400> SEQUENCE: 2

```
agaaagaaag agagagagaa agaaaagaaa gaggaaggaa ggaaggaagg aagaaagaca      60
ggctctgagg aaggtggcag ttcctacaac gggagaacca gtggttaatt tgcaaagtgg     120
atcctgtgga ggcanncaga ggagtcccct aggccaccca gacagggctt ttagctatct     180
gcaggccaga caccaaattt caggagggct cagtgttagg aatggattat ggcttatcaa     240
attcacagga aactaacatg ttgaacagct tttagatttc ctgtggaaaa tataacttac     300
taaagatgga gttcttgtga ctgactcctg atatcaagat actgggagcc aaattaaaaa     360
tcagaaggct gcttggagag caagtccatg aaatgctctt tttcccacag tagaacctat     420
ttccctcgtg tctcaaatac ttgcacagag gctcactccc ttggataatg cagagcgagc     480
acgatacctg gcacatacta atttgaataa aatgctgtca aattcccatt cacccattca     540
agcagcaaac tctatctcac ctgaatgtac atgccaggca ctgtgctaga cttggctcaa     600
aaagatttca gtttcctgga ggaaccagga gggcaaggtt tcaactcagt gctataagaa     660
gtgttacagg ctggacacgg tggctcacgc ctgtaatccc aacatttggg aggccgaggc     720
gggcagatca caaggtcagg agatcgagac catcctggct aacatggtga aaccctgtct     780
ctactaaaaa tacaaaaaat tagccgggcg ttggcggcag gtgcctgtag tcccagctgc     840
tggggaggct gaggcaggag aatggtgtga acccgggagg cggaacttgc aggggggccga     900 gatcgtgcca ctgcactcca gcctgggcga cagagtgaga ctctgtctca aaaaaaaaa     960 aaaagtgtta tgatgcagac ctgtcaaaga ggcaaaggag ggtgttccta cactccaggc    1020
actgttcata acctggactc tcattcattc tacaaatgga gggctcccct gggcagatcc    1080
ctggagcagg cactttgctg gtgtctcggt taaagagaaa ctgataactc ttggtattac    1140
caagagatag agtctcagat ggatattctt acagaaacaa tattcccact tttcagagtt    1200
caccaaaaaa tcattttagg cagagctcat ctggcattga tctggttcat ccatgagatt    1260
ggctagggta acagcacctg gtcttgcagg gttgtgtgag cttatctcca gggttgcccc    1320
aactccgtca ggagcctgaa ccctgcatac cgtatgttct ctgccccagc caagaaaggt    1380
caattttctc ctcagaggct cctgcaattg acagagagct cccgaggcag agaacagcac    1440
ccaaggtaga gacccacacc tcaatacag acagggaggg ctattggccc ttcattgtac     1500
ccatttatcc atctgtaagt gggaagattc ctaaacttaa gtacaaagaa gtgaatgaag    1560
aaaagtatgt gcatgtataa atctgtgtgt cttccacttt gtcccacata tactaaattt    1620
aaacattctt ctaacgtggg aaaatccagt attttaatgt ggacatcaac tgcacaacga    1680
ttgtcaggaa aacaatgcat atttgcatgg tgatacattt gcaaaatgtg tcatagtttg    1740
ctactccttg cccttccatg aaccagagaa ttatctcagt ttattagtcc cctcccctaa    1800
gaagcttcca ccaatactct tttccccttt cctttaactt gattgtgaaa tcaggtattc    1860
aacagagaaa tttctcagcc tcctacttct gcttttgaaa gctataaaaa cagcgaggga    1920
gaaactggca gataccaaac ctcttcgagg cacaaggcac aacaggctgc tctgggattc    1980
tcttcagcca atcttcattg ctcaagtatg actttaatct tccttacaac taggtgctaa    2040
gggagtctct ctgtctctct gcctctttgt gtgtatgcat attctctctc tctctctctt    2100
tctttctctg tctctcctct ccttcctctc tgcctcctct ctcagctttt tgcaaaaatg    2160
ccaggtgtaa tataatgctt atgactcggg aaatattctg ggaatggata ctgcttatct    2220
aacagctgac accctaaagg ttagtgtcaa agcctctgct ccagctctcc tagccaatac    2280
attgctagtt ggggtttggt ttagcaaatg cttttctcta gacccaaagg acttctcttt    2340
```

```
cacacattca ttcatttact cagagatcat ttctttgcat gactgccatg cactggatgc    2400
tgagagaaat cacacatgaa cgtagccgtc atggggaagt cactcatttt ctccttttta    2460
cacaggtgtc tgaagcagcc atggcagaag tacctgagct cgccagtgaa atgatggctt    2520
attacaggtc agtggagacg ctgagaccag taacatgagc aggtctcctc tttcaagagt    2580
agagtgttat ctgtgcttgg agaccagatt tttcccctaa attgcctctt tcagtggcaa    2640
acagggtgcc aagtaaatct gatttaaaga ctactttccc attacaagtc cctccagcct    2700
tgggacctgg aggctatcca gatgtgttgt tgcaagggct tcctgcagag gcaaatgggg    2760
agaaaagatt ccaagcccac aatacaagga atccctttgc aaagtgtggc ttggagggag    2820
agggagagct cagattttag ctgactctgc tgggctagag gttaggcctc aagatccaac    2880
agggagcacc agggtgccca cctgccaggc ctagaatctg ccttctggac tgttctgcgc    2940
atatcactgt gaaacttgcc aggtgtttca ggcagctttg agaggcaggc tgtttgcagt    3000
ttcttatgaa cagtcaagtc ttgtacacag ggaaggaaaa ataaacctgt ttagaagaca    3060
taattgagac atgtccctgt ttttattaca gtggcaatga ggatgacttg ttctttgaag    3120
ctgatggccc taaacagatg aaggtaagac tatgggttta actcccaacc caaggaaggg    3180
ctctaacaca gggaaagctc aaagaaggga gttctgggcc actttgatgc catggtattt    3240
tgttttagaa agactttaac ctcttccagt gagacacagg ctgcaccact tgctgacctg    3300
gccacttggt catcatatca ccacagtcac tcactaacgt tggtggtggt ggccacactt    3360
ggtggtgaca ggggaggagt agtgataatg ttcccatttc atagtaggaa acaaccaag    3420 tcttcaacat aaatttgatt atcctttta gagatggatt cagcctatgc caatcacttg    3480
agttaaactc tgaaaccaag agatgatctt gagaactaac atatgtctac cccttttgag    3540
tagaatagtt ttttgctacc tggggtgaag cttataacaa caagacatag atgatataaa    3600
caaaaagatg aattgagact tgaaagaaaa ccattcactt gctgtttgac cttgacaagt    3660
cattttaccc gctttggacc tcatctgaaa aataaagggc tgagctggat gatctctgag    3720
attccagcat cctgcaacct ccagttctga aatattttca gttgtagcta agggcatttg    3780
ggcagcaaat ggtcattttt cagactcatc cttacaaaga gccatgttat attcctgctg    3840
tcccttctgt tttatatgat gctcagtagc cttcctaggt gcccagccat cagcctagct    3900
aggtcagttg tgcaggttgg aggcagccac ttttctctgg ctttattta ttccagtttg    3960 tgatagcctc ccctagcctc ataatccagt cctcaatctt gttaaaaaca tatttcttta    4020
gaagttttaa gactggcata acttcttggc tgcagctgtg ggaggagccc attggcttgt    4080
ctgcctggcc tttgcccccc attgcctctt ccagcagctt ggctctgctc caggcaggaa    4140
attctctcct gctcaacttt cttttgtgca cttacaggtc tctttaactg tcttcaagc    4200 ctttgaacca ttatcagcct taaggcaacc tcagtgaagc cttaatacgg agcttctctg    4260
aataagagga aagtggtaac atttcacaaa aagtactctc acaggatttg cagaatgcct    4320
atgagacagt gttatgaaaa aggaaaaaaa agaacagtgt agaaaaattg aatacttgct    4380
gagtgagcat aggtgaatgg aaaatgttat ggtcatctgc atgaaaaagc aaatcatagt    4440
gtgacagcat tagggataca aaagatata gagaaggtat acatgtatgg tgtaggtggg    4500
gcatgtacaa aaagatgaca agtagaatcg ggatttattc taaagaatag cctgtaaggt    4560
gtccagaagc cacattctag tcttgagtct gcctctacct gctgtgtgcc cttgagtaca    4620
cccttaacct ccttgagctt cagagaggga taatcttttt atttattttt attttatttt    4680
gttttgtttt gttttgtttt gttttatgag acagagtctc actctgttgc ccaggctgga    4740
```

```
gtgcagtggt acaatcttgg cttactgcat cctccacctc ctgagttcaa gcgattctcc    4800
ttcctcagtc tcctgaatag ctaggattac aggtgcaccc caccacaccc agctaatttt    4860 tgtatttta gtagagaagg ggtttcgcca tgttggccag gctggttttg aagtcctgac     4920
ctaaatgatt catccacctc ggcttcccaa agtgctggga ttacaggcat gagccaccac    4980
gcctggccca gagagggatg atctttagaa gctcgggatt ctttcaagcc cttcctcct    5040 ctctgagctt tctactctct gatgtcaaag catggttcct ggcaggacca cctcaccagg    5100
ctccctccct cgctctctcc gcagtgctcc ttccaggacc tggacctctg ccctctggat    5160
ggcggcatcc agctacgaat ctccgaccac cactacagca agggcttcag gcaggccgcg    5220
tcagttgttg tggccatgga caagctgagg aagatgctgg ttccctgccc acagaccttc    5280
caggagaatg acctgagcac cttctttccc ttcatctttg aagaaggtag ttagccaaga    5340
gcaggcagta gatctccact tgtgtcctct tggaagtcat caagcccag ccaactcaat     5400 tcccccagag ccaaagccct ttaaaggtag aaggcccagc ggggagacaa acaaagaag     5460 gctggaaacc aaagcaatca tctctttagt ggaaactatt cttaaagaag atcttgatgg    5520
ctactgacat ttgcaactcc ctcactcttt ctcagggggcc tttcacttac attgtcacca   5580
gaggttcgta acctccctgt gggctagtgt tatgaccatc accattttac ctaagtagct    5640
ctgttgctcg gccacagtga gcagtaatag acctgaagct ggaacccatg tctaatagtg    5700
tcaggtccag tgttcttagc caccccactc ccagcttcat ccctactggt gttgtcatca    5760
gactttgacc gtatatgctc aggtgtcctc caagaaatca aattttgcca cctcgcctca    5820
cgaggcctgc ccttctgatt ttatacctaa acaacatgtg ctccacattt cagaacctat    5880
cttcttcgac acatgggata acgaggctta tgtgcacgat gcacctgtac gatcactgaa    5940
ctgcacgctc cgggactcac agcaaaaaag cttggtgatg tctggtccat atgaactgaa    6000
agctctccac ctccagggac aggatatgga gcaacaaggt aaatggaaac atcctggttt    6060
ccctgcctgg cctcctggca gcttgctaat tctccatgtt ttaaacaaag tagaaagtta    6120
atttaaggca aatgatcaac acaagtgaaa aaaatatta aaaaggaata tacaaacttt     6180
ggtcctagaa atggcacatt tgattgcact ggccagtgca tttgttaaca ggagtgtgac    6240
cctgagaaat tagacggctc aagcactccc aggaccatgt ccacccaagt ctcttgggca    6300
tagtgcagtg tcaattcttc cacaatatgg ggtcatttga tggacatggc ctaactgcct    6360
gtgggttctc tcttcctgtt gttgaggctg aaacaagagt gctggagcga taatgtgtcc    6420
atccccctcc ccagtcttcc cccttgccc caacatccgt cccacccaat gccaggtggt    6480
tccttgtagg gaaattttac cgcccagcag gaacttatat ctctccgctg taacgggcaa    6540
aagtttcaag tgcggtgaac ccatcattag ctgtggtgat ctgcctggca tcgtgccaca    6600
gtagccaaag cctctgcaca ggagtgtggg caactaaggc tgctgacttt gaaggacagc    6660
ctcactcagg gggaagctat ttgctctcag ccaggccaag aaaatcctgt ttctttggaa    6720
tcgggtagta agagtgatcc cagggcctcc aattgacact gctgtgactg aggaagatca    6780
aaatgagtgt ctctctttgg agccactttc ccagctcagc ctctcctctc ccagtttctt    6840
cccatgggct actctctgtt cctgaaacag ttctggtgcc tgatttctgg cagaagtaca    6900
gcttcacctc tttcctttcc ttccacattg atcaagttgt tccgctcctg tggatgggca    6960
cattgccagc cagtgacaca atggcttcct tccttccttc cttcagcatt taaaatgtag    7020
accctctttc attctccgtt cctactgcta tgaggctctg agaaaccctc aggcctttga    7080
```

```
ggggaaaccc taaatcaaca aaatgaccct gctattgtct gtgagaagtc aagttatcct    7140
gtgtcttagg ccaaggaacc tcactgtggg ttcccacaga ggctaccaat tacatgtatc    7200
ctactctcgg ggctagggt tggggtgacc ctgcatgctg tgtccctaac cacaagaccc    7260
ccttctttct tcagtggtgt tctccatgtc ctttgtacaa ggagaagaaa gtaatgacaa    7320
aatacctgtg gccttgggcc tcaaggaaaa gaatctgtac ctgtcctgcg tgttgaaaga    7380
tgataagccc actctacagc tggaggtaag tgaatgctat ggaatgaagc ccttctcagc    7440
ctcctgctac cacttattcc cagacaattc accttctccc cgcccccatc cctaggaaaa    7500
gctgggaaca ggtctatttg acaagttttg cattaatgta aataaattta acataatttt    7560
taactgcgtg caaccttcaa tcctgctgca gaaaattaaa tcattttgcc gatgttatta    7620
tgtcctacca tagttacaac cccaacagat tatatattgt tagggctgct ctcatttgat    7680
agacaccttg ggaaatagat gacttaaagg gtcccattat cacgtccact ccactcccaa    7740
aatcaccacc actatcacct ccagctttct cagcaaaagc ttcatttcca agttgatgtc    7800
attctaggac cataaggaaa aatacaataa aaagccctg gaaactaggt acttcaagaa    7860
gctctagctt aattttcacc ccccaaaaa aaaaaaattc tcacctacat tatgctcctc    7920
agcatttggc actaagtttt agaaaagaag aagggctctt ttaataatca cacagaaagt    7980
tgggggccca gttacaactc aggagtctgg ctcctgatca tgtgacctgc tcgtcagttt    8040
cctttctggc caacccaaag aacatctttc ccataggcat ctttgtccct tgccccacaa    8100
aaattcttct ttctctttcg ctgcagagtg tagatcccaa aaattaccca agaagaaga    8160
tggaaaagcg atttgtcttc aacaagatag aaatcaataa caagctggaa tttgagtctg    8220
cccagttccc caactggtac atcagcacct ctcaagcaga aaacatgccc gtcttcctgg    8280
gagggaccaa aggcggccag gatataactg acttcaccat gcaatttgtg tcttcctaaa    8340
gagagctgta cccagagagt cctgtgctga atgtggactc aatccctagg ctggcagaa    8400
agggaacaga aaggtttttg agtacggcta tagcctggac tttcctgttg tctacaccaa    8460
tgcccaactg cctgccttag ggtagtgcta agaggatctc ctgtccatca gccaggacag    8520
tcagctctct cctttcaggg ccaatcccca gcccttttgt tgagccaggc ctctctcacc    8580
tctcctactc acttaaagcc cgcctgacag aaaccacggc cacatttggt tctaagaaac    8640
cctctgtcat tcgctcccac attctgatga gcaaccgctt ccctatttat ttatttattt    8700
gtttgtttgt tttgattcat tggtctaatt tattcaaagg gggcaagaag tagcagtgtc    8760
tgtaaaagag cctagttttt aatagctatg gaatcaattc aatttggact ggtgtgctct    8820
ctttaaatca agtcctttaa ttaagactga aaatatataa gctcagatta tttaaatggg    8880
aatatttata aatgagcaaa tatcatactg ttcaatggtt ctgaaataaa cttcactgaa    8940
gaaaaaaaa aaagggtctc tcctgatcat tgactgtctg gattgacact gacagtaagc    9000
aaacaggctg tgagagttct tgggactaag cccactcctc attgctgagt gctgcaagta    9060
cctagaaata tccttggcca ccgaagacta tcctcctcac ccatcccctt tatttcgttg    9120
ttcaacagaa ggatattcag tgcacatctg gaacaggatc agctgaagca ctgcagggag    9180
tcaggactgg tagtaacagc taccatgatt tatctatcaa tgcaccaaac atctgttgag    9240
caagcgctat gtactaggag ctgggagtac agagatgaga acagtcacaa gtccctcctc    9300
agataggaga ggcagctagt tataagcaga acaaggtaac atgacaagta gagtaagata    9360
gaagaacgaa gaggagtagc caggaaggag ggaggagaac gacataagaa tcaagcctaa    9420
agggataaac agaagatttc cacacatggg ctgggccaat tgggtgtcgg ttacgcctgt    9480
```

-continued

| | |
|---|---|
| aatcccagca ctttgggtgg caggggcaga aagatcgctt gagcccagga gttcaagacc | 9540 |
| agcctgggca acatagtgag actcccatct ctacaaaaaa taaataaata aataaaacaa | 9600 |
| tcagccaggc atgctggcat gcacctgtag tcctagctac ttgggaagct gacactggag | 9660 |
| gattgcttga gcccagaagt tcaagactgc agtgagctta ccgttgacc tgcaggtcga | 9720 |
| c | 9721 |

<210> SEQ ID NO 3
<211> LENGTH: 12565
<212> TYPE: DNA
<213> ORGANISM: Homo sapiens

<400> SEQUENCE: 3

| | |
|---|---|
| gtcgacctgc aggtcaacgg atctgagagg agagtagctt cttgtagata acagttggat | 60 |
| tatataccat gtcctgatcc ccttcatcat ccaggagagc agaggtggtc accctgatag | 120 |
| cagcaagcct gggggctgca gcttggtggg tagaggtact caggggtaca gatgtctcca | 180 |
| aacctgtcct gctgccttag ggagcttcta ataagttgat ggatttggtt aaaattaact | 240 |
| tggctacttg gcaggactgg gtcagtgagg accaacaaaa agaagacatc agattatacc | 300 |
| ctggggggttt gtatttcttg tgtttctttc tcttctttgt actaaaatat ttacccatga | 360 |
| ctgggaaaga gcaactggag tctttgtagc attatcttag caaaaattta caagtttgg | 420 |
| aaaacaatat tgcccatatt gtgtggtgtg tcctgtgaca ctcaggattc aagtgttggc | 480 |
| cgaagccact aaatgtgaga tgaagccatt acaaggcagt gtgcacatct gtccacccaa | 540 |
| gctggatgcc aacatttcac aaatagtgct tgcgtgacac aaatgcagtt ccaggaggcc | 600 |
| caaatgaaaa tgtttgtact gaaatttgtt aaagcttccc gacaaactag atttatcagt | 660 |
| aaggattgtt ttctgcaagg gggatgaaac ttgtggggtg agccatttgg gctgaggagg | 720 |
| agggaggttg gagctgagaa atgtggagac aatttcccctt tagaaggact gaatctccct | 780 |
| gcctctctgg ggtgcggcag ccagcaggat ccaatggtgt atatgtctcc ccagctcccc | 840 |
| attcagtgat atcatgtcag tagcttgaaa ttatccgtgg tgggagtatt atgtcatgga | 900 |
| aattggcaaa tggaaacttt tattggagat tcaattgtta aacttttacc agcacaacac | 960 |
| tgccctgcct tcagagtcaa tgaccctatc caagtttaat ccatctgtcc actgtctcca | 1020 |
| acacgatctt tataaaacac acctgacaac attacccttt tattcagttt tttaaaagat | 1080 |
| aagtttccag ctcatcgggg tggctttaaa ggccatttct cctctggacc tcacccaact | 1140 |
| tttcaaatca cttttcctac ccctacctct aaatgctact caaactccag ccatcctgaa | 1200 |
| taataagact tttgaaaagt agattatggg ctgggcacag tggctcacac ctgtaatccc | 1260 |
| agcactttgg gaggccaaga tgggtggatc acctgaggtc gggagttcga gaccagcctg | 1320 |
| actaacatag tgaaaccctg tctctactaa aaatacaaaa ttagttgggg gtggtggcac | 1380 |
| aagcctgtaa tcccagctac tcaggaggtt gaggcagggg aattgcttga acctgggagg | 1440 |
| cggaggttgc ggtgagccta gattgctcca ctgcactcca gcctgggcaa caagagcgaa | 1500 |
| actccatctc aaaaaaataa ataaataaat aaagtagatt acatcagata cctctggcct | 1560 |
| aggttgttta tgaccaactc tcctgctgag ataactaga aaagctagac aaaacatatt | 1620 |
| tccaaaagat ctcttggag gcatcagaga atggccaagg ctgtaaggaa ctgcctgagc | 1680 |
| ccagagaggt ggagcccagc actggtgccc tttactcctg gggacatgtg ctggtttcaa | 1740 |
| aaacttcagc tgagcttttg agcattcatg gaacttggtg ggggagatga aatttgtacc | 1800 |

```
ttaaatcctg cctacaggga gggtccctga taatccccac ccaatttgga aatctgggtc    1860
agccttcaca ggtactgaag ccctcctctg aatgatctca agtcctgcta gggtagaggt    1920
tacctgcttt tgaaaggctc ctggcctacc tgtgcagcag gagcaaaagt gaaccatctc    1980
agggtacaga taacaatcat ccagagcctt gaatgacctc tactgtgctt aatatatagt    2040
attcagcagt cagtaaaaag gatttaggca catgcaagat gacctgtgta tcagggagaa    2100
ataggcaata aattgagatc cagcagggat ttgaatcatg gatttgaatc aggggcagcc    2160
ttcgaaagaa ctatggagaa tatactcaga tttaaaacat aagattggaa tttttggcag    2220
agaactaaca actgtacaaa aaaggaacca aatggaaatc ctagaactga agatgcaat     2280 taaccgatgt tgagaaatag ccaacatcta ttgaacactt cccatgtgga cagctgtgct    2340
aaacacttta caggcatcaa cataagatgt gtccccttac agcagtgcag tgtccctcct    2400
aagacatgga cagcctggtt tccctatctc tctgcttcat caaaacccct ttacgtgggg    2460
cttagacact cctgttgtct ctagtgtcta gtagcacagg gctcagcaca tggaagccac    2520
tagatacaat tgatgacca ggacctccga tgaaagccat gggtgctgat tgggaaggca     2580
ttgtctttta tgtgctatgg tcttaaagct tcatccagga agcagaactc gggggtgct     2640 gaggacccag aaccgagaat aagattagtc agagatttcc tgtgggcaga aatcataagg    2700
acgccaactg tttgggtgag ataagacgaa accaagagtg gacttgtggc cagaagcgtg    2760
aggaagaggg agagagcttc ccttgtcccc tttcttcctc tccctaagcc acagtgattg    2820
acagcccccc cgctttggag tcagagcagg cttgagactg gactgggaaa ggagggtggg    2880
tcaggataca gagcaggaag gctgggagtg cagggcagga gcaagggct ggggcattca     2940 ttgtgcctga tctctcccac tttacctggg gtaaagaagc atatgcaaaa gccacggtgt    3000
gagtatttcc caagtgccag ggtcagggca tgattcatca cgtgcagcat ttcattcaat    3060
ccttatagta accgatgatg tggcttctat tattagctct atcagataat gaaactgaga    3120
ccaagacagg ctctgcacat tgtgtgggt aatgacacag ggggattcag acctagactc     3180
cataactcct gccccaggga ccaccccac cctcaccctg tgcatgtcga caaggacag      3240 actgggccac ttctcaggac acagcgggga aatgacacag agcaggagg ttccaggagc     3300 cccgagcgtc ttttctccag gagaatactc tctgaattca gactgggtc agagaaacat     3360 ttacccagga gccgcagtgt gggtgggct ttttacttga aacgctgtct gaaggcagtg     3420
gcaggatgaa ctctccaccc taccttggca agccacttct cttctgcaat ctgtaaggac    3480
attgttgaga gaattatggt cttccaattc cggagggttg aagaaagaca aataggagag    3540
aacctatcat agtcaggtgc tagctgcctt ctctttcaga gagtgtgaga ataaagtgat    3600
acacttgatt attagcaaat actttggaaa ttttaaacgc taatattcaa cacactctgg    3660
aagaggcaaa taagtagaca ggttcatata catcatctcc ttcagctagt cctcacaaaa    3720
acaaacaaat gaataaacaa aattcttctt tggccctcat aggaagacac tgtttcttga    3780
acgtgtttca aaaggatgg gtgactcact caaggtcaca ctgtttatga ggacagtaca     3840
ggaatacaga catgccattt tgcctgaaaa atccatcac ccagggaggt gacacaattt     3900
tgcagaaatg ttctatttcc tctgaaggat acattcttta aaccttggg aaattcattc     3960 atagtcttcc tcctttgaag gattactctc tggacacaaa gtgtttgatt ctgatttgtt    4020
ggttggaaga tgtgttggtt gagagaaaga ttctgatttg ttggttgaaa atagactcat    4080
caagatcaac tgctgtagta gtaaatattt tgacattttg tctgtattcc tgtgctgccc    4140
tcacaagctg catcaccttg agtgagtcat tcatactttt ttgtttgttt ttgttttgga    4200
```

-continued

```
gatggagtct tactctgttg cctaggctgg agtgcggtgg cgtgatcttg gctcactgcg     4260
acctccatct cctgggttca agtgatcctc ctgcctcagc ctcccgagta gctgggatta     4320
caggcacatg ccaccatccc tgctaatttt tgcatttca gtagagacgg agtttcacca      4380
tgttggtcag gttggtcttg aactcctgac ctcaggtgat ccgcccacct cagcctcccc    4440
aagtgctggg attacaggtg tgagccaccg tgcccagccc agccatcatt tttgaaacac    4500
gtttgagaaa tagtgtcttc ctttgagggc caaggagaca ttttttttgt ttatttgttt    4560 gttttttgtga ggactagctg aagggggtga tgtatattaa cctgcctact tatttgcctc   4620
ttcccagagt gtgatgaata ttagggttta agtttctga agcatttgtt aataaagccc     4680
ggggctggag gtcagaagac ctggatttct ctgcatactt ttgccatcag caagctgtgt    4740
gaccttggac agatcccttt tttgtctaaa tctttctgag tcttcttgaa acaatgcca     4800 ggttgggaca ggatgattgc caagctcccg tccagctcta aaacactgca acgtatgctt   4860
ctgcaccagc actgtccatc ctgtagatca tgcagaaatt ctcttcaact ttttcctacc    4920
cataaaatag gagcatgctt accttttcc taatgttcca ggccccgggt ctagatattg     4980
taagtaagga agttaatgtg tatcagagcc cattatgggc cagaagttct cctcttcctt    5040
cctacacctg cttcctccct ccctccctcc ctctttccct tccttccttc catccatttg    5100
tgaagaagac atgatcaccc tcattctgag agtgaagaga cagaggctca actaatgaaa    5160
tgatttgttc aaggtcacac gggtggcaca aggcaagtgg cagaggttga atttagaccc    5220
attcctgtcc aaatgctgag tttatgtcat cgtcccgaga ccataacttt aaagatgtaa    5280
gatagtggga aaagagttga tttcaaagca cctctcagaa ggactcactt tacatcaggg    5340
gtcagcagac tcaggccaaa tccggtccat tccccgcttt tgcaaagaaa gttgtagtgg    5400
aacacagcta ggcttattga tttatggatt gccaacgtcc ttttgtgaaa cagacagctg    5460
agctgagtaa tcgtggcgca caaaacctaa aatatttact atctcgtcct ttacagaatg    5520
tttgccaatc tatggtccgg agtccaaggc tgtccatttt tcaaagaaca caaagtgaca    5580
tgagactgtc ccatgtgcag ggagccctat cattttatta tgaaaaaacg gcctttctgc    5640
tcaaatctgt ttttaaaaa gtcaacaaac agactctggg tacctgtcag gaacagtagg     5700
gagtttggtt tccattgtgc tcttcttccc aggaactcaa tgaagggaa atagaaatct     5760 taattttggg gaaattgcac aggggaaaaa ggggagggaa tcagttacaa cactccattg    5820
cgacacttag tggggttgaa agtgacaaca gcaagggttt ctcttttggg aaatgcgagg    5880
agggtatttc cgcttctcgc agtggggcag ggtggcagac gcctagcttg ggtgagtgac    5940 tatttctta taaaccacaa ctctgggccc gcaatggcag tccactgctt gctgcagtca    6000
cagaatggaa atctgcagag gcctccgcag tcacctaatc actctcctcc tcttcctgtt   6060
ccattcagag acgatctgcc gaccctctgg gagaaaatcc agcaagatgc aagcttcag    6120 gtaaggctac cccaaggagg agaaggtgag ggtggatcag ctggagactg aaacatatc    6180 acagctgcca gggctgccag gccagagggc ctgagaactg ggtttgggct ggagaggatg  6240
tccattattc aagaaagagg ctgttacatg catgggcttc aggacttgtg tttcaaaata   6300
tcccagatgt ggatagtgcg accggagggc tgtcttactt tcccagagac tcaggaaccc   6360
agtgagtaat agatgcatgc caaggagtgg gactgcgatt caggcctagt tgaatgtgct   6420
gacagagaag cagagagggg caccaggggc acagcccgaa ggcccagact gatatgggca   6480
aggcctgtct gtgctgacat gtcggagggt cccactctcc agggaccttg gtttccccgt  6540
```

```
ctgtgacatc tgtgacatga gagtcacgat aactccttgt gtgccttaca gggttgttgt    6600
gaaaattaaa tgcacagata atagcgtaac agtattccgt gcattgtaaa gagcctgaaa    6660
accattatga tttgaaaatg gaatcggctt tgtgagacca tcactattgt aaagatgtga    6720
tgctgataga aatgacagga ctgcttgtgc atgccctctg cagtgtgaca ttccagcagt    6780
gaaatcatgt tggggtgact ctcccccac tctgaccttt atgtttgtct gggccgaggc    6840
tgcaagtcgg gctctgtggg tgtatgagtg acaagtctct cccttccaga tatggggact    6900
gtctgcttcc ctaggttgcc ctccctgct ctgatcagct agaagctcca ggagatcctc    6960
ctggaggccc cagcaggtga tgtttatccc tccagactga ggctaaatct agaaactagg    7020
ataatcacaa acaggccaat gctgccatat gcaaagcact ttggtttgcc tggccacccc    7080
tcgtcgagca tgtgggctct tcagagcacc tgatgaggtg ggtacagtta gccacacttc    7140
acaggtgaag aggtgaggca caggtcccag gtcaggctgg ccggagctct gtttattacg    7200
tctcacagct ttgagtcctg ctctcaacca gagaggccct ttaccaagaa gaaaggattg    7260
ggacccagaa tcaggtcact ggctgaggta gagaggaagc cgggttgttc caagggtag    7320 ctgctcctgc aggactctga gcaggtcacc agctaatgga ggaaaggctc tagggaaaga    7380
cccttctggt ctcagactca gagcgagtta gctgcaaggt gttccgtctc ttgaaacttc    7440
tacctaggtg ctatggtagc cactagtctc aggtggctat ttaaatttat acttaaatga    7500
atgaaaatag aagaaaattt aaaatccaga cccttggtca cactatccac atttaaagag    7560
gtcaatagcc acatgtggtt agtggccacc ctattgggca gtgcagctac agaacatttt    7620
tgcatcccag aaagttcttt tggatgttgc tgctctacag catgctttgc tgaaacagaa    7680
gtgccttccc tgggaatctc agatgggaag caagtaagga ggggagtcaa atgtgggctc    7740
actgctcacc agctgtgagg gttgggcctg cctcttaacc attgtcagcc tcagtcttct    7800
catccatgca tgccgtgggt atactaaaat actatacccc tggaagagct ggatgcaaat    7860
ttgacaagtt ctgggggaca caggaaggtg ccaagcacaa ggctgggcac atggtggctg    7920 tgcactcag ctgagtcctt ttccttttca gaatctggga tgttaaccag aagaccttct    7980
atctgaggaa caaccaacta gttgctggat acttgcaagg accaaatgtc aatttagaag    8040
gtgagtggtt gccaggaaag ccaatgtatc tgggcatcac gtcactttgc ccgtctgtct    8100
gcagcagcat ggcctgcctg cacaaaccct aggtgcaatg tcctaatcct tgttgggtct    8160
ttgtattcaa gtttgaagct gggagggcct ggctactgaa gggcacatat gagggtagcc    8220
tgaagagggt gtggagaggt agagtctagg tcagaggtca gtgcctatag caagtggtc    8280 ccagggccac agctgggaag gcaaataccc agaaggcaag gttgaccatt cccttcctca    8340
agtgcctatt aaggctccat gttcctatgt tgttcaaacc taactcaat cccaaattaa    8400 tccaccatgt ataaggttga gctatgtctc ttattcctgg acaccatact cagccatatc    8460
tggtccacac attaacagct ggatgacctt gaagaagctt cacccactct gttcctcagc    8520
tttcccttca gtgggatgat atcaactgga caacaggatg tgcgattctt ttagttccag    8580
ccttccagga tgttttcact cccctgtttg ttgttgtagg atggtattac ctccaccttc    8640
ccaccttccc tatgccctgg ttctgtctcc tgtgcctcgc tctgaaagtg gatgagacct    8700
acaattcctg tcctggtagt tctcctaatg aacacactga agcacgagga agctgagatt    8760
tttgttgcta catgagagca tggaggcctc ttagggagag aggaggttca gagactccta    8820
ggctcctggt ggagccccac tcatggcctt gttcattttc cctgcccctc agcaacactc    8880
ctattgacct ggagcacagg tatcctgggg aaagtgaggg aaatatggac atcacatgga    8940
```

```
acaacatcca ggagactcag gcctctagga gtaactgggt agtgtgcatc ctggggaaag   9000
tgagggaaat atggacatca catggaacaa catccaggag actcaggcct ctaggagtaa   9060
ctgggtagtg tgcatcctgg ggaaagtgag ggaaatatgg acatcacatg gaacaacatc   9120
caggagactc aggcctctag gagtaactgg gtagtgtgca tcctgggaa agtgagggaa    9180 atatggacat cacatggaac aacatccagg agactcaggc tctaggagt aactgggtag    9240 tgtgcttggt ttaatcttct atttacctgc agaccaggaa gatgagacct ctctgccctt   9300
ctgacctcgg gattttagtt ttgtggggac caggggagat agaaaaatac ccggggtctc   9360
ttcattattg ctgcttcctc ttctattaac ctgaccctcc cctctgttct tccccagaaa    9420
agatagatgt ggtacccatt gagcctcatg ctctgttctt gggaatccat ggagggaaga   9480
tgtgcctgtc ctgtgtcaag tctggtgatg agaccagact ccagctggag gtaaaaacat   9540
gctttggatc tcaaatcacc ccaaaaccca gtggcttgaa acaaccaaaa tttttctta    9600 tgattctgtg ggttgaccag gattagctgg gtagttctgt tccatgtggt ggaacatgct   9660
ggggtcactt tggaagctgc attcagcaga gtgccaggct tgcgctgggc atccaaggtg   9720
gtccctcatc ctccaggctc tctttccatg tgatctctca gtgtttaaga gttagttgga   9780
gcttccttac agcatggcgg ctgacttcca aaagggatta ttccaaaaag agcctcaaca   9840
tgcaggcgct tattatgact tctgcttgca tcatcctatt ggccaaagcc agtcacgtgg   9900
ctaagtctag cccctgtga gaggagactg cataagagtg tgaacaccag gagacacggt   9960
cactgggggc caccactgta accatctacc acaggacctg aatctctgtg tgctactccc   10020
ttgctcaagg gcccccctac ccacgcagac ctgctgtctt ctagcaaagc ccatcctcag   10080 gaccttctc ttccaatcct tattgactca aattgattag ttggtgctcc acccagagcc    10140
ctgtgctcct ttatctcatg taatgttaat gggtttccca gccctgggaa acatggctt    10200 tgtctcaggg gcttgctgga tgcaaccta acctcaatgt gagtggccat actgtggcac    10260
tgtcccatcc ctcaccaggg acactgttct ggagggtgac tgcctgttct gtgaggagtg   10320
gggatggcta ggacattgca tggaacacac caccaccca tcttctcaga gctcaaaccc    10380
tgacagaaca ccagctccac aggccttggc ttctgctgat ggtgccgtgt atttaccaga   10440
cttagtggtc caaggccaga gtggcagatt tcccaaagtc aaggtgtgac agtgggacag   10500 cctcttgtg tctttgctgt cctaagaaac ctgggccagg ccaggcgcag tggctcacgc    10560
cttgtaatcc cagcactttg agaggccaag gtgggcagat cacgaggtca ggagtttgag   10620
accagcctgg ccaacattgg tgaaaccctg tctctattaa aaatagaaaa cattagacag   10680
gtgtggtggt gcatgcctgt aatcccagct actcaggagg ctgaggcagg agaatcgctt   10740
gaacccagga ggtggaggtt gcagtgagcc gagattgtgc cactgcactc agcctaggc    10800 gacagagcaa gactccgtct cgggaaaatt aattaataaa taaataaacc taggtcccag   10860
agtcccacag aatggcagac aggagcacct gggggctttt agggtatggc atttcccctg   10920
tactaactct gggctgtcca gaggcgattt catggcgtgg agtggagagg gaggcagcac   10980
aggacttcct aggcctcagc tctcacctgc ccatctttg atttccaggc agttaacatc    11040
actgacctga gcgagaacag aaagcaggac aagcgcttcg ccttcatccg ctcagacagt   11100
ggccccacca ccagttttga gtctgccgcc tgccccggtt ggttcctctg cacagcgatg   11160
gaagctgacc agcccgtcag cctcaccaat atgcctgacg aaggcgtcat ggtcaccaaa   11220
ttctacttcc aggaggacga gtagtactgc ccaggcctgc ctgttcccat tcttgcatgg   11280
```

| | | | | |
|---|---|---|---|---|
| caaggactgc | agggactgcc | agtcccctg | ccccagggct | cccggctatg | ggggcactga | 11340 |
| ggaccagcca | ttgaggggtg | gaccctcaga | aggcgtcaca | acaacctggt | cacaggactc | 11400 |
| tgcctcctct | tcaactgacc | agcctccatg | ctgcctccag | aatggtcttt | ctaatgtgtg | 11460 |
| aatcagagca | cagcagcccc | tgcacaaagc | ccttccatgt | cgcctctgca | ttcaggatca | 11520 |
| aaccccgacc | acctgcccaa | cctgctctcc | tcttgccact | gcctcttcct | ccctcattcc | 11580 |
| accttcccat | gccctggatc | catcaggcca | cttgatgacc | cccaaccaag | tggctcccac | 11640 |
| accctgtttt | acaaaaaaga | aaagaccagt | ccatgaggga | ggttttttaag | ggtttgtgga | 11700 |
| aaatgaaaat | taggatttca | tgattttttt | ttttcagtcc | ccgtgaagga | gagcccttca | 11760 |
| tttggagatt | atgttctttc | ggggagaggc | tgaggactta | aaatattcct | gcatttgtga | 11820 |
| aatgatggtg | aaagtaagtg | gtagcttttc | ccttcttttt | cttcttttt | tgtgatgtcc | 11880 |
| caacttgtaa | aaattaaaag | ttatggtact | atgttagccc | cataattttt | ttttccttt | 11940 |
| taaacactt | ccataatctg | gactcctctg | tccaggcact | gctgcccagc | ctccaagctc | 12000 |
| catctccact | ccagattttt | tacagctgcc | tgcagtactt | tacctcctat | cagaagtttc | 12060 |
| tcagctccca | aggctctgag | caaatgtggc | tcctgggggt | tctttcttcc | tctgctgaag | 12120 |
| gaataaattg | ctccttgaca | ttgtagagct | tctggcactt | ggagacttgt | atgaaagatg | 12180 |
| gctgtgcctc | tgcctgtctc | cccaccaggc | tgggagctct | gcagagcagg | aaacatgact | 12240 |
| cgtatatgtc | tcaggtccct | gcagggccaa | gcacctagcc | tcgctcttgg | caggtactca | 12300 |
| gcgaatgaat | gctgtatatg | ttgggtgcaa | agttccctac | ttcctgtgac | ttcagctctg | 12360 |
| ttttacaata | aaatcttgaa | aatgcctata | ttgttgacta | tgtccttggc | cttgacaggc | 12420 |
| tttgggtata | gagtgctgag | gaaactgaaa | gaccaatgtg | tyttycttac | cccagaggct | 12480 |
| ggcgcctggc | ctcttctctg | agagttcttt | tcttccttca | gcctcactct | ccctggataa | 12540 |
| catgagagca | aatctctctg | cgggg | | | | 12565 |

<210> SEQ ID NO 4
<211> LENGTH: 2172
<212> TYPE: DNA
<213> ORGANISM: Homo sapiens

<400> SEQUENCE: 4

| | | | | | | |
|---|---|---|---|---|---|---|
| gatcccacag | ctatagttca | tggtgctggg | atttgaacct | ctggccacca | gagcccacct | 60 |
| taatgtgtcc | tcctcctgtt | gtcataacag | aaaagtacaa | caccatgatg | acacatcagg | 120 |
| ctatcctggc | aggttcccag | gctgccccaa | tgcccaactt | tctaggttta | caaagttgac | 180 |
| atttacgaag | tttccaggtt | tacaaatcta | gtttctgatt | ctttagtcag | caggaatttc | 240 |
| tctacaaaag | ctgcttcgaa | aatttccagc | caaaccttac | acaccttggc | accacatctt | 300 |
| ggtgagccaa | ggcgaagaga | acaggaagtg | aaggccccat | gggaagtccc | tgcggtcggg | 360 |
| agcacccagg | cggggcgggg | ggtggggggc | tttcctgtgg | ccggctccct | gcccctccca | 420 |
| cccccattca | ggccctgtga | gttgaatgaa | gagaccctgg | gaatgagtcc | aggtctgcag | 480 |
| ggttagagga | aattgaaggc | ccttaccaga | tccctgttga | gaagtttatg | aattatgagc | 540 |
| ccttctgcaa | atgagagggt | tcttccctgt | caggagggac | agattgtagg | tggcaagatt | 600 |
| ggtggcagcc | agtaggctgg | tctgctcctt | cctctctatt | tcatatgtgt | atgaaggcat | 660 |
| tacctgcagc | aagggcctgt | gtaaatgcat | gtgatttaca | gagcatttta | tgtactgcgt | 720 |
| gtcattcatg | cttccggtga | gccctaagtc | taagataggg | cagatagcat | caggtccatt | 780 |
| ttgcagctgt | caaatgagg | tctgaagggc | agaagtggtg | tgcccacaca | cacacaactg | 840 |

```
gttggctgca gacctgggga ctagacccgg gacttcgtcc tgcccagggg tctcttgcca    900
ctgctcccca tcaacttgga tggctttaag catttgtgag ttgtctgctc cctgatggca    960
gaatgcagag acatgaagct acaagcaggt tcgctcccaa cggcaaaaag gaggaggggt   1020
gttcagaaca tcaggtgctt ctagagaaag cagggagaga gtatctggcc ttgtggacaa   1080
tgtcacggca gaggccaggt atagggcatg ggggtaactg gaagcgggat ggaccctctt   1140
attccctaag acatggcttc cacgtagtgc tcaaacaagg cctttgccct tgctgttccc   1200
tccacctgga atattcttcc ccttccttga cattgctcag gtctccactc ttatgtcacc   1260
ctctcagaga gggcttccct ggccactttc cctaaaatag ccacccactc ctaggtccct   1320
caaaagcata tcctgctttg gattttccct atagcaatat gccctatgaa gttatttat    1380
ttgctaactt gtttcttgtc tgttttcctt tgttagagcg ttggggacct tgtctggctt   1440
gttcccaatg cctggaagag tgcctggcac acaggattaa gccaacacat atgttttgaa   1500
tgaatgtgtg cacacatgca tgagctggcg gcagtcgggg ttggggtaag cacgaaggcc   1560
cagctcagtt ctctgcatgt gacctcccat cttacgcaga taagaaccag tttggtttct   1620
gctagcctga gtcaccctcc tggaaactgg gcctgcttgg catcaagtca gccatcagcc   1680
ggcccatctc ctcatgctgg ccaaccctct gtgagtgtgt gggaggggag gctgggctcc   1740
tccttgtact ctctgaggtg ctctggaagg aggggcagct ccaccctggg agggactgtg   1800
gcccaggtac tgcccgggtg ctactttatg ggcagcagct cagttgagtt agagtctgga   1860
agacctcaga agacctcctg tcctatgagg ccctccccat ggctttaggt aagctccttc   1920
cactctcatt ttttcacctg agaaatgaga gaggaaaatg tctacaattg gtgtttatca   1980
aatgctttca ggctctggtg agcaagcgtc caggaaaatg tcaagcgcat ggagctccag   2040
gcctgtctgg gggatctggg cacggggagg catccatggg agaccatgca ggcactctga   2100
ggcagggct  gcaagctagt gcctgctggg gcagcaggtg aacagagagg tgtaactgct   2160
gtgacagaag tc                                                      2172
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
tgtacctaag cccacccttt agagc                                          25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
tggcctccag aaacctccaa                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gctgatattc tggtgggaaa                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
ggcaagagca aaactctgtc                                          20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctcagcaaca ctcctat                                             17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcctggtctg caggtaa                                             17

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctatctgagg aacaaccaac tagtagc                                  27

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
taggacattg cacctagggt ttgt                                     24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ctcaggtgtc ctcgaagaaa tcaaa                                              25

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcttttttgc tgtgagtccc g                                                  21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagcttgttc taccacctga actaggc                                            27

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttacatatga gccttccatg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggcattgat ctggttcatc                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtttaggaat cttcccactt                                                    20

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atggttttag aaatcatcaa gcctagggca                                         30
```

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
aatgaaagga ggggaggatg acagaaatgt                               30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
ttacgcagat aagaaccagt ttgg                                     24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
tttcctggac gcttgctcac cag                                      23

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
atgtatagaa ttccattcct g                                        21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
taaaatcaag tgttgatgta g                                        21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gggattacag gcgtgagcca ccgcg                                    25

```
<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttagtattgc tggtagtatt catat                                    25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaggcgtgag aatctcaaga                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgtcctcaa gtggatctgg                                          20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gggcaacaga gcaatgtttc t                                        21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagtgtgtca gtgtactgtt                                          20
```